(12) United States Patent
Thompson et al.

(10) Patent No.: US 8,419,772 B2
(45) Date of Patent: Apr. 16, 2013

(54) SYSTEMS, METHODS AND DEVICES FOR CORRECTING SPINAL DEFORMITIES

(75) Inventors: Matthew Thompson, Corte Madera, CA (US); Hiram Chee, Santa Cruz, CA (US); Richard Ginn, Gilroy, CA (US); Darin Gittings, Sunnyvale, CA (US); Ivan Sepetka, Los Altos, CA (US); David White, Morgan Hills, CA (US)

(73) Assignee: Reduction Technologies, Inc., Corte Madera, CA (US)

( * ) Notice: Subject to any disclaimer, the term of this patent is extended or adjusted under 35 U.S.C. 154(b) by 199 days.

(21) Appl. No.: 12/795,975

(22) Filed: Jun. 8, 2010

(65) Prior Publication Data
US 2011/0077687 A1   Mar. 31, 2011

Related U.S. Application Data

(60) Provisional application No. 61/185,079, filed on Jun. 8, 2009.

(51) Int. Cl.
    *A61B 17/70*   (2006.01)
(52) U.S. Cl.
    USPC ........................................................ 606/254
(58) Field of Classification Search ............ 606/60, 606/246–279, 57, 324, 90, 102, 103, 105
    See application file for complete search history.

(56) References Cited

U.S. PATENT DOCUMENTS

| | | | |
|---|---|---|---|
| 2,774,350 A | 12/1956 | Cleveland, Jr. | |
| 4,697,582 A * | 10/1987 | William | 606/254 |
| 4,773,402 A | 9/1988 | Asher et al. | |
| 5,201,734 A | 4/1993 | Cozad et al. | |
| 5,290,289 A | 3/1994 | Sanders et al. | |
| 5,391,168 A | 2/1995 | Sanders et al. | |
| 5,413,576 A | 5/1995 | Rivard | |
| 5,486,174 A * | 1/1996 | Fournet-Fayard et al. | 606/261 |
| 5,540,689 A | 7/1996 | Sanders et al. | |
| 5,586,983 A | 12/1996 | Sanders et al. | |
| 5,591,165 A | 1/1997 | Jackson | |
| 5,630,816 A | 5/1997 | Kambin | |
| 5,672,175 A | 9/1997 | Martin | |
| 5,733,284 A | 3/1998 | Martin | |
| 5,938,662 A | 8/1999 | Rinner | |

(Continued)

FOREIGN PATENT DOCUMENTS

| WO | WO 2004/017705 A2 | 3/2004 |
|---|---|---|
| WO | WO 2005/013839 A2 | 2/2005 |

OTHER PUBLICATIONS

Written Opinion, PCT/US08/000416, Jul. 2, 2008.
Written Opinion, PCT/US09/050594, Oct. 28, 2009.

(Continued)

*Primary Examiner* — Eduardo C. Robert
*Assistant Examiner* — James Palmer
(74) *Attorney, Agent, or Firm* — Dickstein Shapiro LLP; Mark Stirrat

(57) ABSTRACT

Provided herein are systems, devices and methods for the correction of spinal deformities with the use one or more implantable rods configured to apply a corrective force to the spine. Methods of minimally invasive implantation of a corrective system are provided, such as where the corrective system is attached only to the spinous process of one or more vertebral bodies. Various corrective systems as well as components thereof are also provided, such as those that allow limited movement with respect to the spinal column.

32 Claims, 58 Drawing Sheets

U.S. PATENT DOCUMENTS

| | | | |
|---|---|---|---|
| 5,951,553 | A | 9/1999 | Betz et al. |
| 6,015,409 | A | 1/2000 | Jackson |
| 6,136,000 | A | 10/2000 | Louis et al. |
| 6,287,308 | B1 | 9/2001 | Betz et al. |
| 6,299,613 | B1 | 10/2001 | Ogilvie et al. |
| 6,315,779 | B1 * | 11/2001 | Morrison et al. ............ 606/281 |
| 6,554,831 | B1 | 4/2003 | Rivard et al. |
| 6,616,669 | B2 | 9/2003 | Ogilvie et al. |
| 6,623,484 | B2 | 9/2003 | Betz et al. |
| 6,706,044 | B2 * | 3/2004 | Kuslich et al. ............... 606/261 |
| 6,783,527 | B2 | 8/2004 | Drewry et al. |
| 6,802,844 | B2 | 10/2004 | Ferree |
| 6,986,771 | B2 | 1/2006 | Paul et al. |
| 6,989,011 | B2 | 1/2006 | Paul et al. |
| 7,125,410 | B2 | 10/2006 | Freudiger |
| 7,588,592 | B2 * | 9/2009 | Winslow et al. ............. 606/249 |
| 2004/0143264 | A1 | 7/2004 | McAfee |
| 2004/0215192 | A1 | 10/2004 | Justis et al. |
| 2005/0143823 | A1 | 6/2005 | Boyd et al. |
| 2005/0182409 | A1 | 8/2005 | Callahan et al. |
| 2005/0203519 | A1 | 9/2005 | Harms et al. |
| 2005/0277935 | A1 * | 12/2005 | Morrison et al. ............... 606/61 |
| 2006/0036244 | A1 | 2/2006 | Spitler et al. |
| 2006/0084982 | A1 * | 4/2006 | Kim ............................... 606/61 |
| 2006/0122620 | A1 | 6/2006 | Kim |
| 2006/0195087 | A1 | 8/2006 | Sacher et al. |
| 2006/0229607 | A1 | 10/2006 | Brumfield |
| 2006/0229612 | A1 | 10/2006 | Rothman et al. |
| 2006/0253121 | A1 | 11/2006 | Gorensek et al. |
| 2006/0282077 | A1 | 12/2006 | Labrom et al. |
| 2007/0016188 | A1 | 1/2007 | Boehm, Jr. et al. |
| 2007/0043355 | A1 | 2/2007 | Bette et al. |
| 2007/0043358 | A1 | 2/2007 | Molz, IV et al. |
| 2007/0055244 | A1 | 3/2007 | Jackson |
| 2007/0078461 | A1 | 4/2007 | Shluzas |
| 2007/0093814 | A1 | 4/2007 | Callahan, II et al. |
| 2007/0118118 | A1 | 5/2007 | Kwak et al. |
| 2007/0162007 | A1 | 7/2007 | Shoham |
| 2007/0270809 | A1 | 11/2007 | Drewry et al. |
| 2008/0021466 | A1 | 1/2008 | Shadduck et al. |
| 2008/0091201 | A1 | 4/2008 | Reiley |
| 2008/0108990 | A1 | 5/2008 | Mitchell et al. |
| 2008/0177326 | A1 * | 7/2008 | Thompson ................... 606/277 |
| 2008/0183209 | A1 | 7/2008 | Robinson et al. |
| 2008/0195153 | A1 | 8/2008 | Thompson |
| 2009/0264927 | A1 * | 10/2009 | Ginsberg et al. ............. 606/246 |

OTHER PUBLICATIONS

Akbarnia et al., Dual Growing Rod Technique for the Treatment of Progressive Early-Onset Scoliosis, SPINE vol. 30, No. 175, pp. S46-S57, 2005.

Aubin et al., Biomechanical Modeling of Posterior Instrumentation of the Scoliotic Spine, Computer Methods in Biomechanics and Biomedical Enginnering, vol. 6(1), pp. 27-33, 2003.

Baumgart et al., Zur Dwyerschen Skoliosenoperation mittels Drähten aus Memory-Legierungen, Arch. Orth. Traum. Surg. 91, pp. 67-75, Feb. 10, 1978 (abstract provided).

Betz et al., An Innovative Technique of Vertebral Body Stapling for the Treatment of Patients With Adolescent Idiopathic Scoliosis: A Feasability, Safety, and Utility Study, SPINE vol. 28, No. 205, pp. S255-S265, 2003.

Betz et al., Preclinical Testing of a Wedge-Rod System for Fusionless Correction of Scoliosis, SPINE vol. 28, No. 205, pp. S275-S278, 2003.

Blakemore et al., Submuscular Isola Rod With or Without Limited Apical Fusion in the Management of Severe Spinal Deformities in Young Children, SPINE vol. 26, No. 18, pp. 2044-2048, 2001.

Braun et al., Creation of an Experimental Idiopathic-Type Scoliosis in an Immature Goat Model Using a Flexible Posterior Asymmetric Tether, SPINE vol. 31, No. 13, pp. 1410-1414, 2006.

Braun et al., Experimental Scoliosis in an Immature Goat Model: A Method That Creates Idiopathic-Type Deformity With Minimal Violation of the Spinal Elements Along the Curve, SPINE vol. 28, No. 19, pp. 2198-2203, 2003.

Braun et al., Fusionless Scoliosis Correction Using a Shape Memory Alloy Staple in the Anteiror Thoracic Spine of the Immature Goat, SPINE vol. 29, No. 18, pp. 1980-1989, 2004.

Braun, et al., Mechanical Modulation of Vertebral Growth in the Fusionless Treatment of Progressive Scoliosis in an Experimental Model, SPINE vol. 31, No. 12, pp. 1314-1320, 2006.

Braun, et al., Relative *Versus* Absolute Modulation of Growth in the Fusionless Treatment of Experimental Scoliosis, SPINE vol. 31, No. 16, pp. 1776-1782, 2006.

Braun, et al., The Efficacy and Integrity of Shape Memory Alloy Staples and Bone Anchors with Ligament Tethers in the Fusionless Treatment of Experimental Scoliosis, The Journal of Bone & Joint Surgery, vol. 87-A, No. 9, Sep. 2005.

Braun et al., Three-Dimensional Analysis of 2 Fusionless Scoliosis Treatments: A Flexible Ligament Tether *Versus* a Rigid-Shape Memory Alloy Staple, SPINE vol. 31, No. 3, pp. 262-268, 2006.

Butterwick et al., Lidocaine Levels During the First Two Hours of Infiltration of Dilute Anesthetic Solution for Tumescent Liposuction: Rapid Versus Slow Delivery, Dermatol. Surg. 29:9, pp. 681-685, Sep. 1999.

Cohn et al., Ambulatory Phlebectomy Using the Tumescent Technique for Local Anesthesia, Dermatol. Surg. 1995:21, pp. 315-318, 1995.

Janicki et al., A Comparison of the Thoracolumbosacral Orthoses and Providence Orthosis in the Treatment of Adolescent Idiopathic Scoliosis, Pediatr. Orthop., vol. 27, No. 3, Jun. 2007.

Kim et al., The Influence of Fixation Rigidity on Intervertebral Joints—An Experimental Comparison Between a Rigid and a Flexible System, J. Korean Neurosurg. Soc. 37:364-369, May 2005.

Lu et al., Treatment of Scoliosis with a Shape-Memory Alloy Rod, Zhonghua Wai Ke Za Zhi, vol. 24, No. 3, pp. 129-131, 187, Mar. 1986 (abstract provided).

Matsumoto et al., Correction of Scoliosis with Shape-memory Alloy, J. Jpn. Orthop. Assoc., vol. 67, No. 4, pp. 267-274, 1993.

Puttlitz et al., A Biomechanical Assessment of Thoracic Spine Stapling, SPINE vol. 32, No. 7, pp. 766-771, 2007.

Rohlmann et al., Flexible non-fusion scoliosis correction systems reduce intervertebral rotation less than rigid implants and allow growth of the spine: a finite element analysis of different features of orthobiom™, Eur. Spine J. 17:217-223, 2008.

Sanders et al., A Preliminary Investigation of Shape Memory Alloys in the Surgical Correction of Scoliosis, SPINE vol. 18, No. 11, pp. 1640-1644, 1993.

Schmerling et al., Using the Shape Recovery of Nitinol in the Harrington Rod Treatment of Scoliosis, J. Biomed. Mater. Res., vol. 10, pp. 879-892, 1976.

Seiger, Ambulatory Phlebectomy: Tumescent Anesthesia Concerning Method of Infiltration, Letters to the Editor, Dermatol. Surg. 24:936 (1998).

Wever et al., Scoliosis correction with shape-memory metal: results of an experimental study, Eur. Spine J. 11:100-106, 2002.

Wever et al., The Surgical Correction of Scoliosis with Shape-Memory Metal, Shape Memory Implants, Ecole Polytechnique de Montreal, Ph.D.L. Yahia, pp. 129-146, 2000.

PCT/US2010/037786—Search Report and Written Opinion, Aug. 3, 2010.

* cited by examiner

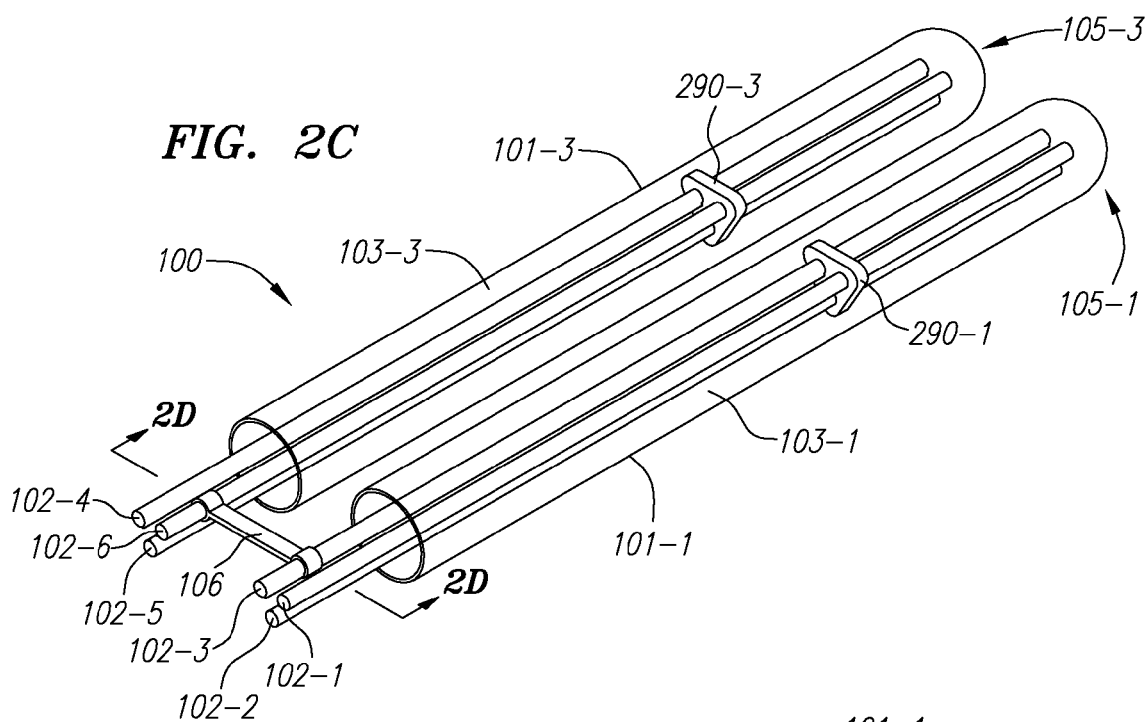
FIG. 2C
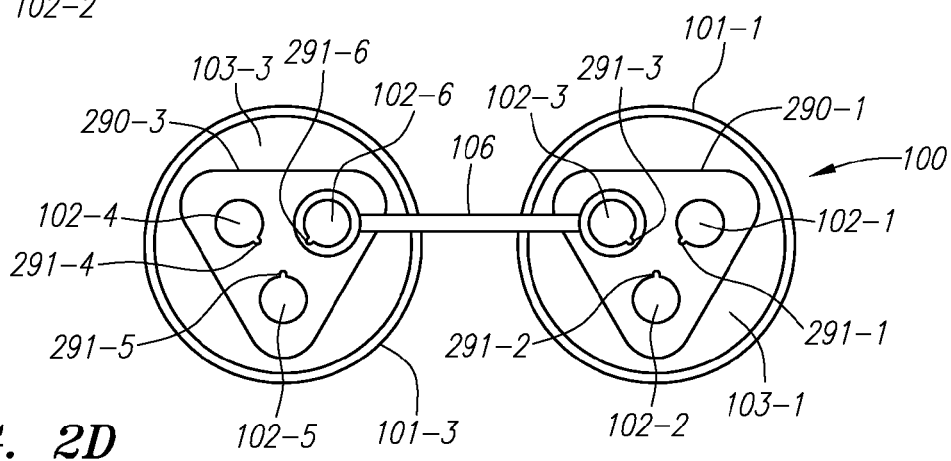
FIG. 2D
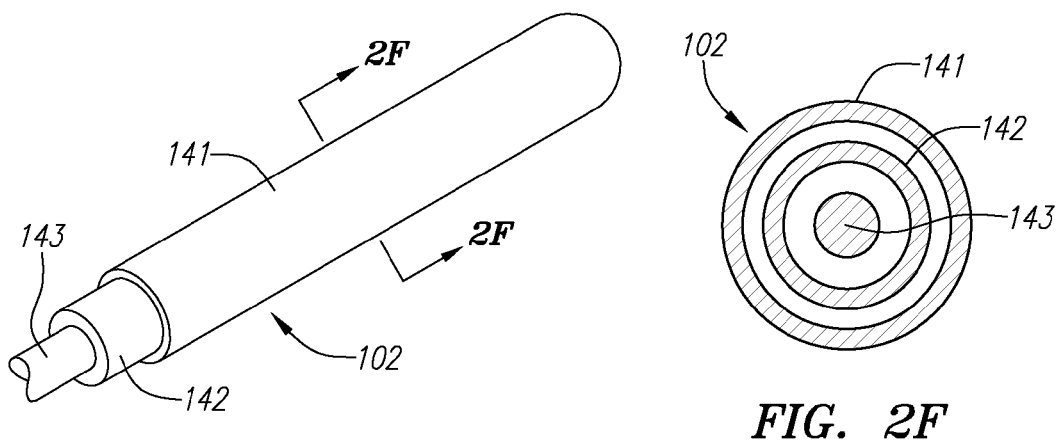
FIG. 2E
FIG. 2F

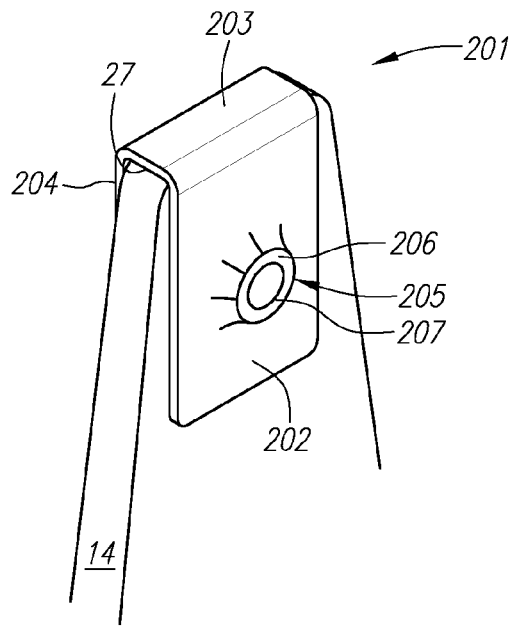
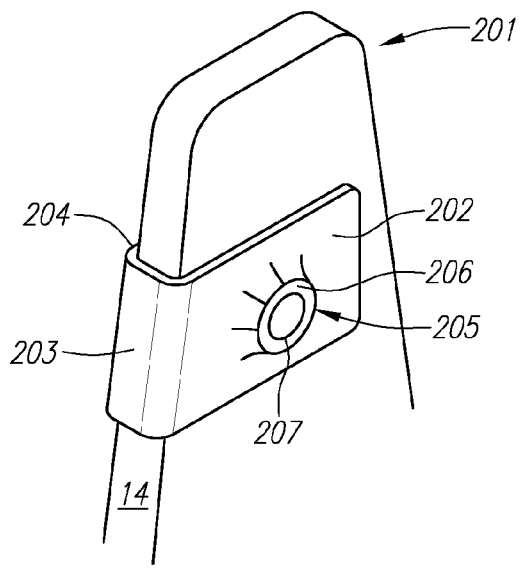
FIG. 4A
FIG. 4B
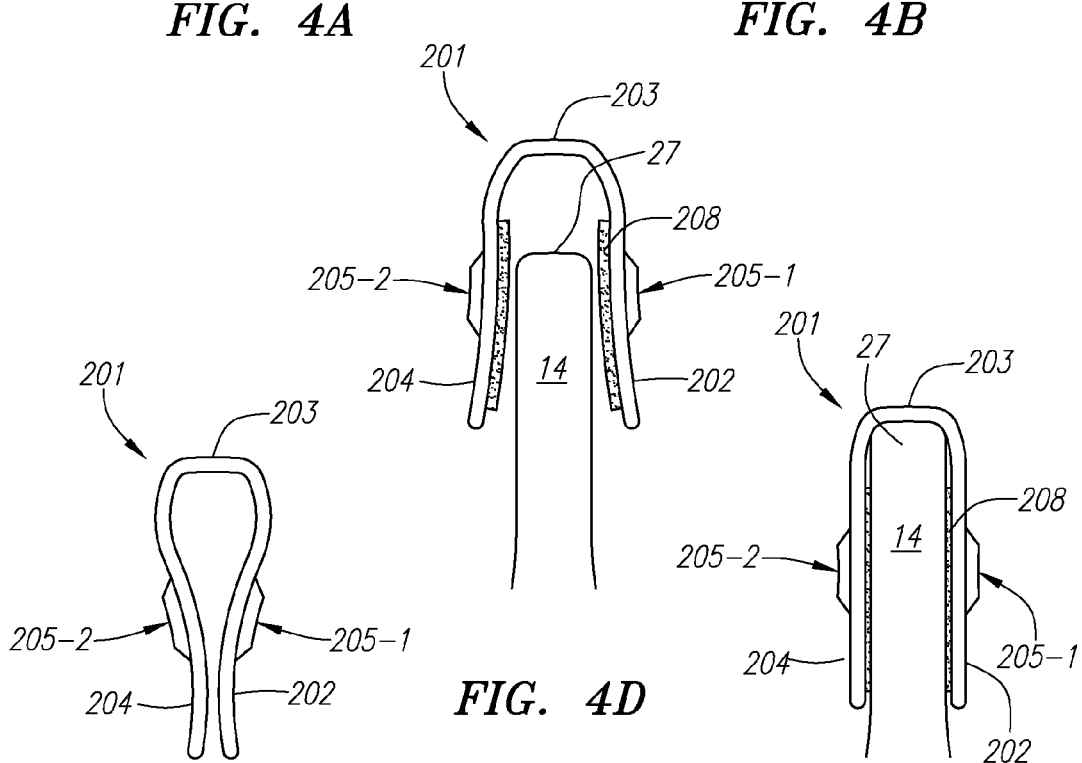
FIG. 4C
FIG. 4D
FIG. 4E

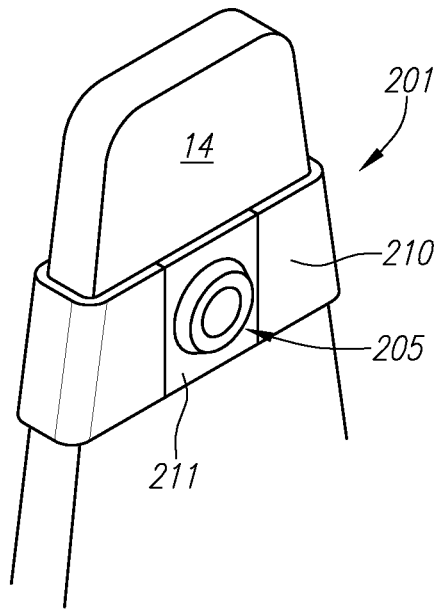
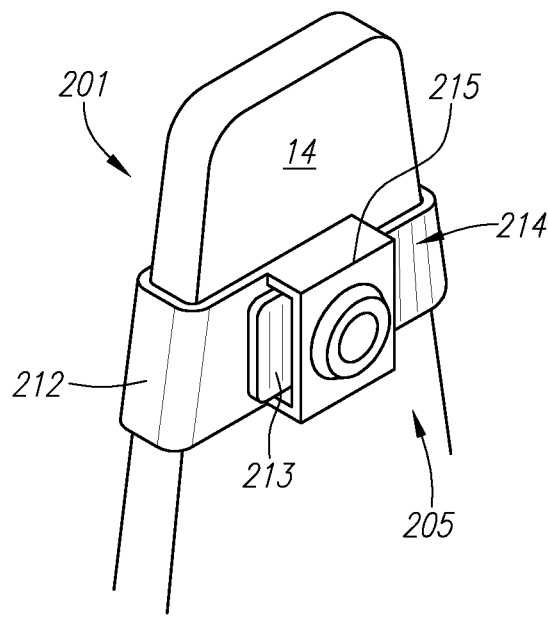
FIG. 5A
FIG. 5B
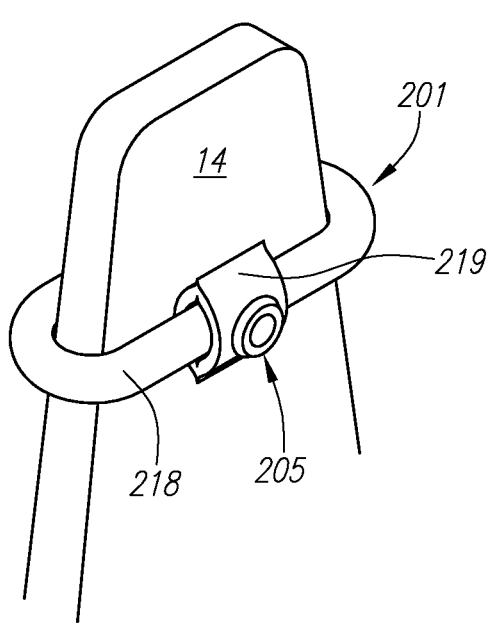
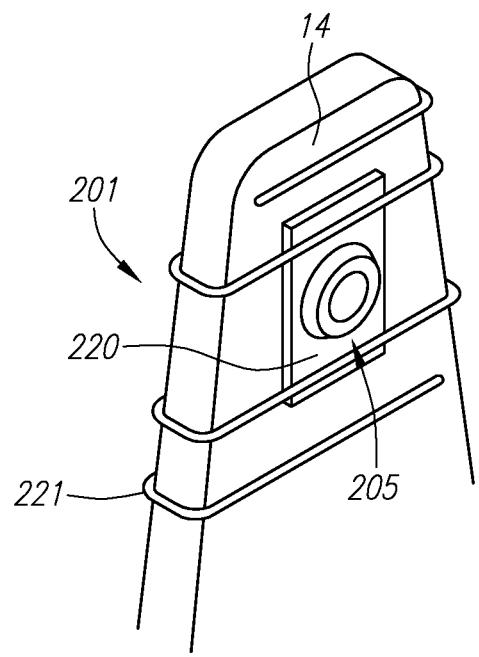
FIG. 5C
FIG. 5D

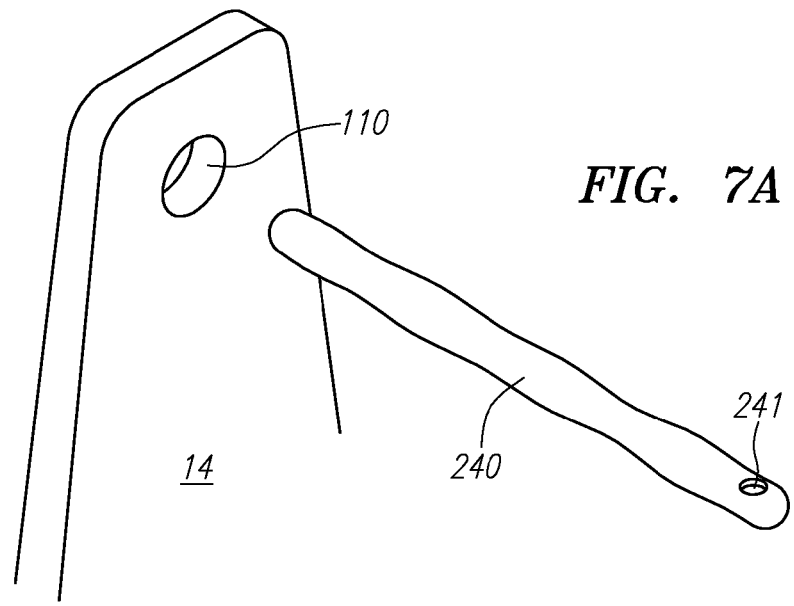
FIG. 7A
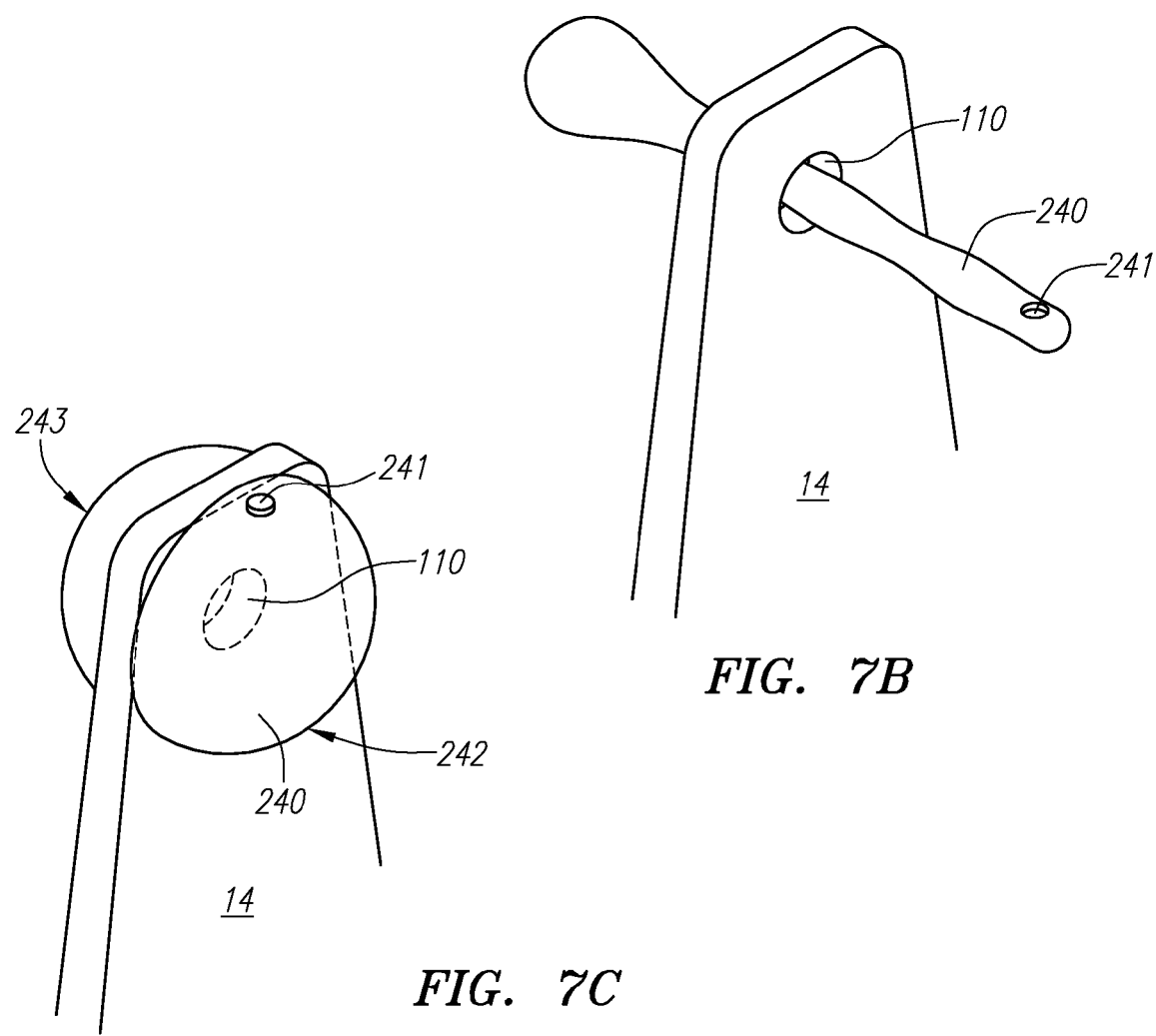
FIG. 7B
FIG. 7C

SYSTEMS, METHODS AND DEVICES FOR CORRECTING SPINAL DEFORMITIES

CROSS-REFERENCE TO RELATED APPLICATIONS

This application claims the benefit of U.S. Provisional Application Ser. No. 61/185,079, filed Jun. 8, 2009, which is incorporated herein by reference.

FIELD OF THE INVENTIONS

The subject matter described herein relates generally to the correction of spinal deformities.

BACKGROUND OF THE INVENTIONS

Scoliosis, a disease that deforms the spine, affects more girls than boys and manifests itself during the teen years when significant growth is experienced. Scoliosis generally combines a horizontal torsion and flexion in a frontal plane and develops in three spatial dimensions. As noted, the disease generally begins with the growth phase, as it is hypothesized that this is probably due to the rotation of one or two vertebral bodies.

Sufferers of scoliosis are generally treated initially with a rigid corset-like orthopedic brace. If this treatment proves unsuccessful, another treatment option can include spinal fusion through invasive surgery. Spinal fusion can oftentimes largely correct a spinal deformity but can also result in complications, such as when the patient advances into adult life. Spinal fusion requires significant invasive surgery, oftentimes including the dissection of the paraspinous muscles of the vertebral body and exposure of the facet joints and laminae. Typical treatment devices include one and oftentimes two rods mounted on either side of the spinal column. If two rods are employed, anchoring means are provided for positioning the rods in spaced-apart parallel alignment. Hooks or screws are employed to anchor the rods along the selected portion of the spinal column for treatment, typically requiring relatively deep penetration of the cortical bone above one or both of the pedicles. The anchors are rigidly locked to the associated rod to prevent relative motion therebetween, and the entire arrangement can be supplemented with bone grafts.

Similar systems have been proposed to treat scoliosis without directly fusing adjacent vertebral bodies. However, because the implantation procedure is so invasive, it can lead to increased blood loss, generation of scar tissue and may induce the risk that the vertebral bodies will still fuse through reaction of the body itself, i.e., auto-fusion.

Others have suggested improvements to the orthosis described above. For example, U.S. Pat. No. 6,554,831 suggests a system that allows for may intraoperative correction and micro-movement of the vertebrae despite implantation of a corrective rod. The '831 patent teaches use of a rigid dual-rod arrangement with fixed and mobile brackets that are anchored to the transverse process and, thus, require significant invasive surgery and risk consequent fusion. The '831 patent discloses attaching a curved rod to a connector device that is, in turn, attached to a pedicle screw by way of a ball-and-socket joint for the purpose of allowing articulation between the rod and the screw. However, this configuration allows the curved rod to rotate out of alignment with the spinal column and, consequently, shifts the direction in which the corrective force is intended to be applied. Use of the ball-and-socket joint with a fixed bracket further causes the point of articulation to be undesirably offset from the rod itself.

U.S. Pat. No. 5,672,175 suggests another approach that theoretically provides a patient with close-to-normal range of motion of the vertebrae by instrumenting the spine with elastic members pre-curved to correct the spinal deformity. Anchoring to the transverse process is also employed, which, again, is a major drawback in performing the techniques suggested in the '175 patent. Further, this device theoretically overcomes the deformity with constant force applied by pre-curved correction members, but this does not allow for resultant changes in the deformity or tissue relaxation. Because of the use of these pre-curved rods, the technique suggested in the '175 patent may actually result in a final deformity completely opposite to the original deformity due to tissue growth and relaxation. Furthermore, this device risks alteration of the natural biomechanics of the spine by fixing the distance between points of attachment. This prohibits any change in distance between pedicles, which shifts the center of rotation of each affected vertebral body anteriorly.

U.S. Pat. No. 4,697,582 suggests a correction apparatus that employs an elastic rod or a pair of elastic rods exhibiting a memory shape of the corresponding part of a normal rachis, the rods being immobilized in rotation in each of the guidance openings. However, the mechanical assembly suggested in the '582 patent is appended to an area on each vertebrae between the spinal process and transverse process, which, again, results in significant invasive surgery, (as discussed earlier) and can result in fusion of vertebral bodies in the to-be corrected region.

Therefore, a spinal correction system is needed to correct spinal deformities while eliminating or significantly reducing the drawbacks of conventional systems.

SUMMARY

Provided herein are systems, devices and methods for the correction of spinal deformities with the use of one or more implantable rods or other corrective devices, configured to apply a corrective force to the spine. These systems, devices and methods are provided herein by way of example embodiments, which are in no way intended to limit the subject matter beyond that of the express language of the appended claims.

Numerous minimally invasive implantation methods are provided, including attachment of the spinal correction system to the patient's spinal column without exposure of the vertebral facet joints. In other embodiments, attachment occurs only to the spinous process of one or more vertebral bodies with varying degrees of invasiveness. Also, example embodiments of corrective systems and devices and methods for attachment of the system are provided. For instance, certain embodiments include connectors that couple with the patient's spinal column and allow limited motion of the rod (or other corrective device) in relation thereto.

Other systems, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be gleaned in part by the study of the accompanying figures in which like reference numerals refer to like parts. The components in the figures are not necessarily to scale, emphasis instead being placed upon illustrating the principles of the subject matter. Moreover, all illustrations are intended to convey concepts where relative sizes, shapes and other detailed attributes may be illustrated schematically rather than literally or precisely.

FIGS. 2C-D are cross-sectional views depicting example embodiments of a spinal correction system.

FIG. 2E is a perspective view depicting an example embodiment of a spinal correction system implanted within a patient.

FIG. 2F is a cross-sectional view taken along line 2F-2F of FIG. 2E.

FIGS. 4A-B are perspective views depicting example embodiments of attachment devices.

FIGS. 4C-E are perspective views depicting example embodiments of attachment devices during implantation.

FIGS. 5A-E are perspective views depicting example embodiments of attachment devices.

FIGS. 7A-C are perspective views depicting stages of implantation of an example embodiment of an attachment device.

FIGS. 19D-E are perspective views of the upper side of example embodiments of the inner housing of a fixed connector.

FIGS. 23B-24 are perspective views of additional example embodiments of a treatment system coupled to a spinal column.

DETAILED DESCRIPTION

Figure 1A:
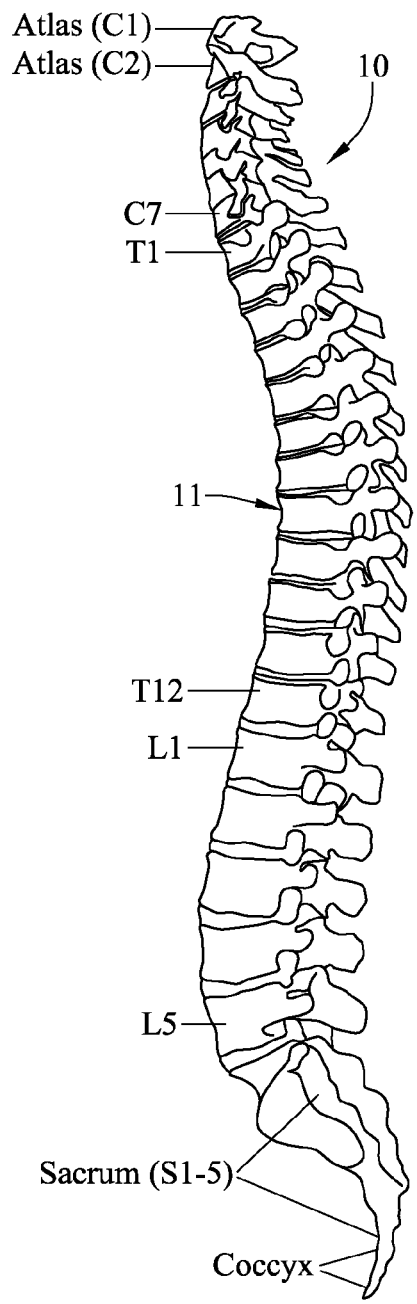
FIG. 1A is a lateral view of an example spinal column.

To facilitate the description of the systems, devices and methods provided herein, a discussion will first be set forth of basic healthy spinal anatomy and deformities that can occur thereto. FIG. 1A is a lateral view of a normal human spinal column 10. Spinal column 10 is divided into three principal regions. The top, or superior, region 2 includes seven vertebral bodies 11 and is referred to as the "cervical" region of the spine. These seven bodies are consecutively labeled C1-C7. The intermediate region 3 includes twelve vertebral bodies 11 and is referred to as the "thoracic" region of the spine. These twelve bodies are consecutively labeled T1-T12. The bottom, or inferior, region 4 includes five vertebral bodies 11 and is referred to as the "lumbar" region. These five bodies are consecutively labeled L1-L5.

Figure 1B:
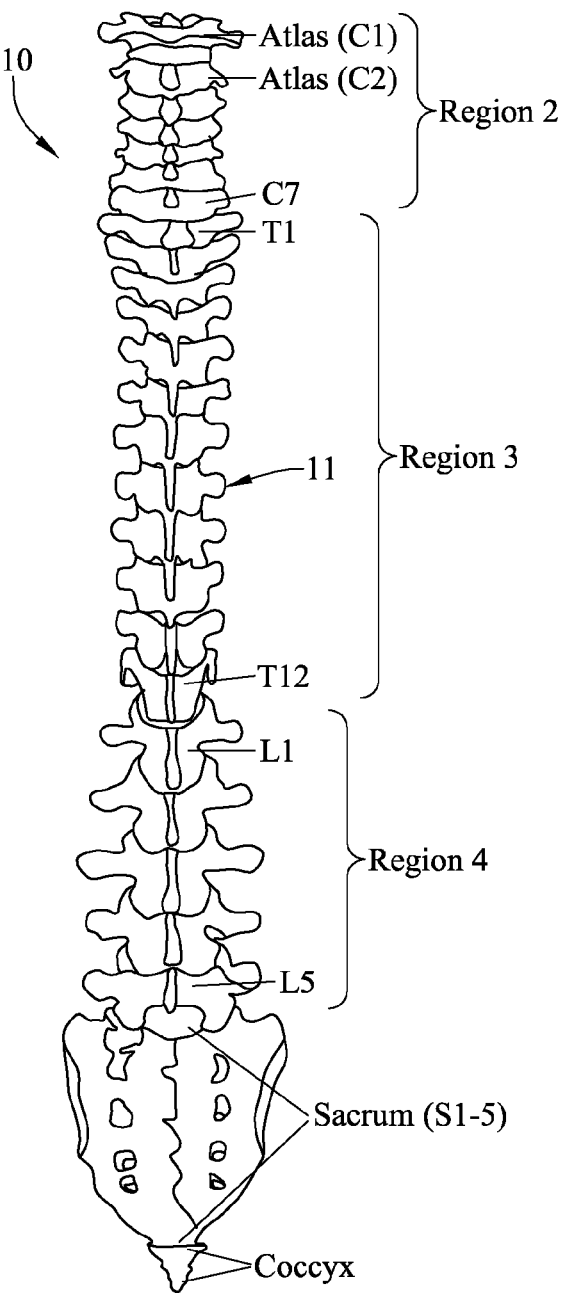
FIG. 1B is a posterior view of an example spinal column.

In a general sense, a typical healthy spinal column 10 has curvature in the sagittal plane (depicted in FIG. 1A) but not in the coronal plane (depicted in the posterior view of FIG. 1B). Referring to FIG. 1A, from a lateral perspective, the curvature of cervical region 2 and lumbar region 4 can be generally described as concave (lordotic), while the curvature of thoracic region 3 can be generally described as convex (kyphotic). Spinal deformities occur when the curvature in any of regions 2-4 changes to an undesirable degree, inhibiting the patient's appearance and/or ability to move and possibly causing pain and/or dysfunction of the nervous system, as well as other symptoms.

Spinal deformities can result from excessive curvature, insufficient curvature or straightening ("flat-back") or even reversal of the curvature of any or all of the spinal regions 2-4 in the sagittal plane, as well as the introduction of lateral (i.e., side-to-side) curvature of any or all of the regions 2-4 in the coronal plane. For instance, excessive kyphotic curvature of thoracic region 3 of the spine is referred to as hyper-kyphosis and excessive lordotic curvature of lumbar region 4 is referred to as hyper-lordosis. Lateral curvature in any of regions 2-4 is generally referred to as scoliosis. Particularly severe spinal deformities, such as scoliosis, can also include pronounced rotation of the vertebral bodies 11. These deformities can involve complex variations from the alignment of a healthy spine in all three spatial dimensions and can occur across the entire length of the spine.

Figure 1C:
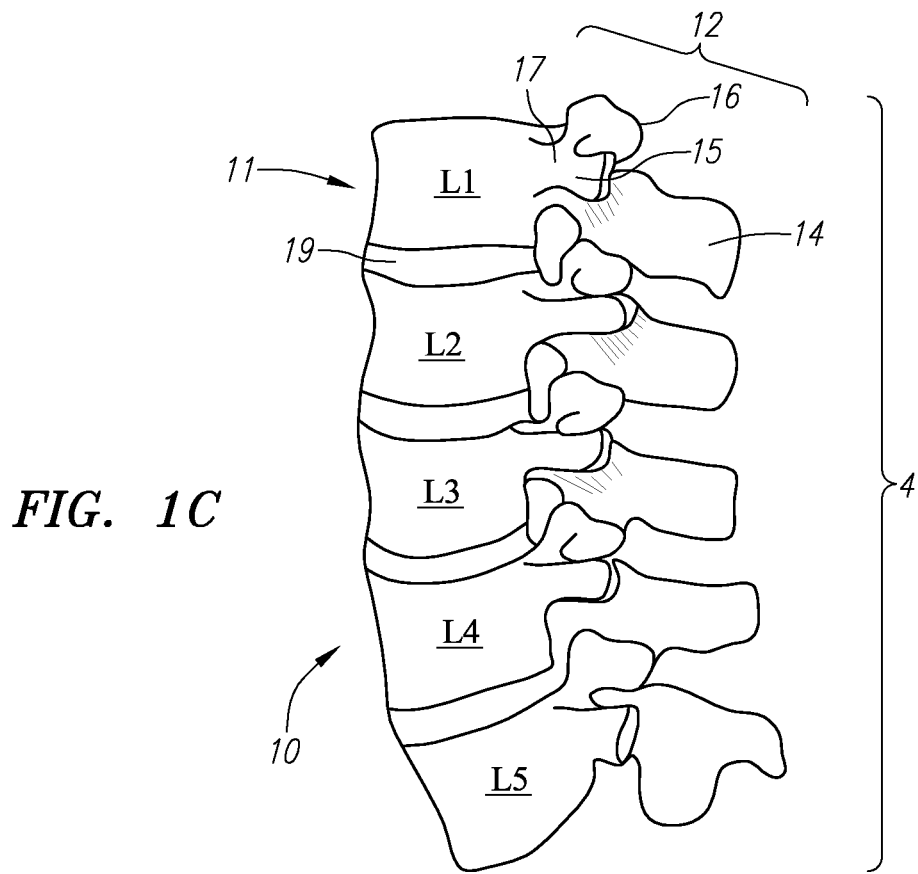
FIGS. 1C-D are lateral views of example portions of a spinal column.

FIG. 1C is a lateral view of lumbar region 4 of a spinal column 10 showing the five lumbar vertebral bodies 11 (labeled L1-L5, respectively), each separated by an intervertebral disc 19. Each vertebral body 11 includes a posterior portion 12 having numerous bony features. The most prominent feature is spinous process 14, which is an elongate, somewhat quadrilateral, fin-shaped feature that is situated the farthest posteriorly from each vertebral body 11. Located adjacent to spinous process 14 are left and right transverse processes 15 and left and right mamillary processes 16 (only the left side of each is shown here). These processes 14-16 are connected to each vertebral body 11 by way of left and right pedicles 17 (again, only left side shown).

Figure 1E:
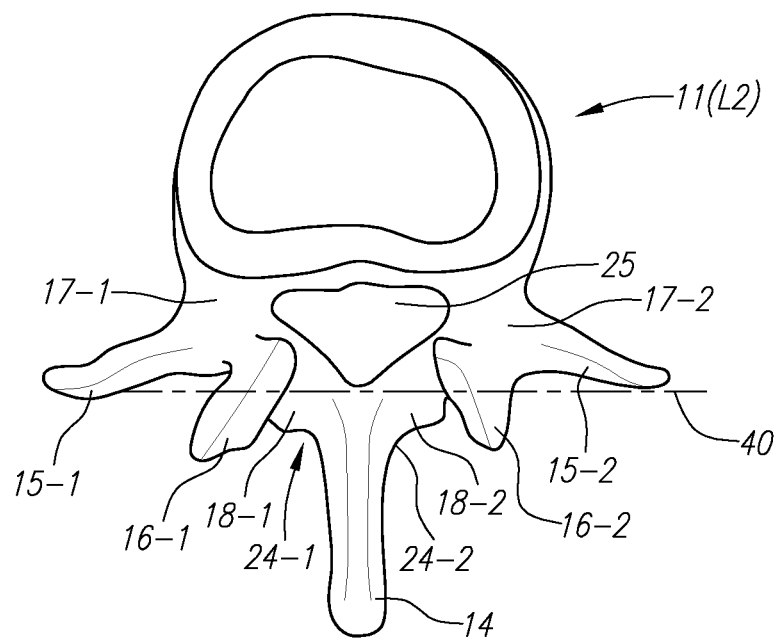
FIG. 1E is a superior view of an example vertebral body.
Figure 1D:
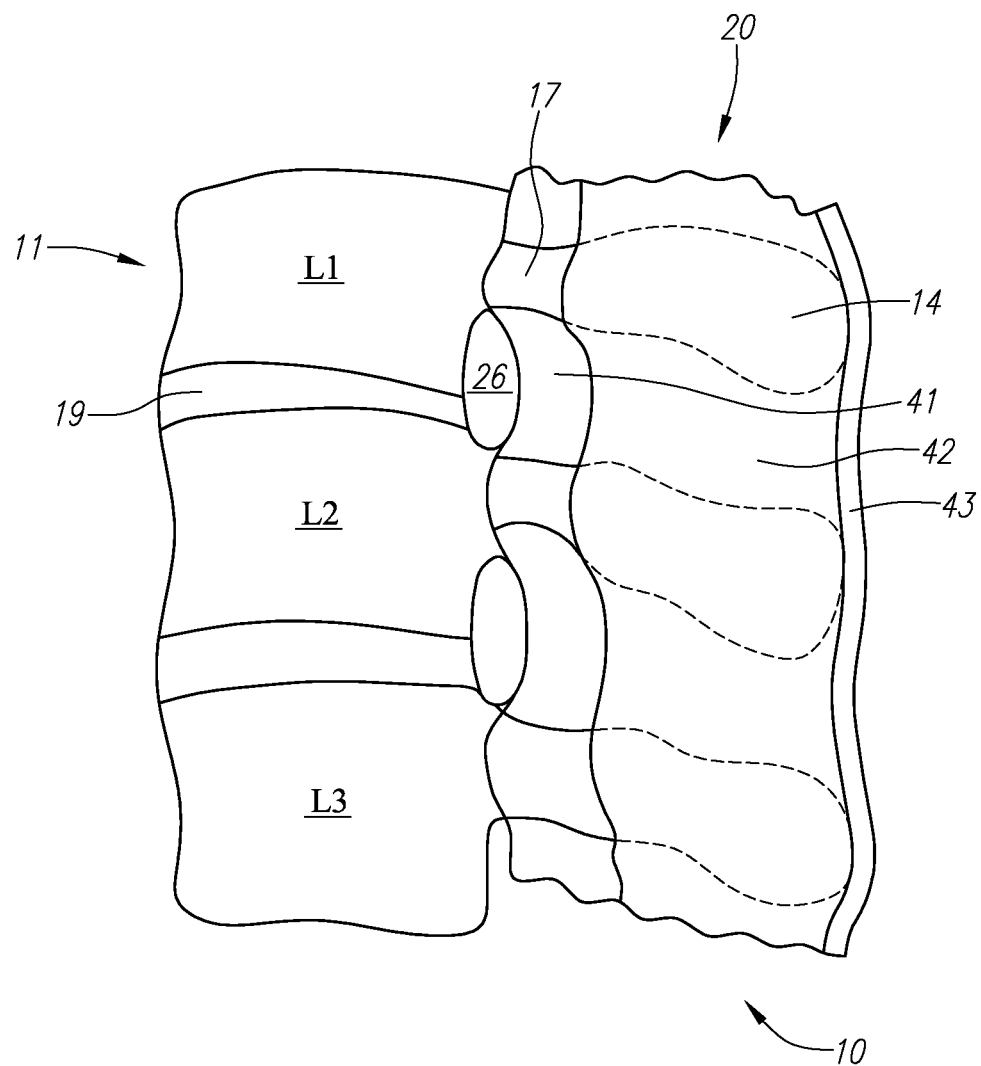

FIG. 1D is a lateral view of three lumbar vertebrae L1-L3 of spinal column 10 with the left side pedicles 17 and processes 15-16 omitted to allow depiction of the interspinous tissue 20. Located adjacent each vertebral body 11 and generally anterior to spinous process 14 (indicated as being obscured by dashed lines) is ligamentum flavum 41, which is immediately adjacent the intervertebral foramen 26. Posterior to ligamentum flavum 41, is the wider interspinous ligament 42 which extends along each side of each spinous process 14. Posterior to interspinous ligament 42 is supraspinous ligament 43, which generally extends along the posterior edge of each spinous process 14 and the interspinous tissue 20.

FIG. 1E is a top-down view of a lumbar vertebral body 11. Here, left and right pedicles 17-1 and 17-2 can be seen in greater detail extending away from vertebral body 11. With regards to the reference scheme used herein, generally, specific ones of a similar element (e.g., left and right pedicles 17-1 and 17-2) will be referred to using the appendix -#, where the # corresponds to a specific one (e.g., 1, 2, 3 . . . N) of a similar element. When general references are made to the elements such that identification of the specific ones is not required, then the -# appendix will be omitted.

Also shown is spinous process 14, left and right transverse processes 15-1 and 15-2, mamillary processes 16-1 and 16-2 and left and right laminae 18-1 and 18-2. The spinous process 14 converges with each lamina 18-1 and 18-2 within a laterally disposed flaring transitional region. This convergence occurs generally along the apex 24-1 and 24-2 of each flaring transitional region, respectively. Anterior to each lamina 18 is a space referred to as the vertebral foramen 25. It is through the vertebral foramen 25 (shown in FIG. 1E) and intervertebral foramen 26 (shown in FIG. 1D) that the spinal cord and other spinal nerves (not shown) are routed.

Figure 1F:
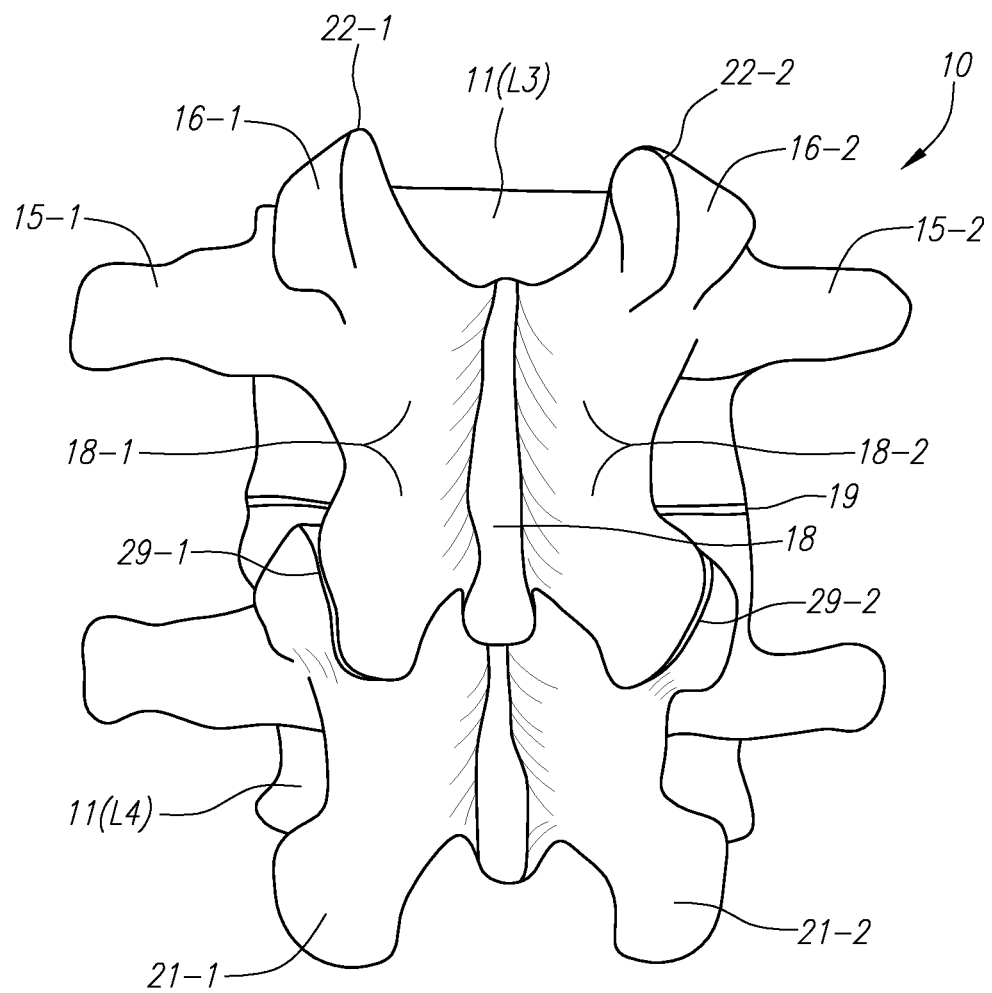
FIG. 1F is a posterior view of an example portion of a spinal column.

FIG. 1F is a posterior view of two vertebral bodies 11, specifically L3 and L4. Left transverse process 15-1 and right transverse process 15-2 are shown extending laterally from each side of bodies 11. Superior to transverse processes 15 are mamillary processes 16-1 and 16-2 and superior articular processes 22-1 and 22-2. Posterior to transverse processes 15 are the left and right laminae 18-1 and 18-2, respectively. At the base of each vertebral body 11 are inferior articular processes 21-1 and 21-2. The joint or interface between superior articular processes 22 and inferior articular processes 21 of the adjacent vertebral body 11 is referred to as facet joint 29, of which a left facet joint 29-1 and a right facet joint 29-2 are depicted here between L3 and L4. Each vertebral body 11 has two sets of facet joints 29, formed in part by the superior articular process 22 at one end and the inferior articular process 21 at the opposite end.

Facet joints 29 are hinge-like and link adjacent vertebral bodies 11 together. Facet joints 29 are referred to as synovial joints, which means that each joint 29 is typically surrounded by a capsule of connective tissue and produces a fluid to nourish and lubricate the joint. The joint surfaces are coated with cartilage to allow smooth motion articulation between adjacent bodies. Dissection of tissue from, and/or exposure of, the facet joint 29 can lead to auto-fusion, especially in younger patients. Auto-fusion is the internal fusion of adjacent vertebral bodies 11 together by the patient's own body, and severely diminishes the patient's freedom of motion. Auto-fusion can also be caused by exposure of one or both of the laminae 18.

The systems, devices and methods provided herein are configured to correct spinal deformities through the application of corrective forces to the spinal column. Preferably, one or more flexible, shape-memory rods are implanted in close proximity to the spinal column. The rods are preferably formed from metals or metal alloys such as nickel-titanium alloys (e.g., nitinol), titanium, elgiloy, stainless steel, and the like, or polymeric materials such as Liquid Crystal Polymers (LCP), polyetheretherketone (PEEK), tent-butyl acrylate, poly(ethylene glycol) dimethacrylate, polyetherurethane, and the like. The polymeric materials may be modified to increase their strength and toughness with fillers, such as fiber, graphite and the like. Unless otherwise noted, this description will be of a system incorporating dual rods located on opposite sides of the spinal column.

These rods are preferably preshaped or shape-set to a curvature that when applied to a deformity results in a healthy spine. For example, for treatment of each of the three regions of the spinal column, the rods are configured with kyphotic curvature in the portion corresponding to the thoracic region and lordotic curvature in the portions corresponding to the cervical and lumber regions. The rods are then distorted during placement over the deformed portion of the spine such that the rods then apply a corrective force to the spine. Thus, even if the spinal deformity bridges into multiple regions of the spine (cervical, thoracic, lumber), the rods are configured to correct for those corresponding changes in lordosis and kyphosis.

Alternatively, one or more straight rods (or equivalent corrective devices) can be used while preserving the proper lordotic and kyphotic curvature. For instance, one rod that is generally straight in the sagittal plane, but it has curvature in the coronal plane, and can be coupled to the spinal column at various vertebral bodies. The distance between the rod and vertebral body can be varied to accommodate the proper lordotic and kyphotic curvature. In another example, multiple individual rods can be used, with each being generally straight in the sagittal plane and curved in the coronal plane. These rods can be positioned end-to-end along the portion of the spinal column to be corrected. As opposed to the single-rod example, the distance between the ends of each rod and the vertebral bodies can be generally fixed, but each rod can be coupled at the appropriate angle to simulate the lordotic and/or kyphotic curvature, effectively replacing a rod with curvature in the sagittal plane with multiple straight rods arranged to match the curvature in the sagittal plane.

Preferably, correction occurs by the use of only one set of implanted rods over the course of treatment, although correction can also be achieved by way of iterative replacement of the rods. In such an embodiment, the first set of rods can be shaped to correct some, but not all, of the deformity in the spinal column (or can be shaped or sized to resemble a healthy spine but with relatively less strength, such that it applies corrective force at a relatively lower level). After that set of rods has been implanted for a length of time sufficient to cause the incremental correction, a new set of rods can be implanted with a shape (or strength) that is configured to achieve incrementally more correction. This process can be repeated as many times as needed until the spinal column is corrected to the desired extent. The use of an iterative process requires multiple surgeries, but can allow for the use of rods that are relatively more flexible, thereby allowing the patient greater freedom in movement. The iterative process also allows the shape of the rods and location of implantation to be fine-tuned to exert corrective forces where they are needed to achieve the desired outcome.

Figure 2A:
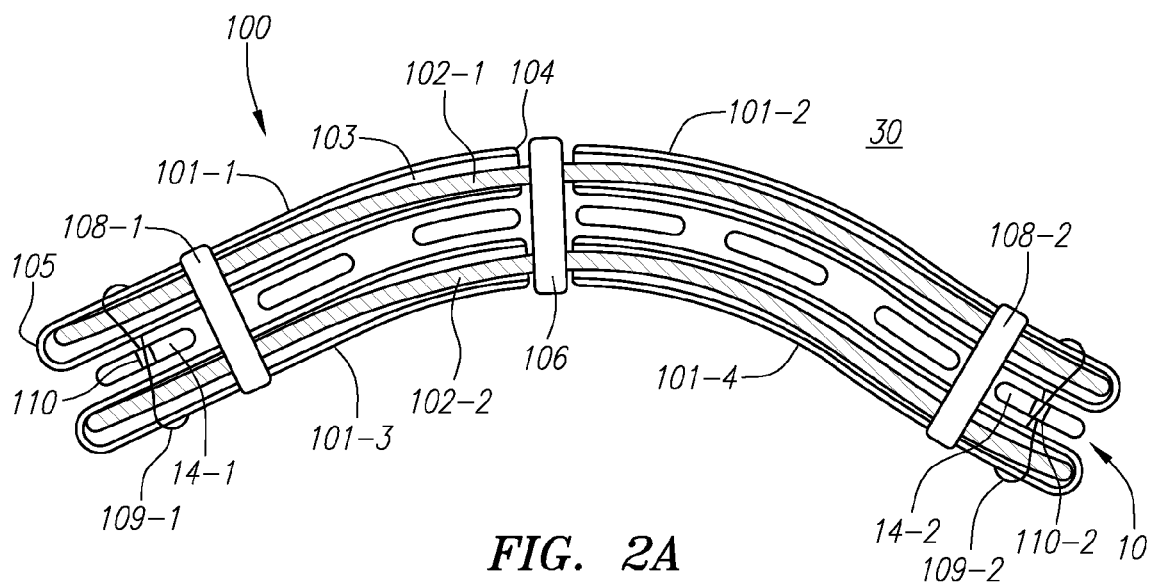
FIG. 2A is a posterior view depicting an example embodiment of a spinal correction system implanted within a patient.

FIG. 2A depicts an example embodiment of a spinal correction (or corrective) system 100 implanted within a body 30 of a patient. Here, system 100 includes tubular members 101, each having an inner lumen 103 for slidably receiving a rod 102. Here, each rod 102 is received within two tubular members 101, although it should be noted that any number of one or more tubular members 101 can be used for each rod 102. For ease of description, tubular members 101 will be referred to herein as sleeves.

There are at least several benefits for using sleeve 101 outside rod 102. Sleeve 101 facilitates the placement or replacement of rods 102 by forming a readily accessible pathway for rod 102 into the implantation space. The new rod would also not require attachment to the spinous process, as the sleeve 101 is preferably already attached.

Also, avoidance of rigid attachment to the bone can be desired since fixing any member to bone can potentially put large, localized forces on the bone in the areas of contact. As corrective rods 102 can be long, they provide the opportunity to place large moments on the rigid attachment. Allowing rods 102 limited lateral and rotational freedom of movement within sleeves 101 reduces the stress placed on the rigid attachment. Sleeves 101 also isolate bone and tissue from frictional forces generated by the moving rod 102. Sleeves 101 can also contain and isolate any wear particles that may be generated by movement of rods 102.

Figure 2B:
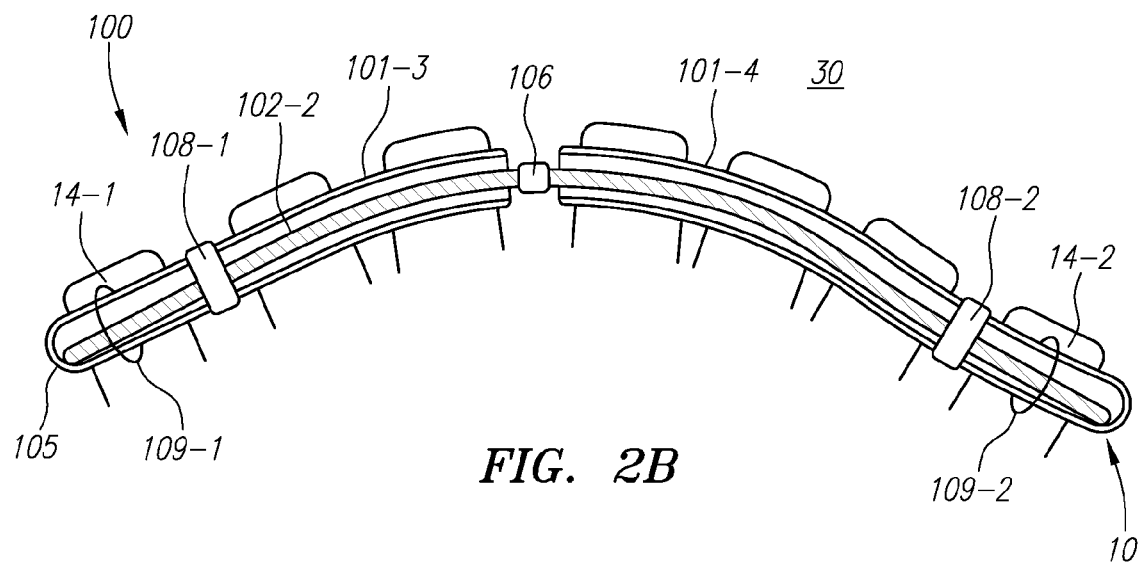
FIG. 2B is a lateral view depicting an example embodiment of a spinal correction system implanted within a patient.

FIG. 2A is a posterior view of system 100 implanted along spinal column 10. FIG. 2B is a lateral view of the embodiment of FIG. 2A showing rod 102 and sleeve 101 on the left side of the spinal column 10. As shown in FIG. 2A, this example of spinal column 10 exhibits a scoliotic bend to the patient's right for which correction is desired (patient's head is to the left as shown). In this embodiment, system 100 includes four sleeves 101-1 through 101-4 and two rods 102-1 and 102-2. Sleeves 101 are shown in cross section to show rod 102 within. Preferably, each sleeve 101 has an open end 104 for receiving rod 102 and a closed end 105. Lumen 103 is sized to slidably receive rod 102 while at the same time allowing limited rotational or lateral movement of rod 102 within lumen 103. Sleeves 101 are preferably formed from a polymeric material such as polyethylene (PE), polypropylene, polyetheretherketone (PEEK), polytetrafluoroethylene (PTFE), fluorinated ethylene/propylene copolymers (REP), silicates, hydrogels, hydrophilic coatings, polyurethane (PU), polyethylene ptherethalate (PET), polyimide, styrene-ethylene-butadiene styrene (SEBS), and the like.

Sleeves 101 can also be formed from coiled wire or ribbon or can be configured as slotted tubes (either polymeric or metallic). The pattern of the coil or slotted tube can be optimized for flexibility and pushability. Sleeves 101 can be coated with lubricious coatings, such as hydrophilic coatings to facilitate advancement of the sleeve through the surrounding anatomy and to facilitate introduction or removal of the rods within the sleeves.

Here, rod 102-1 is received within superiorly located sleeve 101-1 and inferiorly located sleeve 101-2. Likewise, rod 102-2 is received within superiorly located sleeve 101-3 and inferiorly located sleeve 101-4. Sleeves 101 and rods 102 preferably extend a sufficient amount past the most superiorly and inferiorly vertebral bodies 11 to be treated in order to accommodate growth and the full range of motion in any direction (i.e., flexion and extension, rotation and bending). Sleeves 101 are arranged such that a gap exists to expose rods 102 such that a rigid rod connector, or coupling device, 106 can be coupled with each rod 102 to hold rods 102 in position relative to each other and prevent each rod from rotating significantly with respect to each other and with respect to the spinal column. For instance, prevention of rotation with respect to the spinal column precludes the curved portion of the rod from rotating out of the sagittal plane and into the coronal plane to accommodate the deformity.

Although spaces are shown between sleeves 101-1 and 101-3 as well as sleeves 101-2 and 101-4 to allow direct coupling of rod connector 106 with each rod 102, this space can be omitted and sleeves 101-1 and 101-3 can be one continuous sleeve (likewise for sleeves 101-2 and 101-4). Direct connection to rods 102 can be foregone with some other measure to prevent rod rotation applied. Alternatively, apertures can be provided in the sleeves to allow access to rods 102. Preferably, only one rigid rod connector 106 is applied between rods 102-1 and 102-2, at a centrally located position. However, if desired, any number of rigid rod connectors 106 can be applied at any location along the length of system 100.

Each superiorly located sleeve 101-1 and 101-3 can be optionally coupled together by way of a lateral coupling device 108-1. Similarly, the inferiorly located sleeves 101-2 and 101-4 can be coupled together by way of a lateral coupling device 108-2. Coupling device 108 acts to maintain sleeves 101 in position with respect to each other (e.g., so as to prevent sleeves 101 from migrating laterally and also to allow the force applied from a rod on the convex side to act on the deformity). Coupling device 108 can have any configuration suitable for the needs of the application. Here, coupling device 108 is configured as a band. Any number of coupling devices 108 can be applied at any location along the length of system 100.

In addition, sleeves 101 can be coupled with spinal column 10 by way of a spinal coupling device 109. Here, a superiorly located spinal coupling device 109-1 couples sleeves 101-1 and 101-3 to a spinous process 14-1. Specifically, spinal coupling device 109-1 is routed through an iatrogenic, or man-made, opening 110-1, in spinous process 14-1. Opening 110 can be formed by a piercing element (e.g., guidewire, trocar and the like) or a drill-like element. An example instrument for piercing the spinous process is described in the copending U.S. Patent Application Ser. No. 60/988,432, filed Feb. 7, 2008, and entitled "Hand-held Instruments That Access the Spinous Process of a Vertebrae," which is fully incorporated by reference herein. Spinal coupling device 109 can also be configured to be secured partially or entirely around the spinous process rather than through it. Spinal coupling device 109 prevents sleeve 101-1 and 101-3 (and, likewise, superior ends of rods 102-1 and 102-2) from migrating posteriorly away from spinal column 10 during flexion of spinal column 10. In some circumstances, spinal coupling device 109 can also prevent sleeves 101 from migrating anteriorly during spinal extension.

An inferiorly located spinal coupling device 109-2 couples sleeves 101-2 and 101-4 together through iatrogenic opening 110-2 within an inferiorly located spinous process 14-2. Coupling device 109 can have any configuration suitable for the needs of the application. Here, coupling device 109 is configured as a tether. Although only coupling device 109 is shown coupled with the patient's spinal column 10, rod coupling device 106 can be optionally coupled to the patient's spinal column (e.g., spinous process) as well.

Preferably, system 100 is only coupled to the spinal column at one superiorly located position and one inferiorly located position, in order to allow significant freedom of movement to the patient. However, system 100 can be coupled with the spinal column at additional locations (e.g., a central location) if desired. For each location where system 100 is coupled with the spinal column, the system can be configured to slide superiorly and inferiorly to accommodate the patient's movement. Rigid rod connector 106 can be implanted directly through the interspinous ligament and can act as an anchor for the entire spinal correction system, preventing significant movement superiorly and inferiorly.

Sleeves 101 are configured so that they can be tunneled under the skin either on their own or with the help of an instrument inserted into the sleeve lumen. The sleeves are preferably configured to conform to the anatomy in the proximity of the spinous processes and surrounding tissue as they are advanced. The sleeves themselves preferably do not impart any corrective forces, but rather serve as guides for the rods that are placed through them. In an alternative embodiment, sleeves 101 are configured with a shape similar to that of the desired healthy spine. If iterative correction is applied, in order to prevent the need for removal of sleeves 101 during rod replacement, sleeves 101 are preferably flexible to a degree sufficient to accommodate rods 102 of varying shapes and sizes.

Upon attachment of corrective system 100, corrective force is applied to each vertebral body 11 lying adjacent to rods 102. The force is transmitted to each body 11 through the connection of the rods or sleeves directly to one or more vertebral bodies, as well as by the proximity of rods 102 with the spinous processes 14, the interspinous tissue 20 and/or the various other features of vertebral bodies 11 within the treatment region.

The use of an inferiorly and superiorly located sleeve on either side of the spinal column is also conducive to the use of multiple rod segments on both sides of the spinal column. For instance, rod 102-1 can include a first segment received within superiorly located sleeve 101-1 and a second, separate segment received within inferiorly located sleeve 101-3. Rigid rod connector 106 can be configured to couple the rod segments together as well as fix those segments with respect to rod 102-2 (or segments thereof) and the spinal column. The use of rod segments can facilitate the insertion procedure, as will be described in more detail below.

It should also be noted that a bundle of two or more rods or rod segments can be placed on either side of the spinal column. For instance, in one example embodiment, instead of a superiorly placed rod segment on the left side of the spinal column, a bundle of three rod segments can be placed superiorly on the left side of the spinal column. These three rod segments can couple with a similar inferiorly placed bundle of three rod segments, or a different number of inferiorly placed rod segments can be used. Preferably, the bundle of rods or rod segments is banded or otherwise connected together and placed within a sleeve, although each rod or rod segment could be placed within its own sleeve, with the sleeves then being coupled together.

FIG. 2C is a perspective view depicting an example embodiment of spinal correction system 100 having multiple rods 102 arranged in a bundle. FIG. 2C depicts the superiorly located portion of system 100 including sleeves 101-1 and 101-3. Sleeves 101-1 and 101-3 are shown to be transparent for ease of illustration of the components therein. FIG. 2D is a cross-sectional view taken along line 2D-2D of FIG. 2C.

Received within lumen 103-1 of sleeve 101-1 is a bundle of three rods 102-1, 102-2 and 102-3, which are held in relation to each other by coupling device 290-1. Similarly, received within lumen 103-3 of sleeve 101-3 is a bundle of three rods 102-4, 102-5 and 102-6, which are held in relation to each other by coupling device 290-3. Coupling devices 290 preferably allow rods 102 to slide within the respective lumens in coupling devices 290. A similar arrangement could be present in the inferiorly located portion of system 100 within sleeves 101-2 and 101-4. Fixed coupling device 106 is coupled with rods 102-3 and 102-6 of the two respective bundles. Each rod 102 can include a keyed portion to maintain the radial orientation of each rod with respect to the others. Here, the keyed portion is formed by a rib 291 located along the length of each rod. Ribs 291 are configured to interface with a complementarily shaped lumen within coupling devices 106 and 290.

This configuration of system 100 allows the medical professional to adjust the force applied while minimizing the effort necessary to remove portions and implant new portions of system 100. For instance, to lessen the force applied, the medical professional can simply remove a rod from each bundle. Rods 102-1, 102-2, 102-4 and 102-5 are each preferably only slidably received within coupling devices 290, making removal relatively simple. Rods 102-3 and 102-6 are preferably left in place to avoid the need to remove and reattach coupling device 106. Similarly, if an open lumen is present in coupling devices 290, a rod 102 can be added to increase the force applied. Use of multiple small rods in a bundled arrangement can also provide significant improvements in lifetime and fatigue performance as compared to a single larger rod of the same material. One of skill in the art will readily recognize that any number of rods can be used within each bundle.

FIG. 2E is a perspective cutaway view depicting another example embodiment of rod 102. Here, rod 102 is configured with multiple components 141-143 to allow adjustment of the corrective force applied. FIG. 2F is a cross-sectional view of rod 102 taken along line 2F-2F of FIG. 2E. Included are an outer tubular component 141, an inner tubular component 142 and a central core component 143. Similar to the previous embodiment, this embodiment allows the applied corrective force to be adjusted with minimal effort during surgery. Outer tubular component 141 is preferably coupled with a similar component on the other side of the spinal column by way of a fixed coupling device (such as coupling device 106 described herein). Adjustment of the applied corrective force can be accomplished by modification of the components present. Preferably, the corrective force can be lessened by removal of inner tubular component 142 or core component 143. Likewise, force can be added through the addition of components. One of skill in the art will readily recognize that any number of components can be present.

Figure 2G:
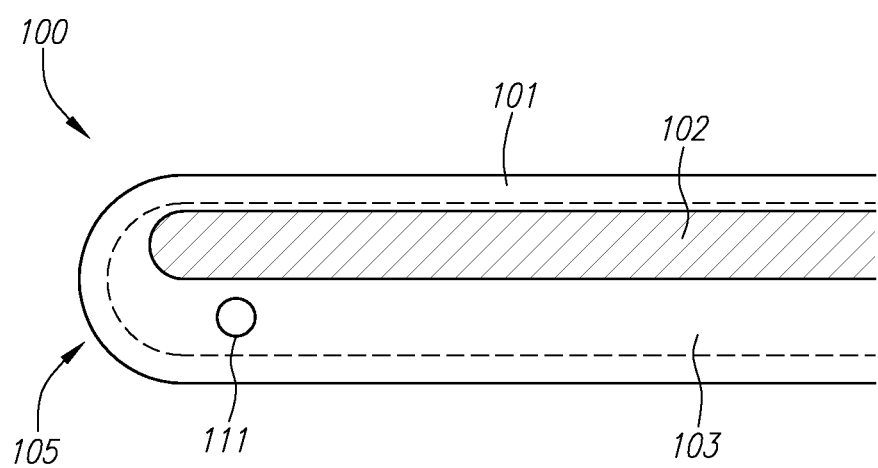
FIGS. 2G-H are cross-sectional views of additional example embodiments of a spinal correction system.

FIG. 2G is a cross-sectional view of an example embodiment of corrective system 100 where tubular member 101 includes two through-holes 111 in opposing positions in the side wall through which a coupling device (e.g., coupling devices 108 or 109 described earlier) can be routed. Through-holes 111 can be offset to one side of tubular member 101 so as to not interfere with the movement or location of rod 102 within inner lumen 103.

Figure 2H:
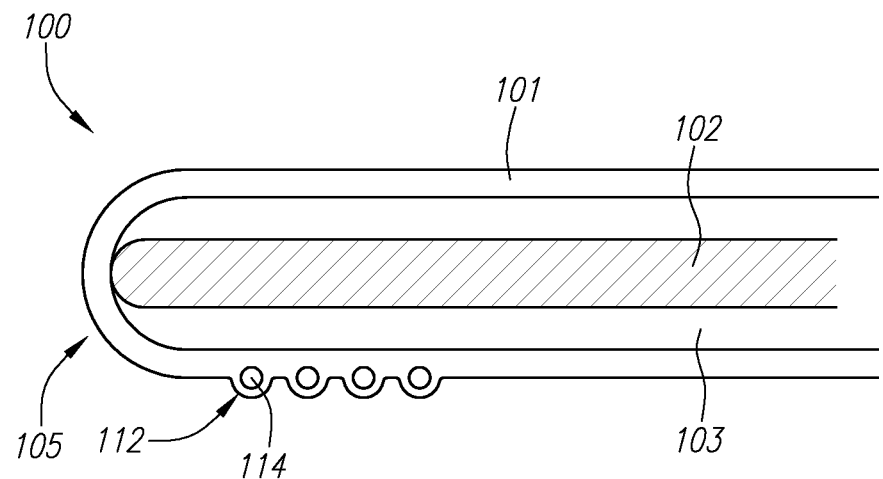

FIG. 2H is a cross-sectional view of another example embodiment of corrective system 100 where tubular member 101 includes one or more (in this example four) raised portions 112 each having an aperture or through-hole 114. A coupling device (e.g., coupling device 108 or 109) can be routed through one or more of apertures 114 to couple tubular member 101 with another tubular member 101 (not shown) or with a portion of the patient's anatomy, such as spinous process 14 (also not shown).

The use of multiple raised portions provides the medical professional with optional locations on tubular member 101 to use for coupling. For example, the raised portion 112 located in the most suitable position for coupling to the spinous process can be selected. Alternatively, the medical professional can couple through more than one aperture 114 for added security or strength. For instance, a tether (e.g., braided wire) could be routed through each of apertures 114 to distribute the load in a relatively uniform fashion. Here, raised portions 112 are shown arranged in series longitudinally along the tubular member 101, although it should be understood that raised portions 112 can also be arranged radially about the circumference of tubular member 101, or any combination thereof Also, instead of raised portions 112, tubular member 101 can include recessed portions having a strut or hook about which the coupling device can be routed, giving tubular member 101 an overall lower profile.

Figure 2J:
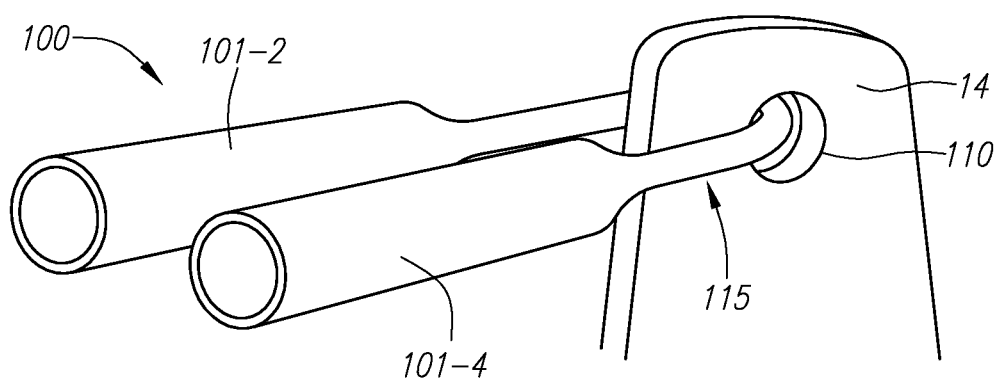
FIGS. 2I-J are perspective views of additional example embodiments of a spinal correction system.
Figure 2I:
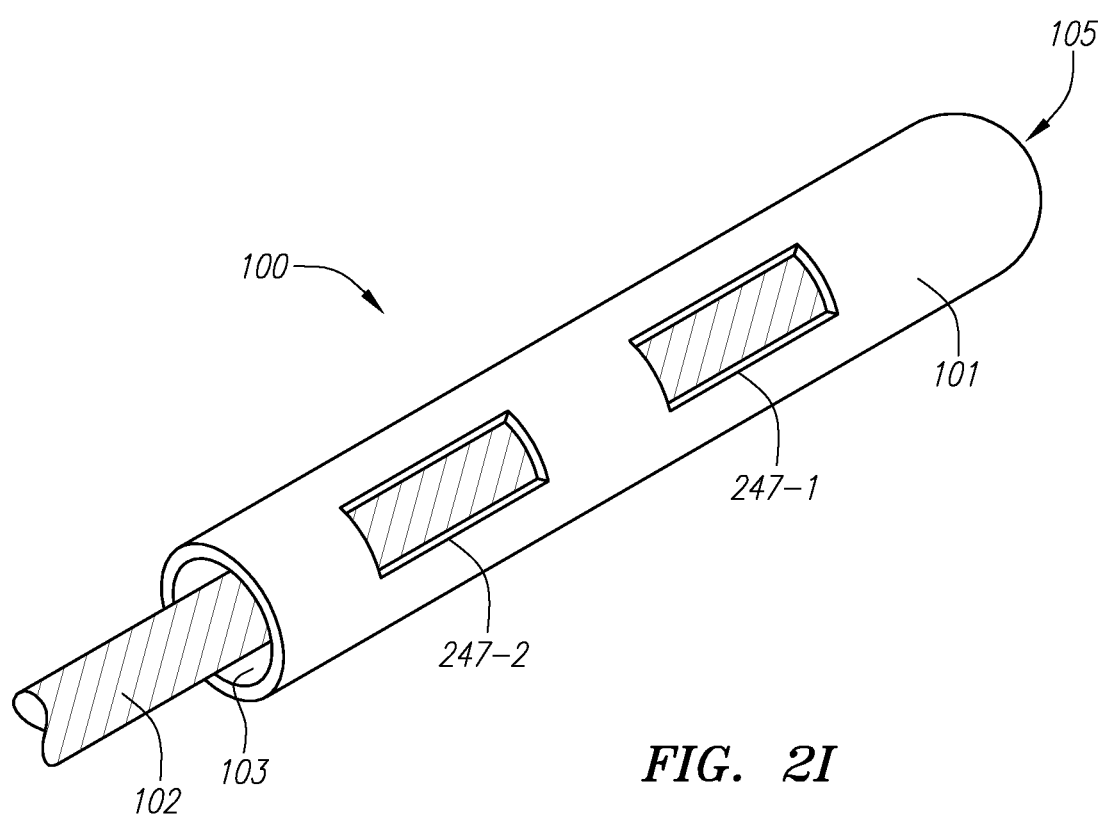

FIG. 2I is a perspective view of an example embodiment of system 100 where sleeve 101 includes longitudinal slots, or cutouts, 247-1 and 247-2, which are configured to allow sleeve 101 and rod 102 to fit closely with the adjacent spinous processes. Here, only a portion of sleeve 101 is depicted. Slots 247-1 and 247-2 are positioned according to the location of the spinous processes of the portion of the patient's spinal column to be treated. Each spinous process is received within the respective slot 247, allowing rod 102 to be positioned relatively closer to the spinous process. This can be desirable in applications where close placement of rod 102 to the spinous process is desired for increased accuracy or precision in the application of the corrective force. Also, the close proximity of sleeves 101 and rods 102 to the surface of the vertebrae minimizes the stress placed on the attachment device. This embodiment of sleeve 101 is particularly suited to use with attachment devices such as those embodiments described with respect to FIGS. 5H-L, although not limited to such. It should be noted that instead of multiple slots 247, only one continuous slot can be present to more freely allow sleeve 101 to slide back and forth across spinous processes 14, if desired.

FIG. 2J is a perspective view of another example embodiment of spinal correction system 100 where tubular members 101-2 and 101-4 are coupled together by connective portion 115, which is routed through iatrogenic opening 110 in spinous process 14. Here, a separate spinal coupling device (e.g., coupling device 109) can be omitted since the functionality is integrated into tubular members 101 themselves. To achieve the configuration depicted here, tubular members 101 are preferably flexible enough to allow distortion while the tubular member is passed or threaded through opening 110. The attachment to spinous process 14 preferably occurs at a superiorly located as an inferiorly located position. Again, sleeves 101 are preferably formed from a polymeric material such as polyethylene (PE), polyetheretherketone (PEEK), polytetrafluoroethylene, fluorinated ethylene/propylene copolymers, silicones, hydrogels, hydrophilic coatings, polyurethane (PU), and the like.

Although spinal correction system 100 preferably includes sleeves 101 for attachment to spinal column 10, it should be understood that rods 102 can be directly attached to spinal column 10 with the omission of sleeves 101 altogether. Embodiments of system 100 that attach to spinal column 10 without reliance on sleeves 101 are described in the parent U.S. patent application Ser. No. 11/656,314 and entitled "Orthosis to Correct Spinal Deformities," which is fully incorporated by reference herein.

It should be noted that any number of corrective systems 100 can be coupled to spinal column 10 at multiple locations along the length of spinal column 10. The use of multiple systems 100 allows relatively more localized correction. Different systems 100 can be configured to apply different degrees of corrective force in different directions and can be placed contiguously, or at spaced apart locations on spinal column 10 leaving vertebral bodies 11 to which no corrective force is applied. For example, if a spinal deformity bridged multiple regions (cervical and thoracic, thoracic and lumbar, all three regions, etc.) of the spinal column, then different systems 100 could each be targeted to treat those different regions of the spinal column.

The use of multiple systems 100 can allow greater freedom of movement to the patient. Also, in the case where the systems 100 are placed in a partially overlapping manner, less additional length of each sleeve 101 and rod 102 is required in the regions extending past the most superiorly and inferiorly located vertebral bodies to be treated since extra length needed to accommodate full range of motion and growth over time is distributed among the multiple systems 100. Also, corrective systems 100 can be made to overlap such that two sets of rods 102 can apply different amounts of corrective forces in different directions on the region of the spine in the overlapping portion. Furthermore, the use of multiple corrective systems 100 can facilitate implantation and replacement, depending on the anatomy and the desired strategy for correction. For instance, with multiple systems 100, replacement can be limited to only the necessary components to achieve the desired correction.

In addition, more than one rod can be used along a single side of the spinal column, either coupled directly to the spinal column or placed within or through a sleeve 101. FIG. 11 of the incorporated application Ser. No. 11/656,314 depicts an example of a multiple rod configuration where each rod is slidable with respect to the other. This allows two rods of varying stiffness to be used as well as allowing the rods to change length during flexion or extension of the patient's spine.

Figure 3A:
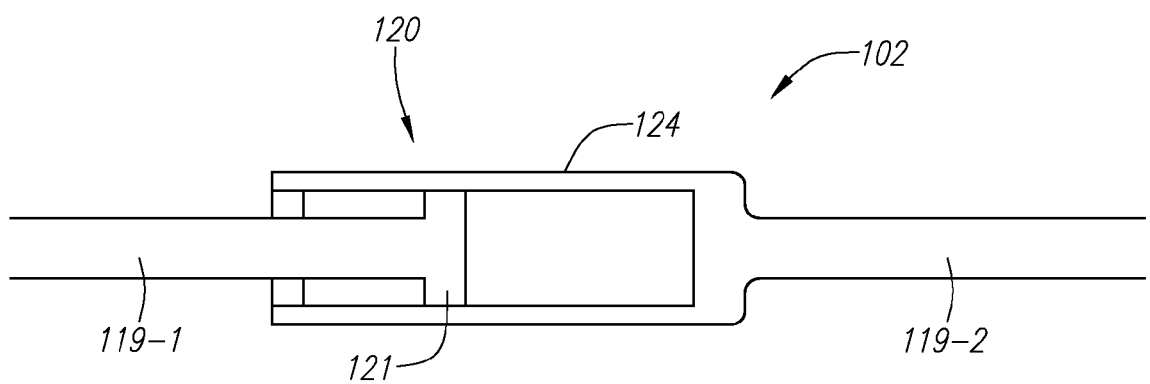
FIGS. 3A-B are cross-sectional views depicting example embodiments of a rod for a spinal correction system.
Figure 3B:
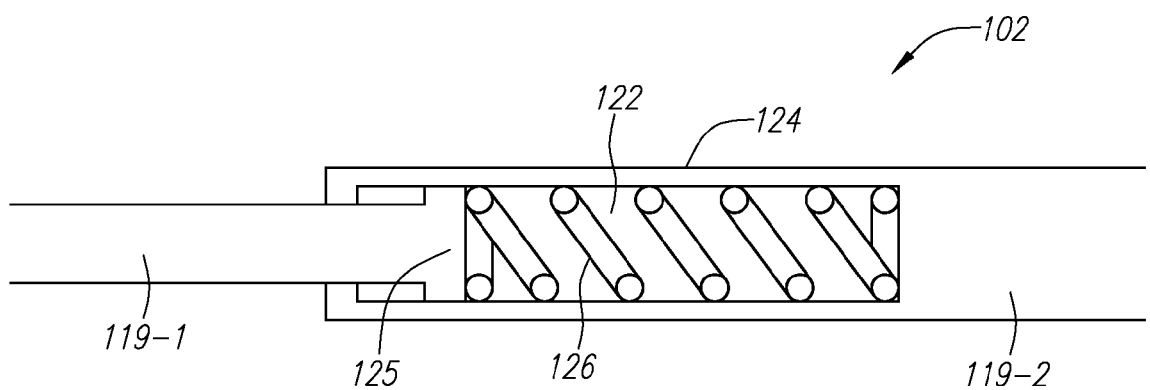

Alternatively, FIGS. 3A-B included herein depict an example embodiment of a telescoping rod 102 for use in system 100. FIG. 3A is a cross-sectional view showing an example embodiment of rod 102. Here, rod 102 includes a first rod segment 119-1 and a second rod segment 119-2 with a piston portion 120 located therebetween. Rod 119-2 includes a hollow portion having a side wall 124 configured to receive rod 119-1. The hollow portion has a sealing member 123, such as a gasket, that is configured to encompass rod 119-1 and guide its movement into the hollow portion. Rod 119-1 includes a sealing member 121 configured to compress the volume located within region 122 in a piston-like manner. Depending on the substance filling the volume of region 122, the amount of force necessary to compress rods 119-1 and 119-2 toward each other can be varied.

FIG. 3B is a cross-sectional view depicting another example embodiment similar to that of FIG. 3A. Here, rod 119-1 has an enlarged end 125 that is configured to compress a bias element 126 located within chamber 122. In this embodiment, the volume within chamber 122 does not need to be compressed since the biasing is provided by bias element 126. Bias element 126 can be any compressible and expandable structure. Here, bias element 126 is configured as a spring.

Figure 3C:
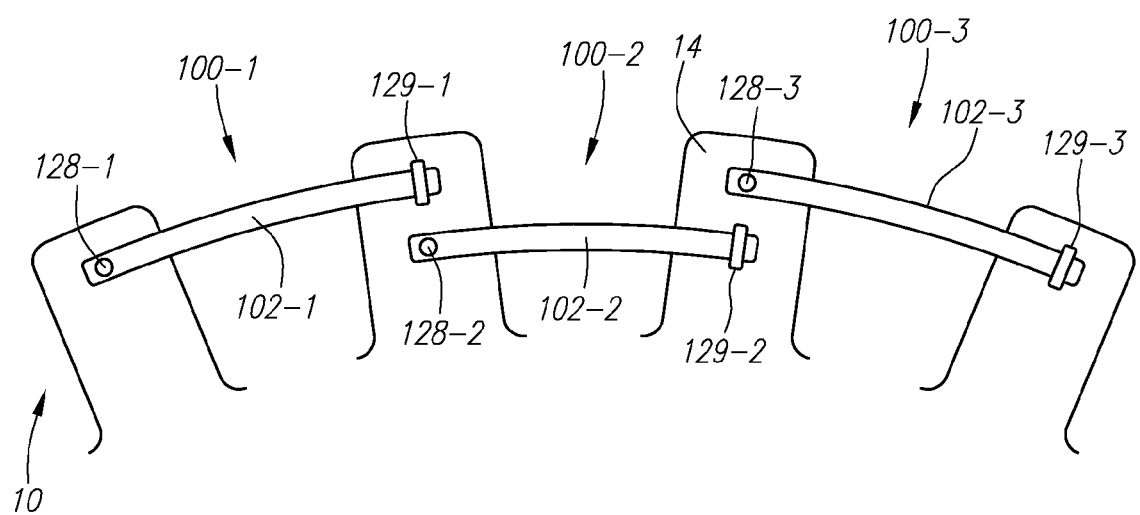
FIG. 3C is a side view depicting an example embodiment of a spinal correction system implanted within a patient.

FIG. 3C shows an example embodiment where three systems 100-1, 100-2 and 100-3, each having a rod 102-1, 102-2 and 102-3, respectively, are coupled in series along patient's spinal column 10. Here, spinal column 10 is shown in full flexion. Each rod 102 has a fixed connector 128 that fixedly connects the rod to a first spinous process 14. Each rod can also have one or more slidable connectors 129 to one or more adjacent spinous processes 14 (only one slidable connector 129 per rod 102 shown here). Slidable connector 129 allows rod 102 to slide in relation to the spinous process 14 to which the slidable connector 129 is attached. Example slidable connectors are described herein as well as in the incorporated parent application.

Turning now to the attachment of spinal correction 100 to the spinal column, various methods and devices for attachment are disclosed in the incorporated parent application. These include U-shaped clamps that are fixedly screwed to the spinous process, such as that described with respect to FIG. 2 of the parent application. Also disclosed are opposing plate-like devices that are screwed through the spinous process and include textured or spiked surfaces that increase friction with the underlying bone, such as that described with respect to FIG. 5 of the parent application.

Additional attachment devices are provided herein having various configurations and methods of attachment. It should be noted that any of these devices can be fixedly screwed to the patient's spinal column and can take advantage of the use of textured surfaces or spiked surfaces such as described in the parent application. Accordingly, those structures and methods of attachment will not be repeated.

As will be discussed in more detail herein, attachment to the patient's spinal column preferably occurs in a minimally invasive manner to limit the amount of exposure of each vertebral body attached to the spinal correction system. In a preferred embodiment, the spinous process is the only portion of those vertebral bodies in the region to be treated that is exposed during surgery. Preferably, no tissue anterior to the base of the spinous process is dissected and exposure of the laminae and facet joints is avoided. This can prevent undesirable secondary effects (e.g., excessive blood loss, scarring, auto-fusion).

In another embodiment, the spinous process is exposed without dissecting any portion of the ligamentum flavum coupled with the vertebral body to which the spinal correction system is coupled. In yet another embodiment, the spinous process is exposed without exposing any portion of each lamina anterior to the flaring transitional region of that lamina. While in yet another embodiment, only the portion of the spinous process posterior to the flaring transitions is exposed. Each of these embodiments will, among other things, reduce the scarring that will occur on or near the vertebral body of the patient. Accordingly, many of the embodiments of attachment devices described herein are configured to engage only the spinous process of each vertebral body, preferably, posterior to the flaring transitional regions of the spinous process and the laminae (although these devices can be configured to attach to other portions of the vertebral body if desired).

FIGS. 4A-B are perspective views of example embodiments of an attachment device 201. Attachment device 201 can be used to couple any portion of corrective system 100 to the patient's spinal column 10, preferably the spinous process 14. For instance, attachment device 201 can be used to couple one or more of tubular members 101 or flexible rods 102

(neither shown) to spinous process 14. Also, attachment device 201 can be used to couple any other portion of corrective system 100 to spinous process 14, such as coupling devices 106, 108 or 109 (also not shown).

Here, attachment device 201 is generally U-shaped and includes a first plate-like side portion 202 and a second plate-like side portion 204 coupled together by an end portion 203. Plate-like side portions 202 and 204 oppose each other and are configured to attach to opposing sides of spinous process 14. Plate-like side portions (or plates) 202 and 204 can be generally flat, or can have a relatively slight degree of curvature. In FIG. 4A, end portion 203 is placed over the posterior side 27 of spinous process 14, and in FIG. 4B, end portion 203 is placed over either the superior or inferior side of spinous process 14. Located on each plate-like side portion 202 and 204 is an engagement feature 205, which in this embodiment includes a raised portion 206 having a threaded lumen 207 therein. Engagement feature 205 can be configured in any manner desired to engage or interlock with the designated portion of spinal correction system 100 (e.g., sleeve 101, rod 102, coupling device 109, etc.).

Attachment device 201 can be attached to spinous process 14 using numerous different methods. For instance, attachment device 201 can be advanced over spinous process 14 and crimped onto spinous process 14 using a crimping tool. In this regard, attachment device 201 is preferably formed from a crimpable material such as nitinol, stainless steel, various rigid polymers and the like. Additional embodiments of attachment device 201 configured to be attached to the spinous process are described in FIGS. 5A-12B.

Attachment device 201 can also be configured to be self-adjusting to attach with spinous process 14, as will be described with respect to FIGS. 4C-E, 5A, 5D, 5F and 11A-D. FIGS. 4C-E depict an example embodiment of attachment device 201 where platelike portions 202 and 204 are biased toward each other. FIG. 4C is a top-down view of this embodiment in an at-rest state where plate-like portions 202 and 204 are in close proximity to each other. Attachment device 201, in this embodiment, is preferably formed from an elastic material, such as spring steel, or a superelastic, shape-memory material, such as nitinol, and biased toward the at-rest state depicted in FIG. 4C. In addition, attachment device 201 can be formed from a polymeric material with attached or integral metallic components configured to apply the bias.

Attachment device 201 can then be deformed or deflected from this at-rest state to an open state such as that depicted in the top-down view of FIG. 4D. In this deflected state, attachment device 201 can be advanced over spinous process 14 and released. Once released, plate-like portions 202 and 204 deflect toward the at-rest state and exert a clamping force on spinous process 14 as depicted in FIG. 4E. Advancement and release of attachment device 201 can be facilitated with a delivery device (not shown).

Alternatively, attachment device 201 can be configured with thermally dependent shape-memory characteristics. Configuration of nitinol to exhibit thermally dependent shape-memory characteristics is well known in the art and will not be discussed herein. Generally, in such an embodiment, attachment device 201, at room temperature (or cooler), would be deformed to a state similar to that depicted in FIG. 4D and would exhibit only a minimal, if any, bias toward a separate state. Once in place over spinous process 14, attachment device 201 can be deformed to place plate-like portions 202 and 204 into contact with the opposing sides of spinous process 14. After implantation, the patient's body heats attachment device 201 and this heating activates the shape-memory characteristics to cause attachment device 201 to exhibit a bias toward a state similar to that depicted in FIG. 4C, thereby causing attachment device 201 to clamp onto spinous process 14.

It should be noted that the use of adhesives, preferably quick-drying adhesives, can also be used to facilitate engagement of attachment device 212 to spinous process 14. In FIG. 4D, a quick-drying resin 208 is placed on the inner surface of plate-like portions 202 and 204. Adhesive 208 can be applied by the medical professional to the interior of plate-like portions 202 and 204 prior to the implantation procedure or can be pre-placed on portions 202 and 204 by a third party (e.g., the manufacturer). Alternatively, or in addition to placement on the inner surfaces of device 201, adhesive 208 can be applied to spinous process 14 by the medical professional prior to implantation of attachment device 201.

Figure 4F:
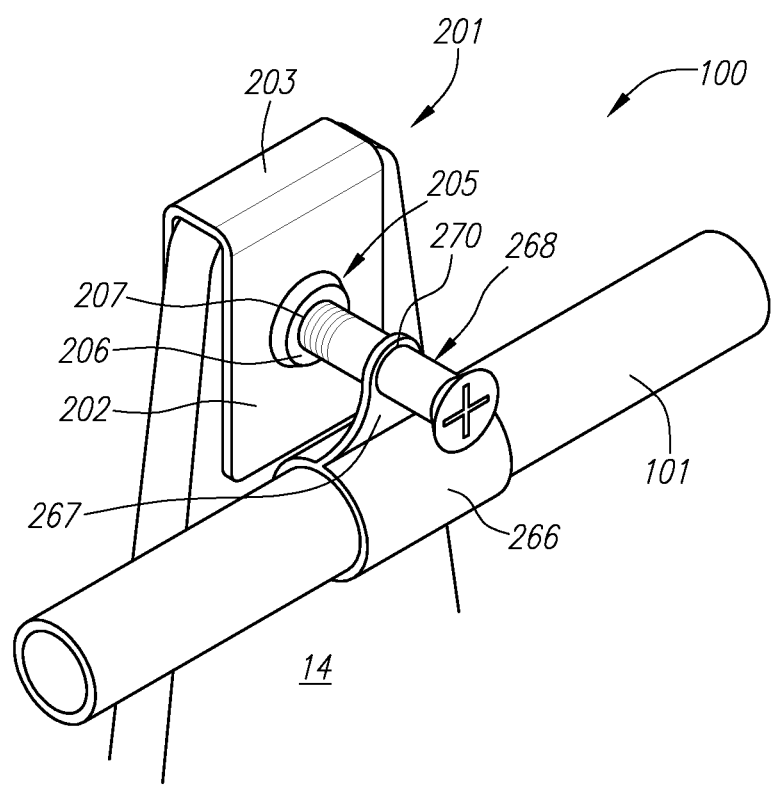
FIG. 4F is a perspective view depicting an example embodiment of a spinal correction system implanted within a patient.

FIG. 4F is a perspective view of an example embodiment of spinal correction system 100 attached to spinous process 14 by way of attachment device 201 and engagement feature 205 having threaded lumen 207. Here, sleeve 101 is received within an outer tubular member 266 which can be either slidably or fixedly coupled to an outwardly extending strut 267 having an aperture 270 therein. Aperture 270 is preferably aligned with lumen 207 in engagement feature 205 such that a screw 268 can be inserted through aperture 270 and into threaded lumen 207. Screw 268 is tightened until enlarged head portion 269 of screw 268 contacts strut 267 and provides the desired amount of fastening.

One of skill in the art will readily recognize, based on the description provided herein, that numerous types of engagement features 205 configured for many different types of attachment can be provided including, but not limited to, threaded (e.g., screw) features, latch features, snapable features, hookable features, crimpable features, clampable features, features for wired attachment, features to facilitate attachment with adhesives, and the like.

In another example embodiment, the surface of the spinous process can be modified to create recesses in which the attachment device 201 can be seated. For instance, with a U-shaped attachment device, a U-shaped chisel can be used to create grooves or slots on either face of the spinous process. The grooves could be sized to receive the entire attachment device, or could complement keels or spikes on the inner surface of the portions 202 and 204. Portions 202 and 204 can then be tapped onto the spinous processes to anchor the keels or spikes into the grooves.

FIGS. 5A-F depict additional example embodiments of attachment device 201 where device 201 is configured to surround the periphery of spinous process 14. One advantage of these configurations is that the devices 201 can be introduced laterally as opposed to posteriorly, which lessens the disruption and dissection of the interspinous ligament. An engagement feature 205 is shown on the near side of the spinous process 14 in FIGS. 5A-E, and can also be included on the opposite side as well. In the perspective view of FIG. 5A, attachment device 201 includes an elastic band 210 with a relatively more rigid section 211 thereon. Engagement feature 205 is located on rigid section 211, both of which can also be present on the opposite side of spinous process 14. Elastic band 210 is preferably composed of a biocompatible, polymeric material having sufficient life span to retain its structural integrity and elasticity over the duration of implantation, such as silicone or polyurethane, and the like.

FIG. 5B is a perspective view of another example embodiment of attachment device 201 where device 201 includes a strap-like member 212 having a first end 213 configured to slide into and be received by an opposing, second end 215 having a lumen therein. End 213 preferably includes engageable elements 214, which in this case are ribs or ridges in the surface of strap 212. Engageable elements 214 are preferably configured to interface with an opposing feature within end 215, such that a tightening motion is allowed, but the reverse motion (un-tightening) is prevented by the opposing features. The embodiment can operate in a "zip-tie" fashion, that is, the user advances end 213 through end 215, continually passing engageable elements 214 through end 215 until the desired tightness or compressive force is exerted, at which point reverse motion is prevented. Here, engagement feature 205 is located on the outer surface of end 215. Alternatively, strap 212 can be made of woven fibers made from polymers such as polytetrafluoroethylene (PTFE), polyethylene ptherethalate (PET) or ultrahigh molecular weight polyethylene (UHMWPE) or metal filaments such as nitinol, stainless steel, titanium alloys, and the like. The engagement feature 205 could be configured as a buckle.

In the perspective view of FIG. 5C, attachment device 201 includes a flexible band 218 having opposing ends that are coupled together by a crimpable structure 219. Here, band 218 is placed over spinous process 14 with the desired amount of tension or compressive force, and crimpable structure 219 is then crimped over the ends to fasten them with relation to each other. Instead of a crimpable structure, a clamp, a snap or the like can also be used. In addition, self-tightening fasteners can be used. Alternatively, crimpable structure 219 can have two lumens to accommodate either end of the flexible band.

In the perspective view of FIG. 5D, engagement feature 205 is located on a plate-like base 220. Base 220 is maintained in place on spinous process 14 by a compressible coil 221. Adhesives can be used to facilitate the attachment of plate-like base 220 to spinous process 14 as well. Coil 221 is preferably deformed from a relatively smaller state around spinous process 14 such that it continues to exert a significant compressive force to hold plate-like base 220 in place. Base plate 2220 can also include features to facilitate attachment or placement of coil 221, such as eyelets, hooks, guides, recesses, and the like. Coil 221 can be formed from any elastic material including but not limited to nitinol, stainless steel, polymers, elgiloy, and the like.

Figure 5E:
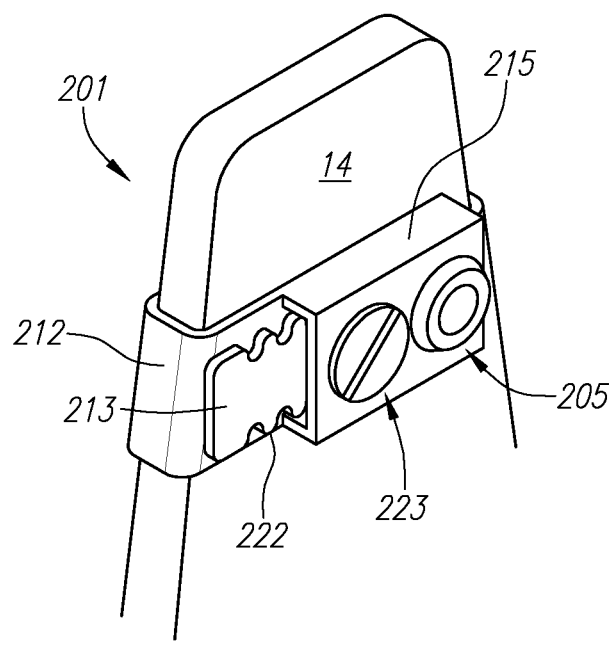

In the perspective view of FIG. 5E, attachment device 201 again includes a strap or band 212 having ends 213 and 215, with end 215 configured to receive end 213 within an inner lumen. End 213 preferably includes ridged or otherwise ratchetable elements 222, which are configured to operate with a ratchet 223 located on and within end 215. Here, ratchet (or screw drive) 223 is configured to be turned (either in a clockwise or counterclockwise fashion) to increase or decrease the tension on strap 212 by interfacing with ratchetable elements 222. Again, engagement feature 205 is located on end 215. In an alternative embodiment, attachment device 201 can be configured such that ratchetable elements 222 are grooves or holes in the center of band 212, as opposed to ridges on the edge of each band 212. In the embodiments of FIGS. 5B and 5E, an opposing engagement feature 205 can be placed directly on strap 212 on the opposite side of spinous process 14.

Figure 5F:
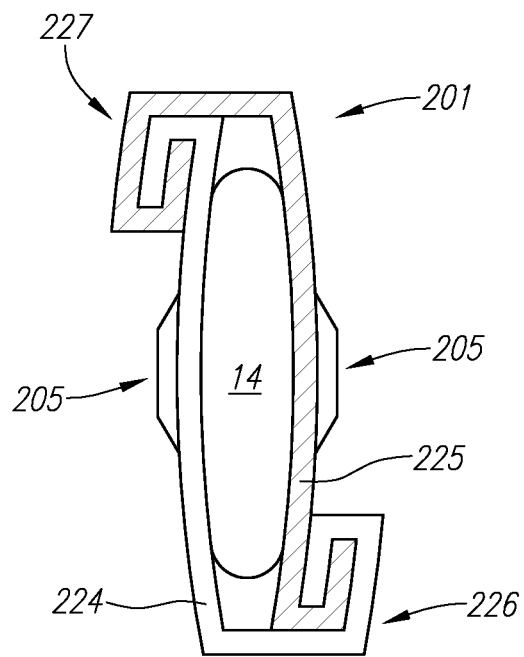
FIG. 5F is a posterior view depicting an example embodiment of an attachment device.

FIG. 5F is a posterior view of another embodiment of attachment device 201 located on spinous process 14. Here, attachment device 201 includes two bodies 224 and 225, each having plate-like portions configured to oppose each other, as well as interlocking features 226 and 227 on the opposing ends. Here, each interlocking feature 226 and 227 is formed by complimentary hook-like features on each body 224 and 225. These features are preferably configured to maintain attachment device 201 in place over spinous process 14 by inducing deflection in bodies 224 and 225 to compress the spinous process 14 located therebetween. Alternatively, bodies 224 and 225 can be threaded or perforated at one end so compression is achieved by tightening a screw or other adjustable device disposed through both bodies 224 and 225.

Figure 5G:
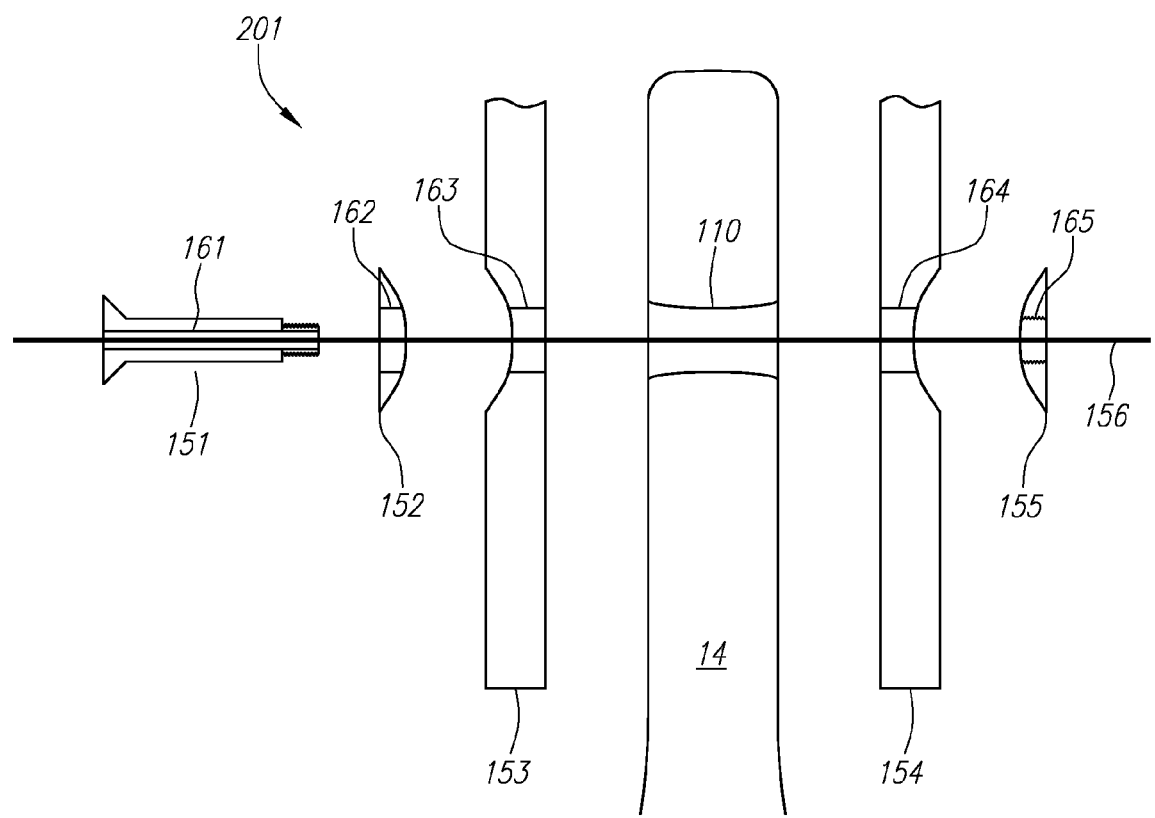
FIG. 5G is an exploded cross-sectional view depicting an example embodiment of an attachment device.

FIG. 5G is an exploded cross-sectional view depicting another example embodiment of an attachment device 201, including cannulated elements configured to be positioned over a guidewire 156. Specifically, opposing plates 153 and 154, both having lumens 163 and 164, respectively, are positioned on opposing sides of spinous process 14, having iatrogenic opening 110, which in this embodiment need only be large enough to allow passage of guidewire 156 therethrough. Guide elements 152 and 155 have a washer-like configuration and are placed over plates 153 and 154, respectively, with the aid of guidewire 156. A coupling device 151, which is configured as a screw having lumen 161, is then advanced over guidewire 156 and through lumens 162 and 165 of guide elements 152 and 155, respectively. Lumens 162 and 165 are preferably configured to closely fit screw 151, which is also advanced through lumens 163 and 164 as well as opening 110. Lumen 165 of guide element 155 is preferably threaded to lockingly receive screw 151.

Guide elements 152 and 155 are preferably configured to allow angulation of screw 151 with respect to plates 153 and 154 when the components are routed over guidewire 156. In this embodiment, guide elements 152 and 155 have a convex surface configured to interface with a concave surface in each of plates 153 and 154, respectively, to permit variations in angulation, which can occur due to the variability in anatomy of spinous processes 14.

Alternatively, a variation of this embodiment can be used in the gap between adjacent spinous processes such that plates 153 and 154 compress against both sides of either or both of the superior and inferior spinous processes. Preferably, the width of coupling device 151 is small enough that it does not contact the opposing surfaces of the spinous processes above and below.

Figure 5H:
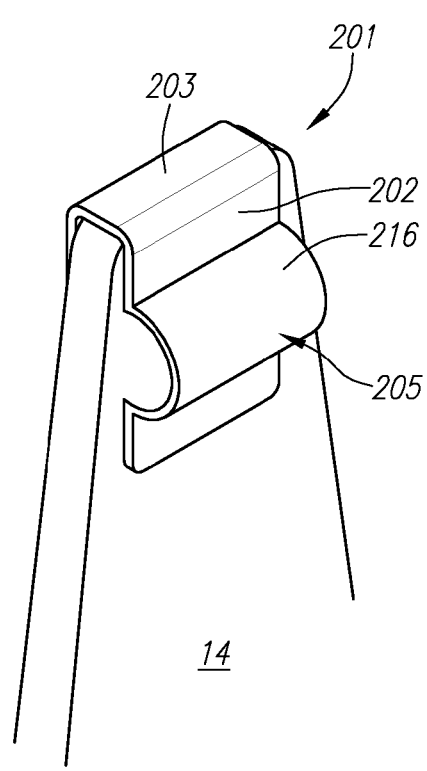
FIGS. 5H-L are perspective views depicting additional example embodiments of attachment devices.
Figure 5I:
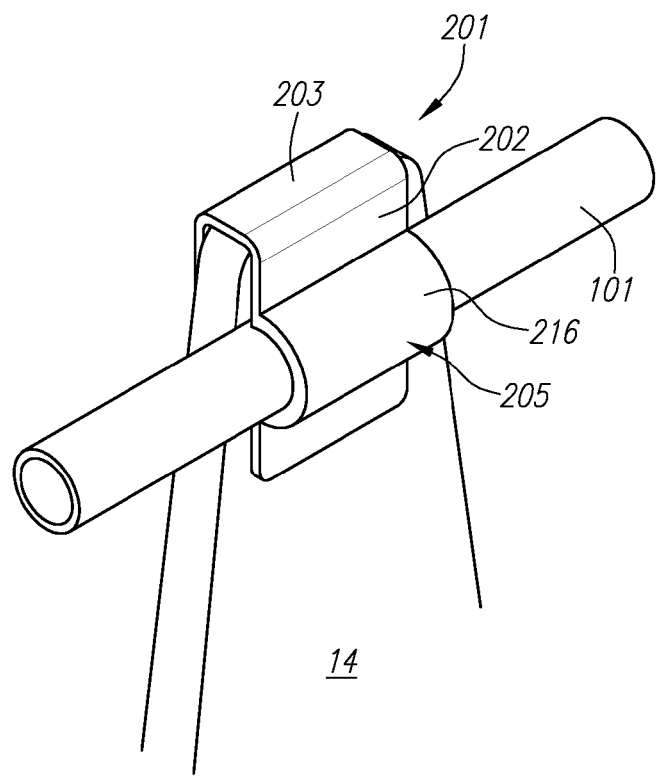
Figure 5J:
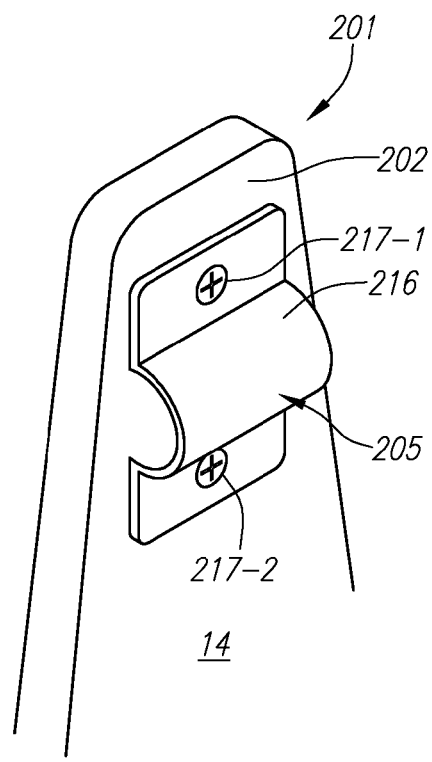
Figure 5K:
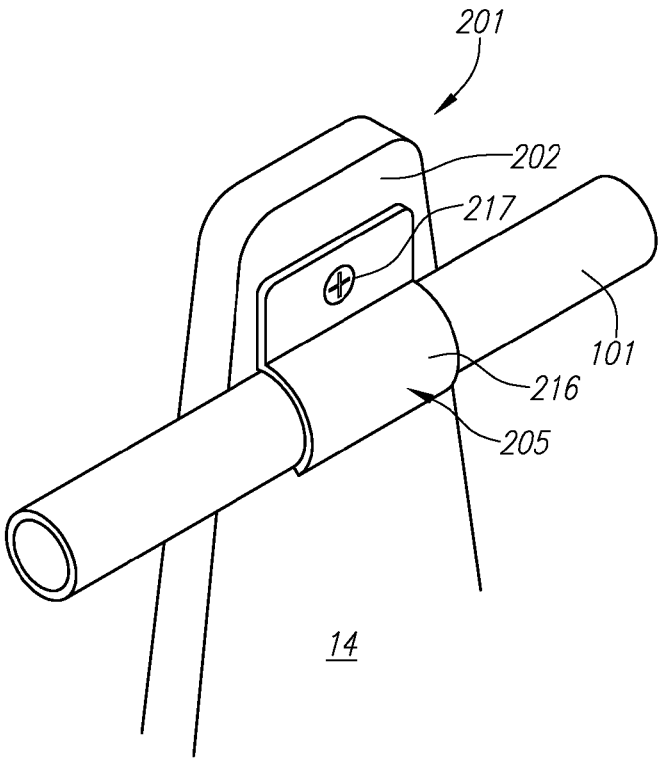

FIGS. 5H-L are perspective views depicting additional example embodiments of attachment devices 201, where each embodiment allows sleeve 101 and/or rod 102 (not shown) to be positioned relatively closer to the spinous process. FIG. 5H depicts an example embodiment of attachment device 201 configured as a U-shaped clamp having an engagement feature 205 configured as a raised portion 216 offset from spinous process 14 to create a lumen therein. FIG. 5I depicts this embodiment with sleeve 101 contained beneath raised portion 216. FIG. 5J depicts a similar embodiment, except that attachment device 201 has a plate-like configuration and is fixed to spinous process 14 with screws 217-1 and 217-2. FIG. 5K depicts an example embodiment where raised portion 216 only partially encompasses sleeve 101.

Figure 5L:
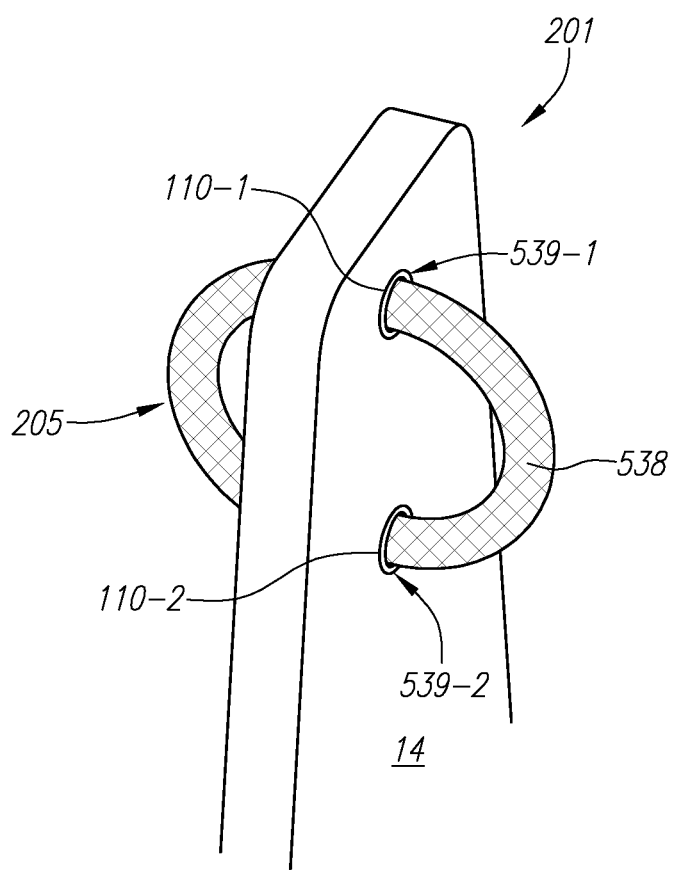

FIG. 5L depicts an example embodiment where attachment device 201 includes an engagement feature 205 formed by a tether 538 routed through two iatrogenic openings 110-1 and 110-2 in the spinous process 14. Each iatrogenic opening 110-1 and 110-2 is lined by a grommet-like structure 539-1 and 539-2, respectively, to allow for reduced friction as tether 538 passes therethrough. Tether 538 can be a monofilament or a braided structure as shown here. Tether 538 is preferably formed from a biocompatible material including, but not limited to, nitinol, stainless steel, polymeric materials, and the like.

Figure 6A:
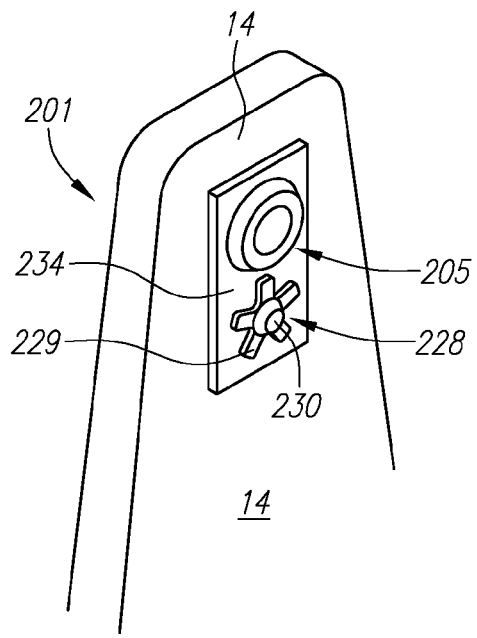
FIG. 6A is a perspective view depicting an example embodiment of an attachment device.
Figure 6B:
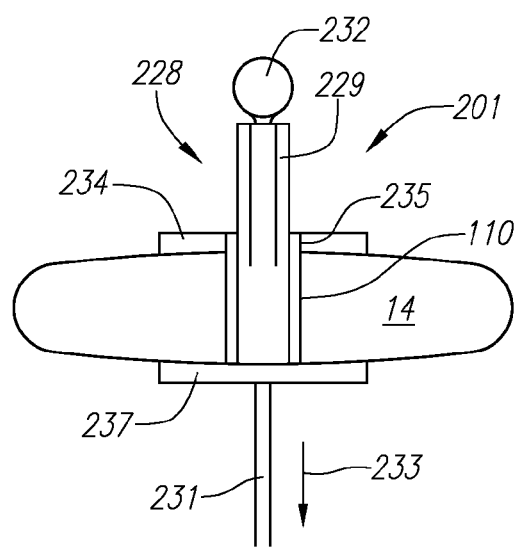
FIGS. 6B-C are cross-sectional views depicting stages of implantation of an example embodiment of an attachment device.
Figure 6C:
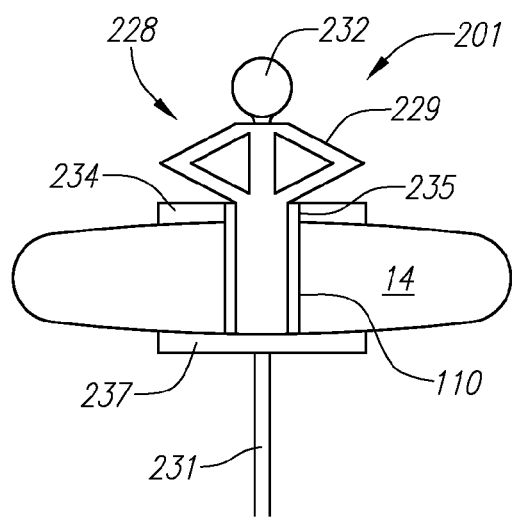

FIGS. 6A-C depict another example embodiment of attachment device 201, where an expandable rivet-like structure is used to attach a plate-like base 234 to the spinous process 14. FIG. 6A is a perspective view showing an example embodiment of expandable rivet 228 having a central lumen 230 and a plurality of bent struts 229 extending out over plate-like base 234. FIGS. 6B-C are partial cross-sectional views showing a method of deployment of this embodiment of device 201.

An iatrogenic opening 110 in spinous process 14 is first formed to allow passage of device 201 therethrough. Attachment device 201 includes a second plate-like base 237 coupled with rivet 228 having a plurality of slots located therein, the portions of rivet 228 between slots forming struts 229. A pull rod 231 is placed within lumen 230 (not shown in FIGS. 6B-C). Pull rod 231 has an enlarged portion 232 at its distal end to abut with rivet 228. Plate-like base 234 has a lumen 235 and is placed over iatrogenic opening 110 with rivet 228 routed therethrough. Pull rod 231 is pulled proximally while applying a force on base 237 to maintain the apparatus in place.

The result is shown in FIG. 6C, where the proximal force has caused struts 229 to deflect outwards into a rivet-like configuration and engage plate-like base 234, thereby coupling base 234 and base 237 to the opposing sides of spinous process 14. Pull rod 231 can then be removed by advancing distally in a direction opposite to direction 233. Although not shown in FIGS. 6B-C, each base 234 and 237 preferably includes engagement feature 205 for coupling to corrective system 100.

In another embodiment, pull rod 231 can be omitted and rivet 228 can be expanded by applying compressive force to both sides of device 201 on process 14 with an externally located tool. In yet another example embodiment, rivet-like structures 228 can be coupled on both sides of the spinous process. It should also be noted that this embodiment can be positioned in the space between adjacent spinous processes.

Figure 7D:
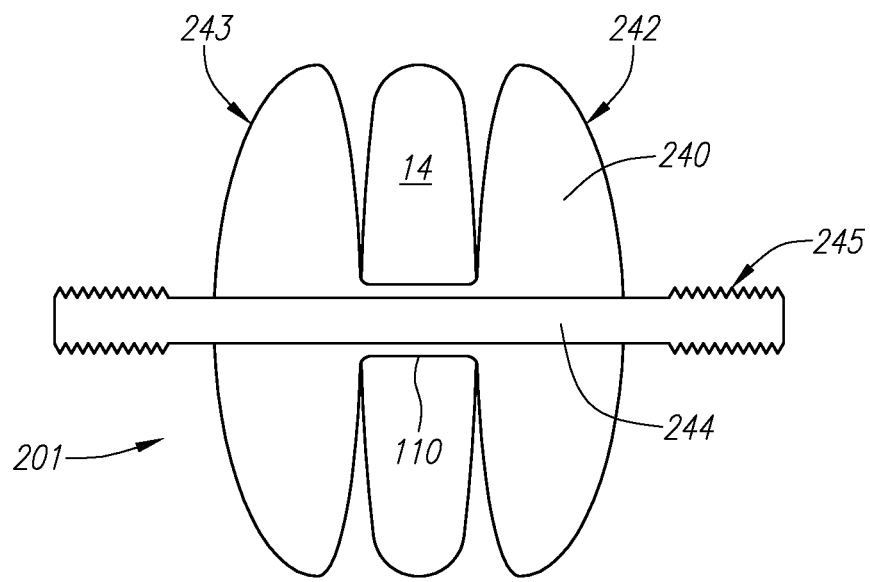
FIGS. 7D-E are cross-sectional views depicting example embodiments of attachment devices.

FIGS. 7A-E depict additional example embodiments of an attachment mechanism 201 for coupling with spinous process 14. FIG. 7A is a perspective view showing iatrogenic opening 110 through spinous process 14. An inflatable member 240, such as a flexible bag, balloon and the like, is provided with an optional inflation port 241. Balloon 240 is threaded through opening 110 as depicted in FIG. 7B. This can be performed manually or with the aid of a guidewire routed through opening 110. An inflation medium is then inserted into balloon 240 through inflation port 241. If no port is provided, the inflation medium can be injected directly through the wall of balloon 240. This inflation medium is preferably a cement or resin or other liquid that will harden over time, although gels and other viscous, semi-rigid, non-hardening materials can be used. Examples, of suitable hardening substances include, but are not limited to, methyl-methacrylate (MMA), polymethyl methacrylate (PMMA), epoxy resins, calcium phosphate, and the like.

Figure 7E:
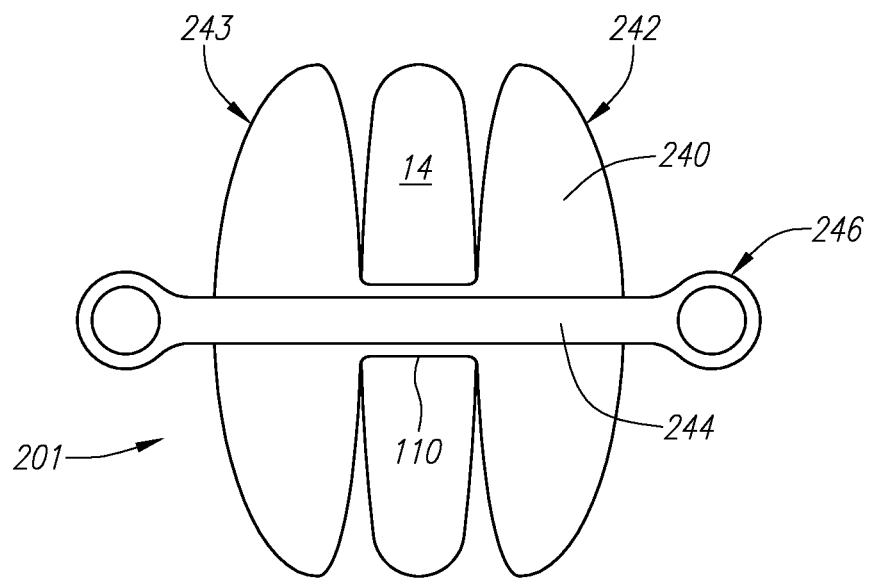

Once inflated, balloon 240 forms anchor portions 242 and 243 on opposite sides of spinous process 14 as depicted in FIG. 7C. These anchor portions 242 and 243 can then be relied upon as a basis for coupling to spinous process 14. Balloon 240, among other things, conforms to the surface profile of the spinous process 14, distributing force evenly and eliminating or reducing the potential of stress risers. FIGS. 7D-E are cross-sectional views depicting two example embodiments of a through-rod 244 inserted through opening 110 and balloon 240. Through-rod 244 preferably includes engagement features on each opposing end to facilitate engagement of spinal correction system 100 to spinous process 14. Here, the engagement features of through-rod 244 are threaded portions 245 on either end (as depicted in FIG. 7B) or enlarged portions 246 having an eyelet (such as that depicted in FIG. 7E).

Through-rod 244 can be inserted into this configuration in several ways. Balloon 240 can be provided with a through-aperture (not shown) through which rod 244 can be inserted either before or after curing of the resin. If a through-aperture is present, it can also be used for threading balloon 240 through iatrogenic opening 110 prior to inflation. Alternatively, through-rod 244 can be inserted through balloon 240 and the resin therein prior to full curing of that resin. Or, after curing, a through-aperture can be drilled by the user to create the opening in which to insert through rod 244. Based on this description herein, one of skill in the art will readily recognize that there are other methods of inserting through-rod 244 that can also be used. Instead of inserting through-rod 244 after inflation, balloon 240 can have through-rod coupled thereto prior to threading through opening 110.

Figure 8A:
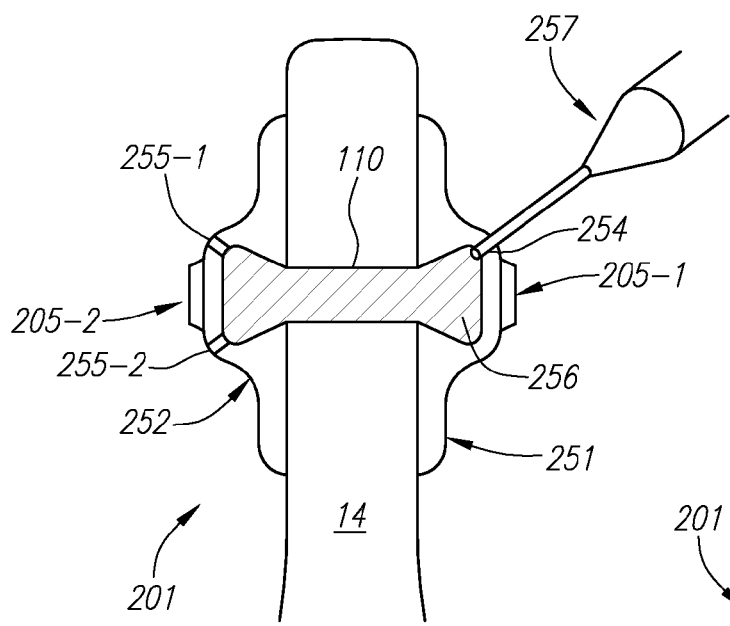
FIGS. 8A-B are cross-sectional views depicting stages of implantation of an example embodiment of an attachment device.
Figure 8B:
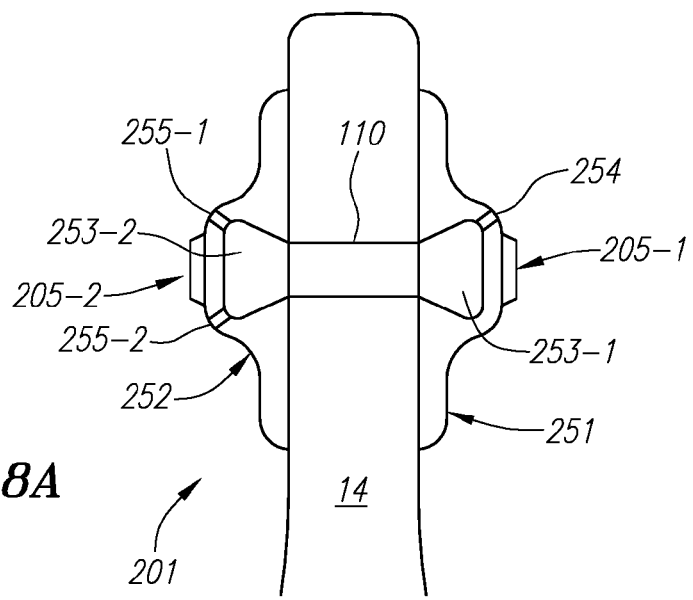

FIGS. 8A-B are cross-sectional views depicting another example embodiment of attachment device 201, where attachment is made by filling iatrogenic opening 110 with a cement or resin. Preferably, this embodiment of device 201 includes a first side plate 251 and a second side plate 252 configured to interface with opposing sides of spinous process 14. Each plate 251 and 252 includes an internal chamber 253, which is preferably configured to form an anchor once filled with the cement or resin. Here, chamber 253 has a width that is tapered or stepped to provide resistance to detachment once filled with the cement or resin.

Plate 251 preferably includes an injection port 254 that communicates with chamber 253-1. Chamber 253-1 has an open end that is alignable with iatrogenic opening 110. Likewise, plate 252 includes an inner chamber 253-2 with an opening that is alignable with iatrogenic opening 110. Plate 252 also includes one or more (in this example, two) vent holes 255 that allow venting during injection of the cement or resin. Both plates 251 and 252 can include one or more engagement features 205 as well.

FIG. 8B depicts engagement device 201 after injection of resin 256 into chamber 253-1, opening 110 and chamber 253-2 by an injector 257. Injector 257 can then be removed. Plates 251 and 252 are preferably held in place until the cement or resin has cured sufficiently to lock plates 251 and 252 in place on spinous process 14. Again, examples of cements or resins can include methyl methacrylate (MMA), polymethyl methacrylate (PMMA), epoxy resins, calcium phosphate, and the like.

Figure 9:
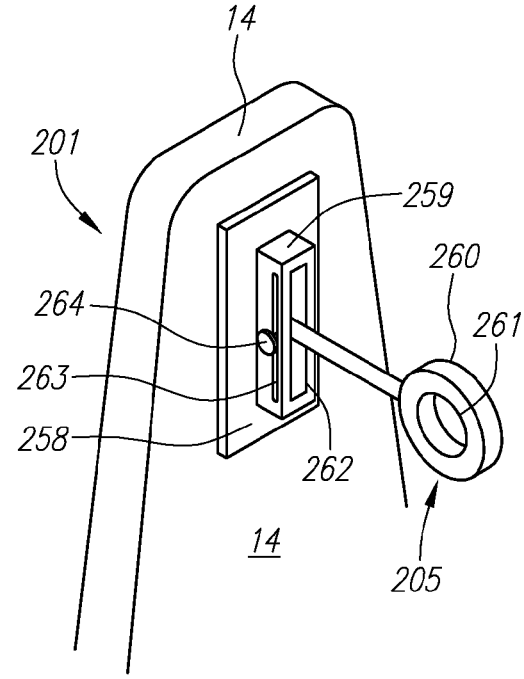
FIG. 9 is a perspective view depicting an example embodiment of an attachment device.

FIG. 9 is a perspective view of another example embodiment of attachment device 201 where the position of engagement feature 205 is adjustable. Here, adjustability is provided posteriorly and anteriorly (up and down as depicted here), but superior and inferior adjustment can also be provided as well as height adjustment from the surface of spinous process 14. Attachment device 201 includes a base 258 coupled with spinous process 14.

Base 258 preferably includes a housing 259 in which an elongate member 260 is connected and allowed to slide both posteriorly and anteriorly. Elongate member 260 includes an eyelet 261 for receiving rod 102 (not shown). It should be understood that elongate structure 260 can take any configuration and be configured to couple with any portion of corrective system 100, not limited to rod 102.

Once properly positioned, elongate structure 260 is fastened in place by a fastening device, such as set screw 264, which, in this embodiment, is allowed to slide with structure 260 through slot 263 in the side of housing 259. The ability to adjust position in this manner is beneficial in that it allows for more precise coupling of the spinal correction system 100 to the vertebral bodies 11. Small changes in position can lead to the exertion of large forces over the spinal column in the anterior and posterior directions. These forces can be significant in the case of segmental fixation, where every vertebral body in the treated region is coupled directly with the spinal correction system 100. These forces are generally undesirable since they are not corrective and can lead to different spinal deformities and potentially spinal stenosis. Thus, in these and other applications, position adjustability can be highly desirable.

Alternatively, elongate structure 260 can be allowed to freely slide (i.e., without fastening by set screw 264) according to forces through natural motion of the spinal column. It should be noted that base 258 can be configured and coupled with spinous process 14 in any manner including each of those described herein with respect to FIGS. 4A-8B and 10A-12B.

Figure 10A:
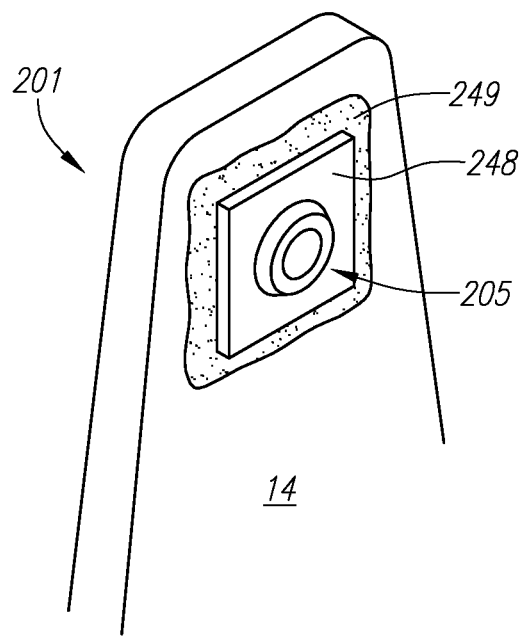
FIGS. 10A-B are perspective views depicting stages of implantation of an example embodiment of an attachment device.

FIG. 10A is a perspective view depicting another example embodiment of attachment device 201 where device 201 includes a plate-like, base structure 248 having an engagement feature 205 located thereon. Base 248 is coupled with spinous process 14 by way of a moldable material 249. Material 249 is preferably configured to harden over time and can be methyl methacrylate (MMA), polymethyl methacrylate (PMMA), epoxy resins, calcium phosphate, and the like.

Figure 10B:
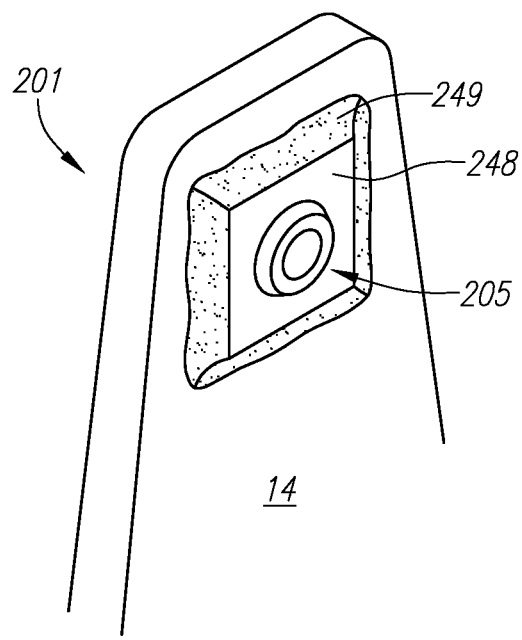

The use of moldable material 249 provides, among others, the ability to manually form material 249 around base 248 to provide a smooth, relatively atraumatic profile and limit any inflammatory response by the body. FIG. 10B depicts base 248 after placement on moldable material 249 and the forming, or molding, of material 249 around base 248 to provide a relatively atraumatic profile. Moldable material 249 can also be fed or forced into one or more iatrogenic recesses or through-openings in spinous process to increase the anchoring with the spinous process.

Figures 11A, 11B:
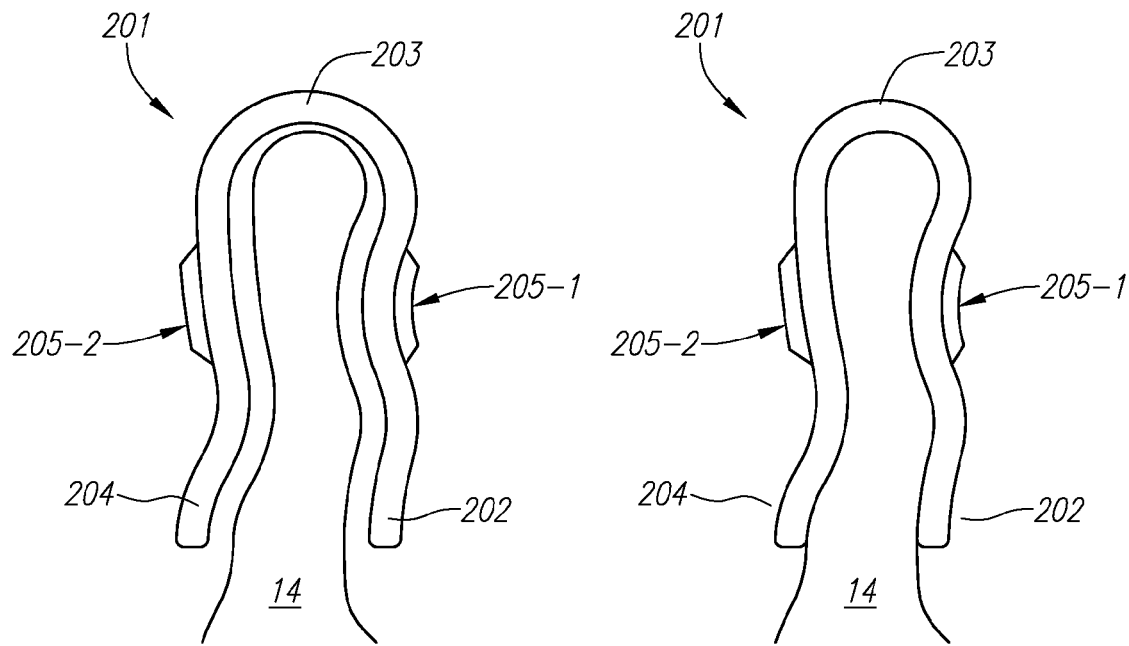
FIGS. 11A-D are cross-sectional views depicting stages of implantation of example embodiments of attachment devices.

It is also possible to configure attachment device 201 to conform to the anatomy of the patient. For instance, FIGS. 11A-B depict an example embodiment of attachment device 201 that has been customized for a certain patient's spinous process 14. Here, attachment device 201 has a U-shape (although it is not limited to such) with first side 202 and second side 204 both having different shaped configurations designed to complement and conform to the features on the patient's spinous process 14.

FIG. 11A depicts attachment device 201 just prior to being clamped on the spinous process 14, and FIG. 11B depicts attachment device 201 after attachment. Mapping data as to the features of the spinous process 14 can be obtained prior to surgery using any visualization method (e.g., CT scans, MRI and the like). The data can also be obtained during surgery using instruments such as a laser profilometer. The mapping data can then be used to manufacture portions 202 and 204 to complement the anatomy. The mapping data can also be used to manufacture any portion of system 100 to fit the patient's anatomy in a customized fashion.

Figures 11C, 11D:
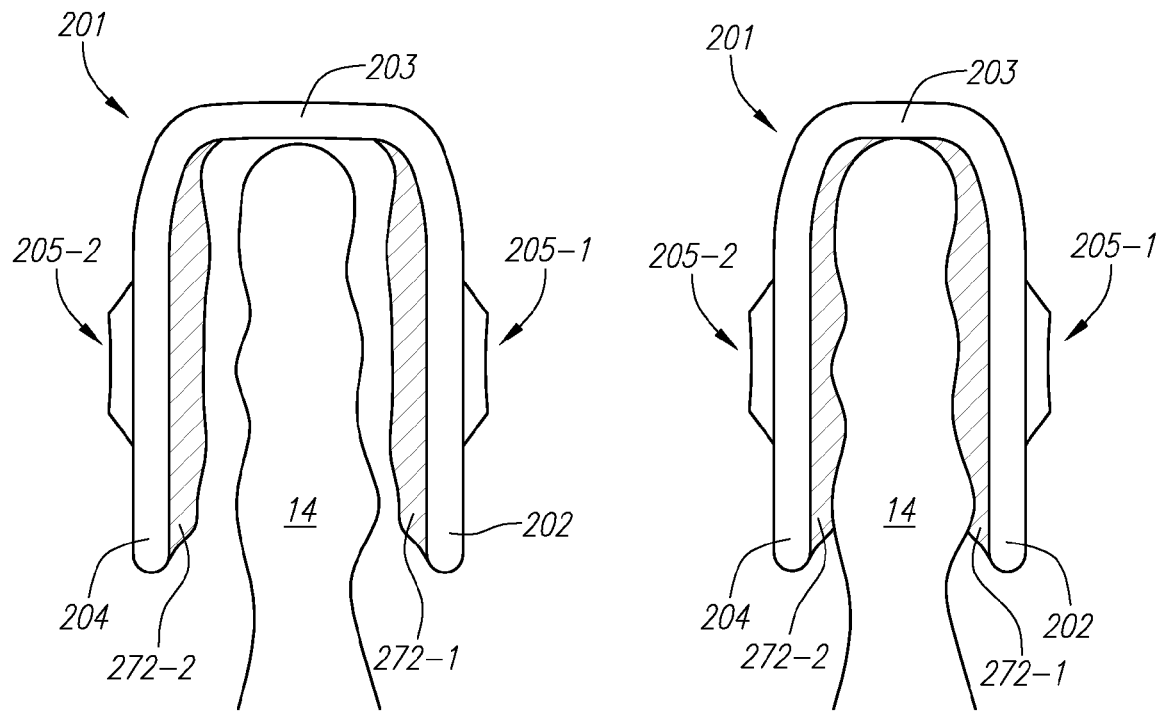

FIGS. 11C-D depict another example embodiment of attachment device 201 where a compliant, or conforming, material 272 is coupled to the inner surface of first portion 202 and second portion 204. Compliant material 272 preferably conforms to the shape of the patient's spinous process when attachment device 201 is attached (FIG. 11C depicts attachment device 201 prior to attachment, and FIG. 11D depicts attachment device 201 post-attachment). Compliant material 272 can be formed from any suitable material including, but not limited to, polymers, gels, rubbers, elastics, silicones and the like.

Figure 12A:
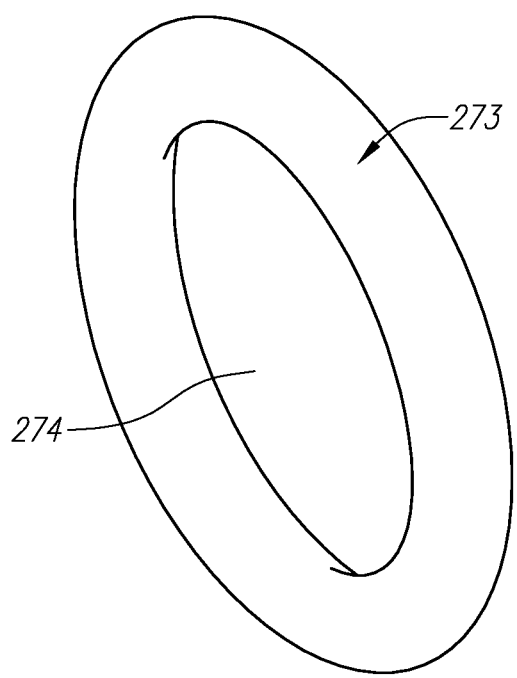
FIG. 12A is a perspective view depicting an example embodiment of a toroidal element.

FIG. 12A depicts an example embodiment of a compliant toroidal element 273 having an inner aperture 274. Toroidal element 273 is preferably placed over spinous process 14 during attachment of device 201 and acts, similar to material 272 described with respect to FIGS. 11C-D, to conform to the features of spinous process 14. Toroidal element 273 can be formed from a compliant material such as those described with respect to FIGS. 11C-D, or can be configured as a fillable structure (e.g., balloon, bag, sheath and the like) that is placed between plate 275 (or 277) and spinous process 14 and then filled with a biocompatible liquid or gel, or a hardening resin such as epoxy or methyl methacrylate (MMA).

Figure 12B:
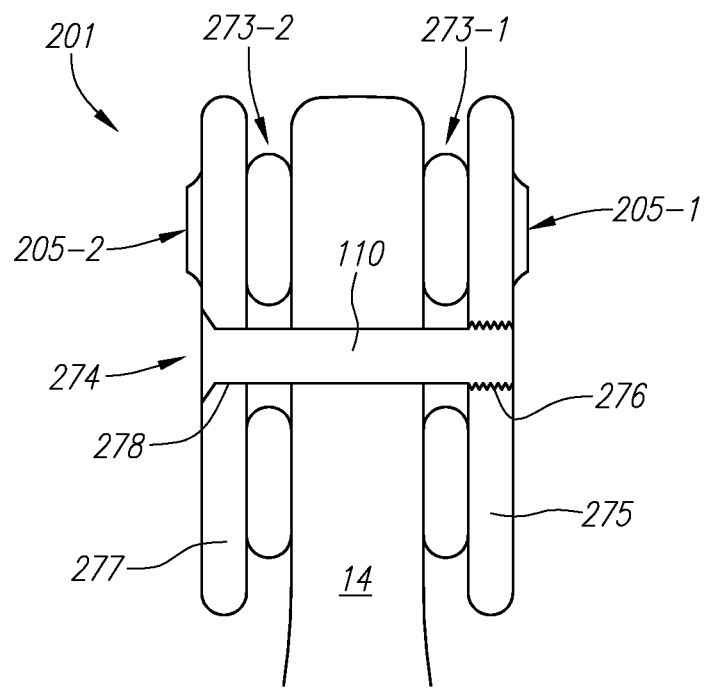
FIG. 12B is a cross-sectional view depicting an example embodiment of an attachment device.

FIG. 12B is a planar cross-sectional view showing attachment device 201 in position over spinous process 14. Here, attachment device 201 includes first and second toroidal elements 273-1 and 273-2 located between spinous process 14 and opposing plates 275 and 277, respectively. Plate 275 includes a threaded lumen 276 for receiving a screw 279 which is inserted through lumen 278 in plate 277 and iatrogenic opening 110 in spinous process 14.

Based on the description provided herein, one of skill in the art will readily recognize that the compliant elements (e.g., 272 and 273) can be configured in other, non-toroidal manners to allow conformance of attachment device 201 to spinous process 14. Use of a moldable, compliant material allows for relatively standardized rigid attachment structures to be used without the need to pre-profile the patient's anatomy.

Figure 12C:
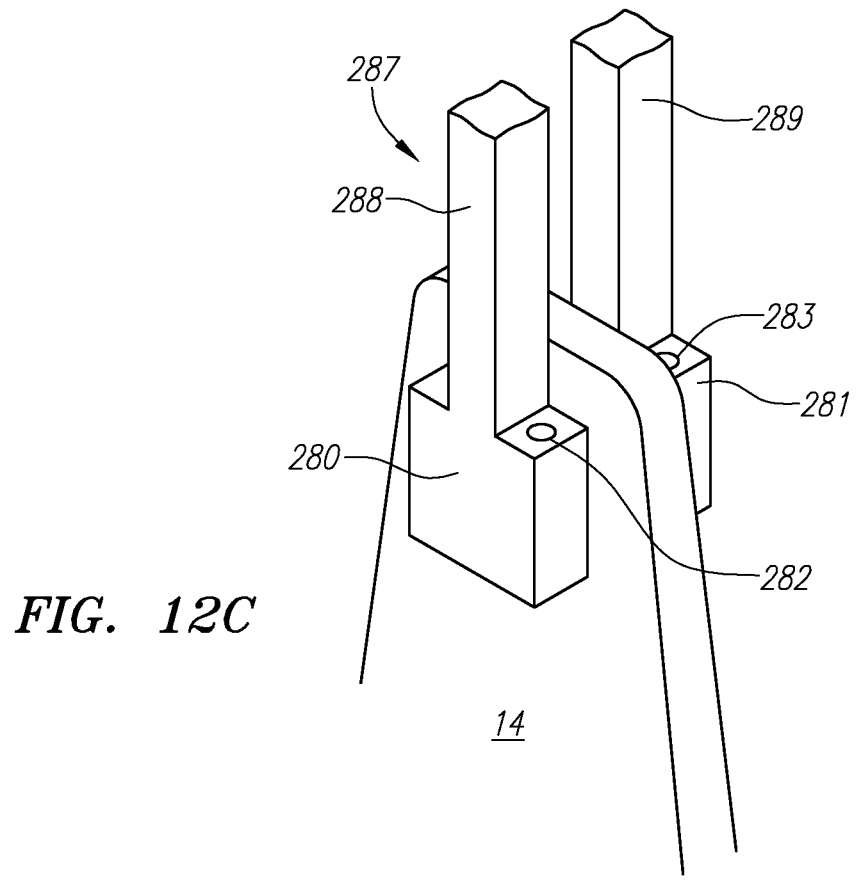
FIGS. 12C-D are perspective views depicting example stages of casting an example embodiment of an attachment device.
Figure 12D:
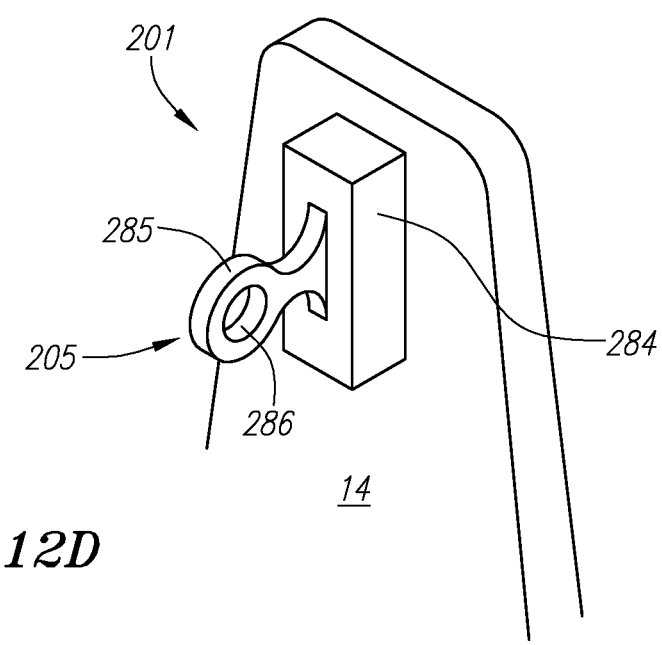

In addition to using prefabricated structures, attachment device 201 (or any portion thereof) can be cast in place over spinous process 14 during surgery. FIGS. 12C-D are perspective views depicting an example embodiment of attachment device 201 during casting over spinous process 14. In FIG. 12C, a casting device 287, having two molds 280 and 281 coupled with shafts 288 and 289, respectively, are placed on opposing sides of spinous process 14 over an iatrogenic opening (not shown) extending therebetween. Mold 280 includes an injection port 282 through which the material to be cast is injected, and mold 281 preferably includes a vent port 283 for venting during the injection of the cement or resin. In an alternative embodiment, the cement or resin can be injected into mold 280 through an inner lumen in shaft 288. Venting can also occur through a lumen in shaft 289.

The inner surface of each mold 280 and 281 is shaped so as to cast the desired attachment device configuration, an example of which is depicted in FIG. 12D. Here, attachment device 201 includes a plate-like base 284 with an elongate strut 285 extending therefrom having an eyelet 286 through which a rod, sleeve spinal coupling device or any other component of the spinal correction system can be routed. A corresponding structure is preferably cast on the opposing side, the two opposing structures being fastened to each other and spinous process 14 by the presence of the resin or cement within the iatrogenic opening (not shown) in spinous process 14.

Like the embodiments described with respect to FIGS. 7A-E, the use of materials or configurations that conform to or match the shape of the patient's spinous process, such as in the embodiments described with respect to FIGS. 10-12D, provide for, among other things, the distribution of force evenly across the engaged surface and the elimination or reduction of the potential of stress risers.

Numerous embodiments of attachment devices 201 have been described, such as with respect to FIGS. 4A-12D. One of skill in the art will readily recognize that the features of those embodiments can be substituted for or combined with the features of any other embodiment. For instance, various techniques and configurations for attaching device 201 to the spinous process 14 are disclosed, and those techniques and/or configurations can be used in place of or in combination with any other technique or configuration disclosed.

As discussed earlier, provided herein are methods for minimally invasive implantation of spinal correction systems within the body of a patient. Preferably, the spinal correction system is attached to a spinous process of a patient's vertebral body by exposure of only the spinous process of that vertebral body, although other variations of minimally invasive implantation procedures have been described herein.

Figure 13:
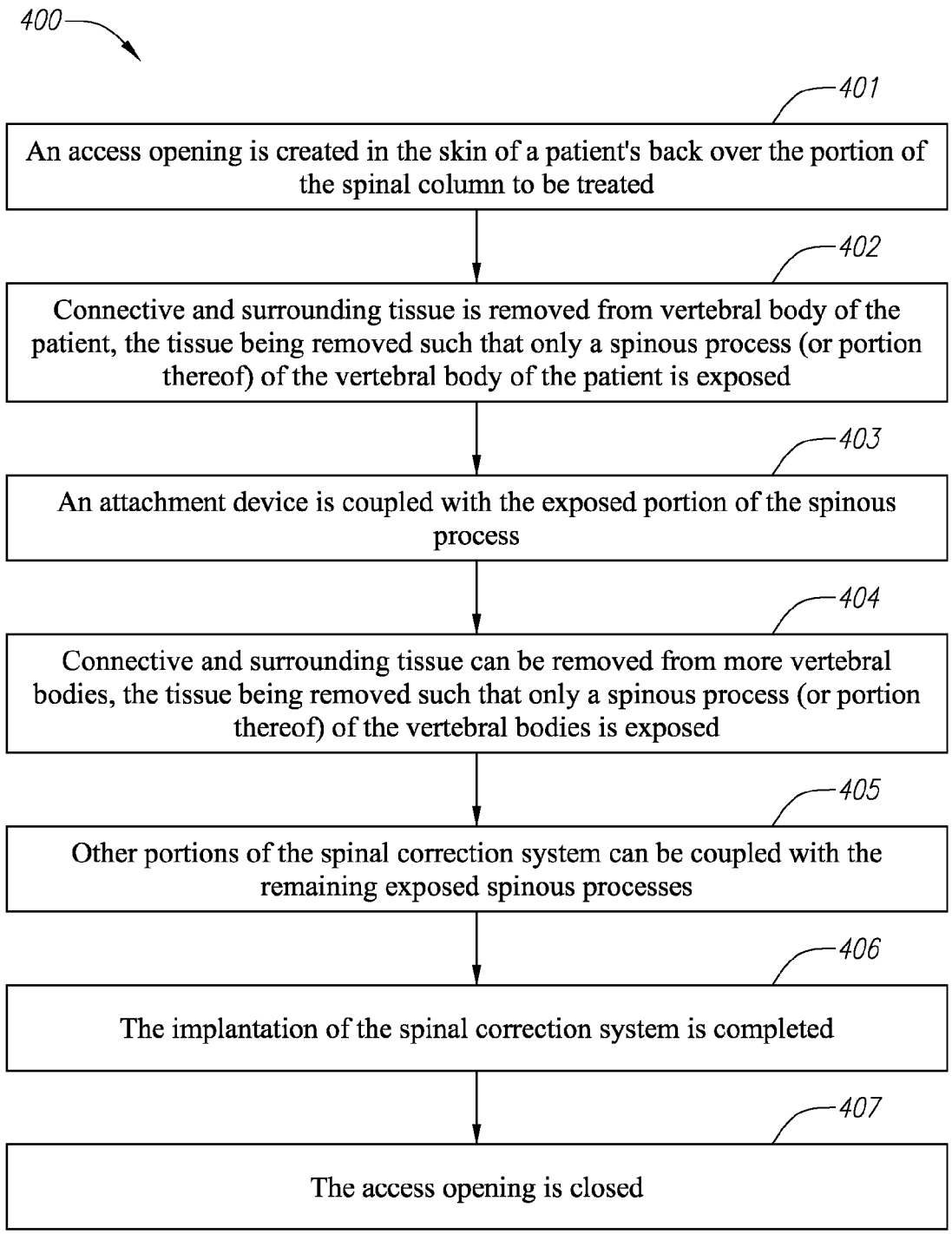
FIGS. 13-14 are flowcharts depicting example methods of implantation of a spinal correction system.

FIG. 13 is a flowchart depicting an example method of implantation 400 of a spinal correction system in a minimally invasive manner. In this embodiment, only the spinous process of the vertebral bodies is exposed, but it should be noted that, in other embodiments of this method, different amounts of the vertebral body can be exposed, or tissue dissected therefrom, including each of the variations of the minimally invasive methods described herein.

At 401, an access opening is created in the skin of a patient's back over the portion of the spinal column to be treated. At 402, connective and surrounding tissue is removed from a vertebral body of the patient, the tissue being removed such that only a spinous process (or portion thereof) of the vertebral body of the patient is exposed. At 403, an attachment device is coupled with the exposed portion of the spinous process. The attachment device is preferably configured to allow the transmission of a corrective force from at least one elongate rod of the spinal correction system to the patient's spinal column. At 404, connective tissue can be removed from more vertebral bodies, if desired, preferably occurring such that only the spinous process (or a portion thereof) of the additional vertebral bodies is exposed. Once exposed, at 405, other portions of the spinal correction system can be coupled with those spinous processes. At 406, the implantation of the spinal correction system is completed and, at 407, the access opening is closed.

In removing the connective tissue from the spinous process of a patient's vertebral body, preferably, the medical professional will first gain access to the supraspinous ligament and create an incision through that ligament to gain access to the underlying interspinous tissue. In this embodiment, any tissue connected with the spinous process is then dissected from the spinous process, taking care to avoid dissection from, at least, the anterior portion of the flared transitional regions, and preferably the entirety of the transitional regions. As noted above, preferably the facet joints and the laminae are left unexposed as well. The dissected tissue can include connective tissue such as the interspinous ligament as well as surrounding muscular or fatty tissue. The dissected tissue is pulled away to expose the spinous process.

Figure 14:
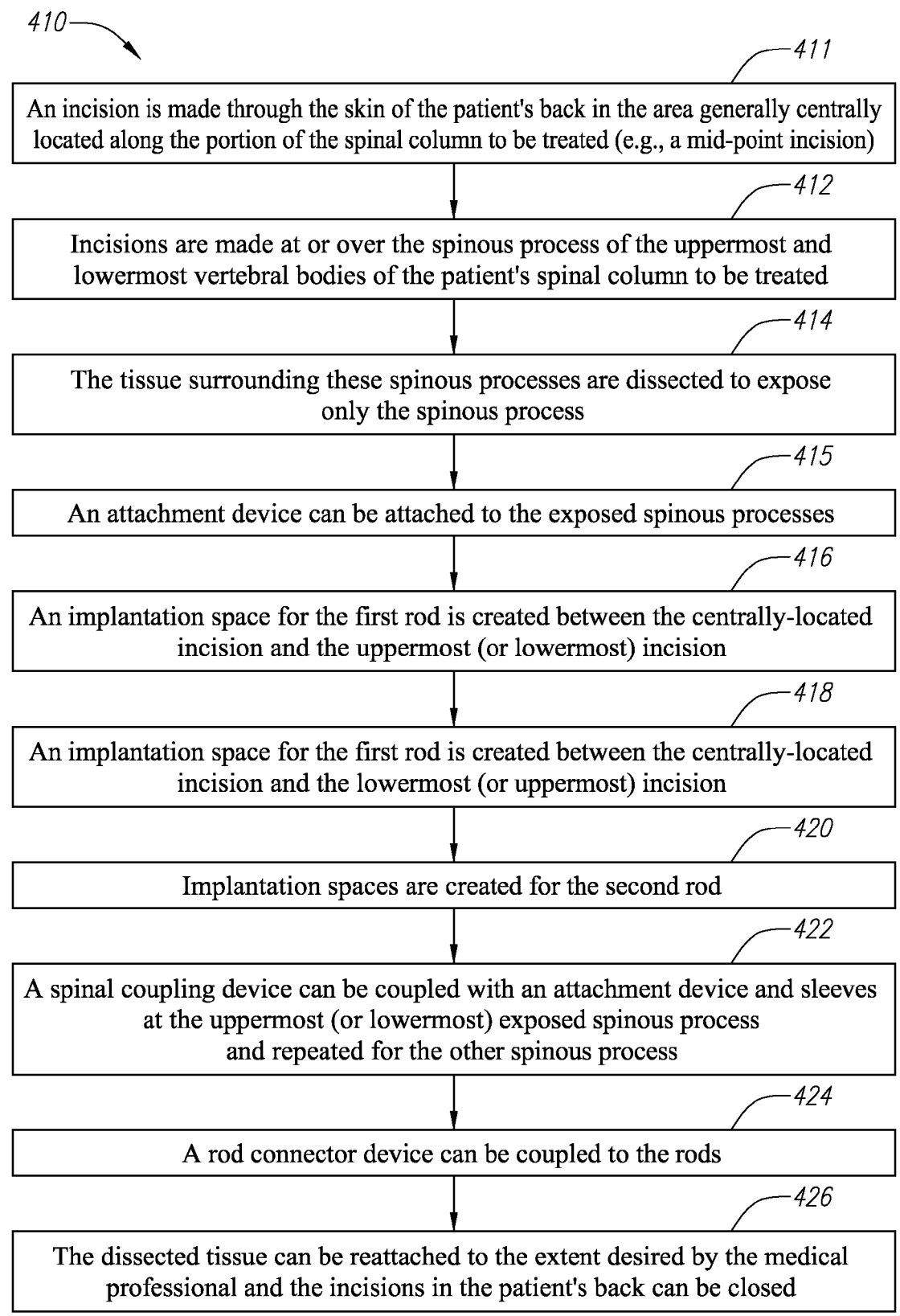

FIG. 14 is a flow diagram depicting another example method 410 of implantation of a spinal correction system. Here, the method of implantation will be described with respect to implantation of spinal correction system 100 described with respect to FIGS. 2A-B. At 411, an incision is made through the skin of the patient's back in the area generally centrally located along the portion of the spinal column to be treated (e.g., a midpoint incision). At 412, incisions are made at or over the spinous process of (preferably) the uppermost and lowermost vertebral bodies of the patient's spinal column to be treated. At 414, the tissue surrounding these spinous processes are dissected to expose only the spinous process. At 415, any desired attachment device (such as attachment devices 201 described herein) can be attached to these exposed spinous processes.

Figure 15A:
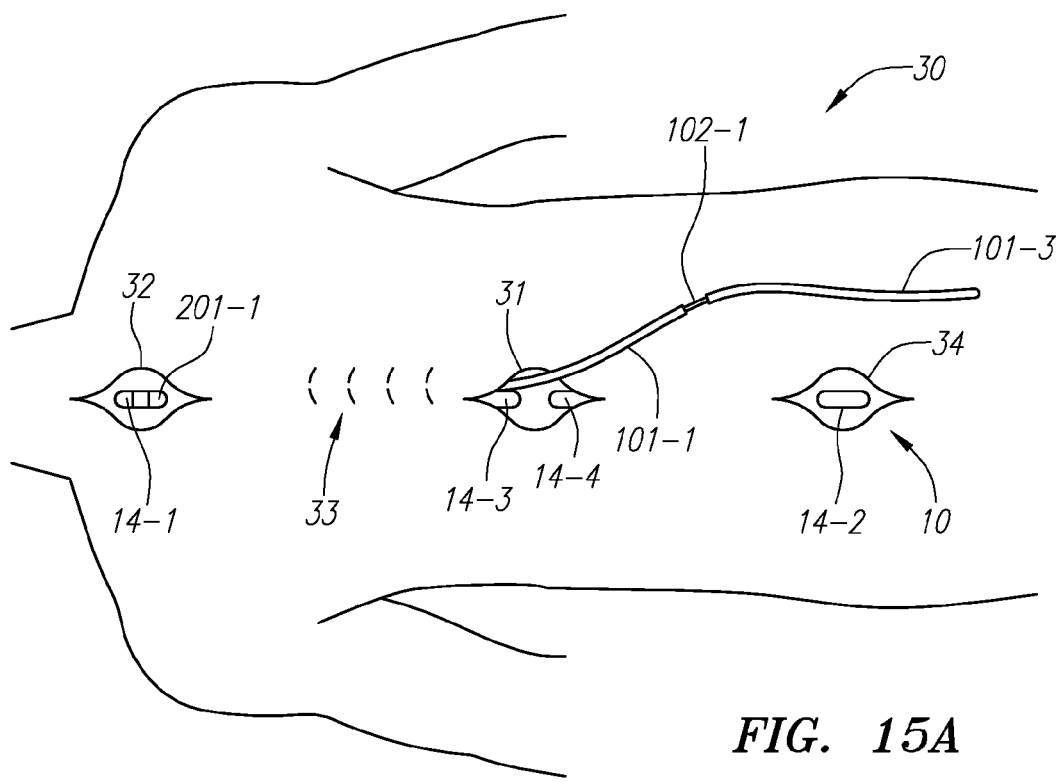
FIGS. 15A-D are perspective views depicting example stages of implantation of a spinal correction system.

At 416, an implantation space is preferably created between the centrally-located incision and the uppermost incision. An example of this is depicted in the perspective view of FIG. 15A, where rod 102-1, contained within sleeves 101-1 and 101-3, is advanced from centrally located incision 31, toward uppermost incision 32 of the patient 30 to create a first implantation space 33-1 beneath the patient's skin. Implantation space 33 is depicted as a raised portion of the patient's skin, although in practice a raised appearance may not be present. Preferably, implantation space 33 is created between each spinous process and the adjacent interspinous tissue (e.g., the interspinous ligament). Accordingly, spinous processes 14-3 and 14-4 are exposed through incision 31 to allow access to implantation spaces 33.

The use of rod 102 or a similarly shaped instrument is beneficial in that rod 102 is preferably shaped similarly to the deformity of the patient's spinal column 10 and therefore is suited to create implantation space 33 in the appropriate orientation and shape. It should be noted that any shaped or unshaped instrument can be used to create the implantation channel as desired for the application.

Implantation space 33 is preferably created in a blunt manner by advancing the distal end of rod 102-1 while within sleeve 101-1 along the spinal column 10 between each spinous process 14 and the adjacent interspinous ligament and other interspinous tissue. The distal end of rod 102-1 and sheath 101-1 is preferably relatively blunt in order to minimize the risk of inadvertently damaging spinal column 10 or the tissue and ligaments adjacent thereto. This advancement is continued until spinous process 14-1 of uppermost incision 32 is reached. One of skill in the art will readily recognize that uppermost incision 32 (or the lowermost incision) can be created before or after the rod is actually advanced along spinal column 10.

Figure 15B:
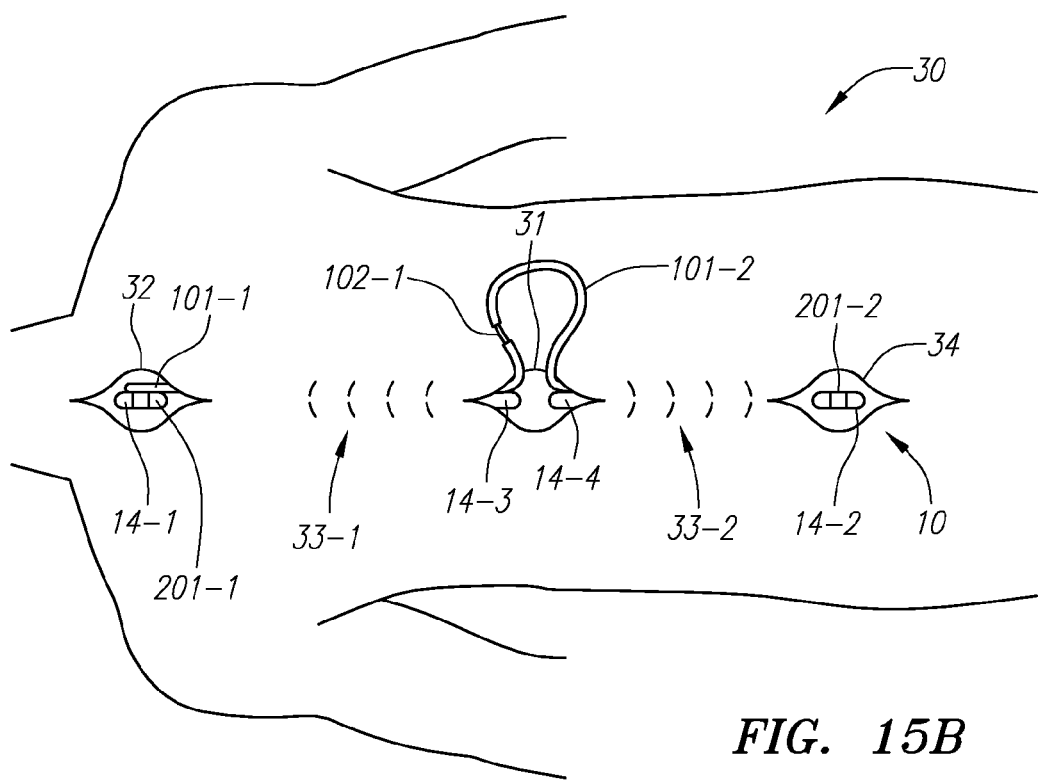

At 418, implantation space 33-2 is created between incision 31 and lowermost incision 34, again, preferably by advancing rod 102-1 and sheath 101-3 in a blunt manner. This can occur in at least several ways. First, as depicted in FIG. 15B, rod 102-1 is bent in the midsection, and the opposite end is inserted from central incision 31 toward incision 34. This is preferably possible due to the high flexibility of rod 102-1. Alternatively, rod 102-1 can be composed of a biocompatible shape-memory material such as nitinol, where it can first be cooled or chilled to allow it to be easily deformed from its pre-curved shape to the bent configuration depicted here. Once inserted into the body, rod 102-1 will warm to the body's temperature and reenter the pre-curved configuration.

Figure 15C:
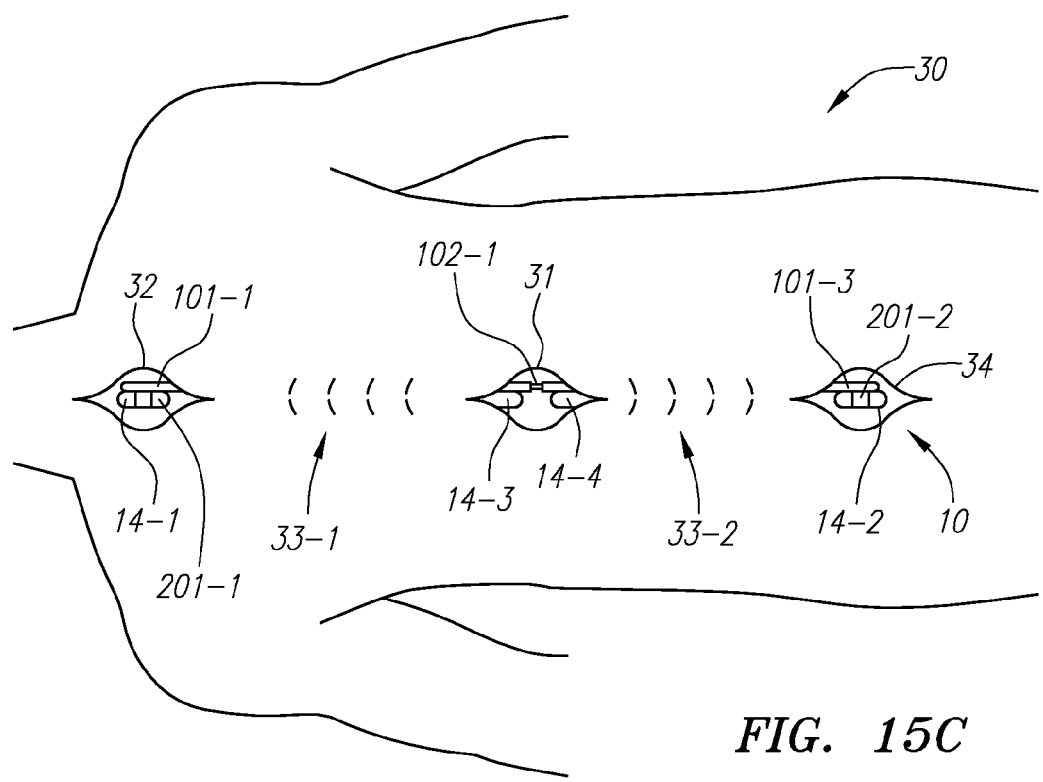

In another example, rod 102-1 is advanced from central incision 31 through implantation space 33-1 and through incision 32, until the opposing end of rod 102-1 is capable of being inserted into central incision 31. At this point, rod 102-1 can then be advanced from uppermost incision 32 past central incision 31 and along spinal column 10 until position appropriately within lowermost incision 34, as depicted in FIG. 15C.

In yet another example, as described earlier, two (or more) rod segments can be used instead of a single continuous rod. In this embodiment, a first rod segment can be inserted from the central incision 31 toward the uppermost incision 32, and a second rod segment can be inserted from the central incision 31 toward the lowermost incision 34. The rod segments can be inserted while within sleeves 101, or sleeves 101 can be inserted first. These rod segments can then be joined by a connector, such as rigid rod connector 106 at central incision 31, which also preferably couples the rod segments to the rod (or rod segments) on the opposing side of the spinal column.

Figure 15D:
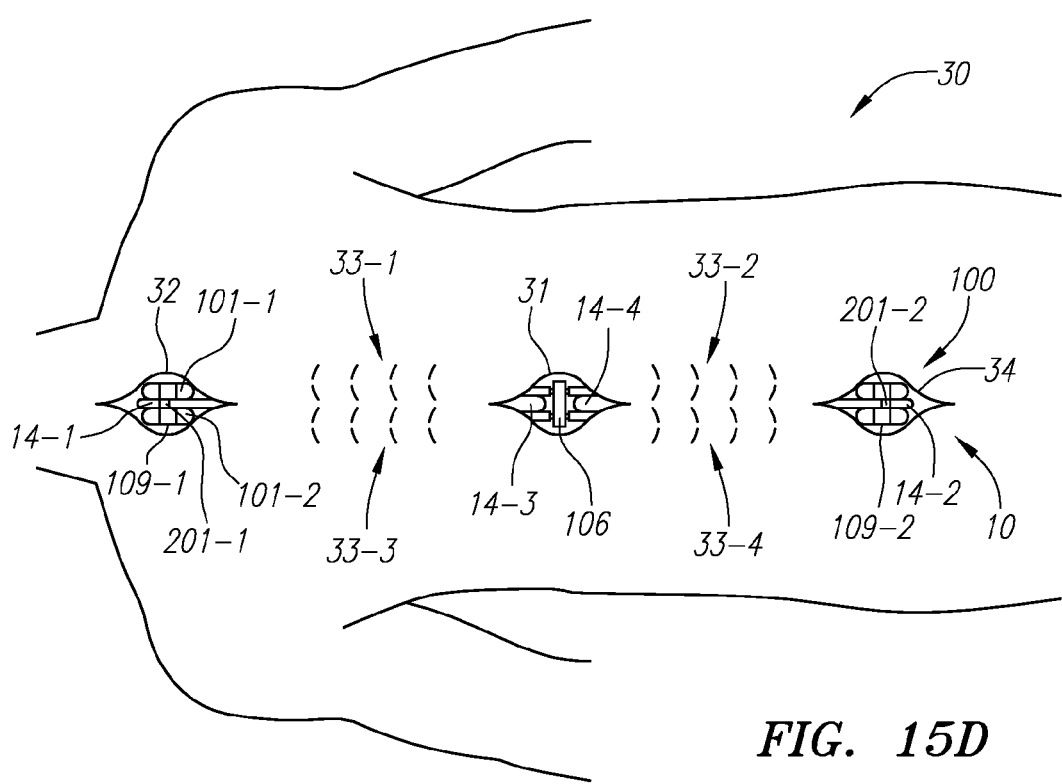

At 420, implantation spaces 33-3 and 33-4 are created for the second rod 102-2. At 422, uppermost spinal coupling device 109-1 can be coupled with attachment device 201-1 and sleeves 101-1 and 101-2. The process can be repeated, and lowermost spinal coupling device 109-2 can be coupled with attachment device 201-2 and sleeves 101-3 and 101-4. At 424, rod connector device 106 is preferably coupled to rods 102-1 and 102-2. This can occur through the interspinous ligament between adjacent spinous processes 14. In this embodiment, coupling bands 108 are not used. This generally final configuration of system 100 is depicted in FIG. 15D. At 426, the dissected tissue can then be reattached to the extent desired by the medical professional, and the incisions 31, 32 and 34 in the patient's back can be closed.

It should be noted that numerous variances from the above-described method can be implemented. For instance, although the uppermost and lowermost spinous processes 14-1 and 14-2 are shown to be adjacent to the ends of system 100, system 100 can extend past these spinous processes further along the spinal column. In addition, the order in which system 100 is implanted can vary. For instance, instead of inserting rods 102 and sleeves 101 together to create the implantation spaces, another instrument can be first used. That instrument can be configured to create both implantation spaces for both rods at the same time. Sleeves 101 can then be placed within the implantation space followed by rods 102. Alternatively, rod 102 can be implanted first (with or without the aid of another instrument) and used as a guide over which sleeves 101 can be inserted. In this example, the sleeves can be inserted from the uppermost or lowermost incisions (or both in the case of more than one sleeve).

In another embodiment, no direct coupling is made to the spinal column at upper and lower positions. Only one incision is required to be made, preferably a centrally located one from which system 100 can be implanted. A rod connector 106 is then preferably applied to connect rods 102, either through the interspinous ligament itself, such that the device is essentially "free-floating," or coupled directly to a spinous process.

In yet another embodiment, to create the implantation space, a thin, flexible guide instrument is first inserted along the spinal column. Sleeve 101 and rod 102 can then be attached to an end of the guide instrument and pulled through the channel created by the instrument to route sleeve 101 and rod 102 appropriately.

In a further embodiment, only lowermost and uppermost incisions are made and the centrally located incision is foregone. In such an embodiment, the rigid connection of rods using coupling device 106 preferably occurs at least the uppermost or lowermost incisions, if not both. This implantation method can prove desirable with the implantation of shorter systems 100.

Figure 16:
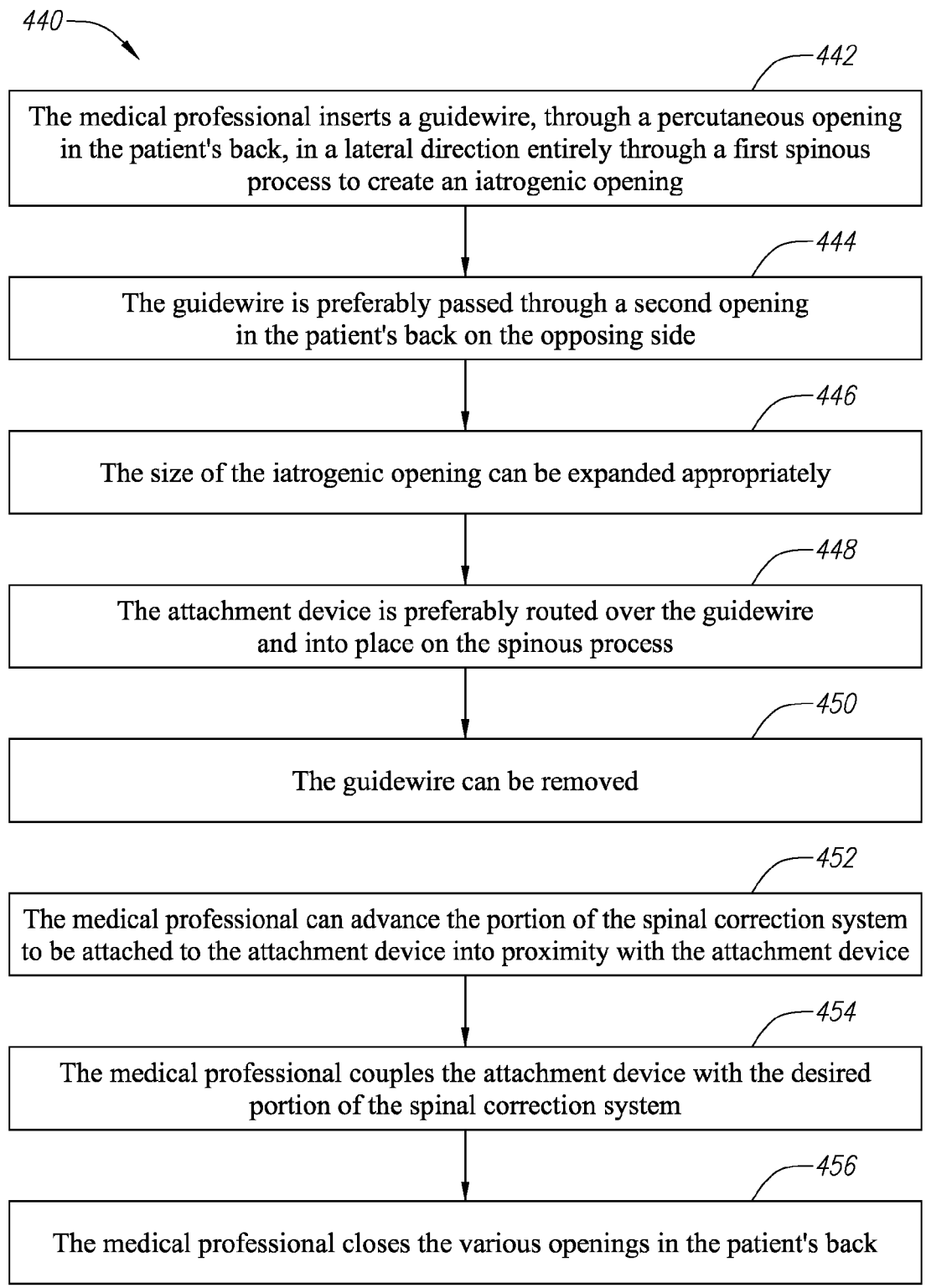
FIG. 16 is a flowchart depicting an example method of implantation a spinal correction system.

FIG. 16 is a flowchart depicting another example method 440 of implanting a spinal correction system 100, where the implantation of one or more attachment devices 201 occurs with the aid of a guidewire. An example embodiment of an attachment device 201 configured for implantation with the aid of a guidewire is described with respect to FIG. 5G, although it should be noted that this example method is not limited to such an embodiment of the attachment device.

At 442, the medical professional inserts a guidewire through a percutaneous opening in the patient's back (created by the guidewire or another instrument), in a lateral direction entirely through a first spinous process to create an iatrogenic opening. This can be accomplished with a guidewire having a sharp tip, such as a Kirschner wire (K-wire), or with another piercing instrument. Imaging, such as fluoroscopy, is also preferably employed to aid the physician in piercing the spinous process in the desired location. At 444, the guidewire is preferably passed through a second opening in the patient's back on the opposing side.

At 446, the size of the iatrogenic opening can be expanded appropriately. This can be accomplished by the iterative application of one or more dilators, each being larger than the previous dilator (or the guidewire). At 448, the attachment device is preferably routed over the guidewire and into place on (one or both sides of) the spinous process.

For instance, if using an embodiment similar to that described with respect to FIG. 5G, the attachment device 201 is placed sequentially on both sides of spinous process 14 starting with the opposing base plates 153 and 154, each advanced into position over guidewire 156 from the opening in the patient's back on each respective side of spinous process 14. It should be noted that the openings through the skin and tissue (e.g., fascia) to spinous process 14 can be sized corresponding to the largest portion of the attachment device 201 that must be advanced therethrough, thereby allowing the size of these openings to be minimized. Guide elements 152 and 155 are also advanced into place over guidewire 156 and into position over each base plate 153 and 154, after which screw 151 is advanced and used to couple the components together.

At 450, the guidewire can be removed. Then, at 452, the medical professional can advance the portion of the spinal correction system to be attached to the attachment device into proximity with the attachment device such that it can be coupled thereto. For instance, the medical professional can advance a rod (or sleeve, or rod and sleeve, etc.) through a separate opening in the patient's back and into proximity with the attachment device.

At 454, the medical professional couples the attachment device with the desired portion of the spinal correction system. For instance, in one embodiment the attachment device includes an eyelet or other housing for receiving the rod, and the rod can be routed directly through the eyelet to couple the two together, thereby requiring minimal access (and a minimal opening) for the medical professional through the laterally placed openings in the patient's back. Depending on the level of user access needed to couple the rod or component with the attachment device, the opening through which the attachment device is inserted can also be minimized. Also, the opening through which the rod or other component of the spinal correction system is inserted can be sized minimally, generally the same as that rod or component. After completion of the implantation of the spinal correction system, which may include the implantation of multiple attachment devices, then at 456, the medical professional closes the various openings in the patient's back.

Figure 17:
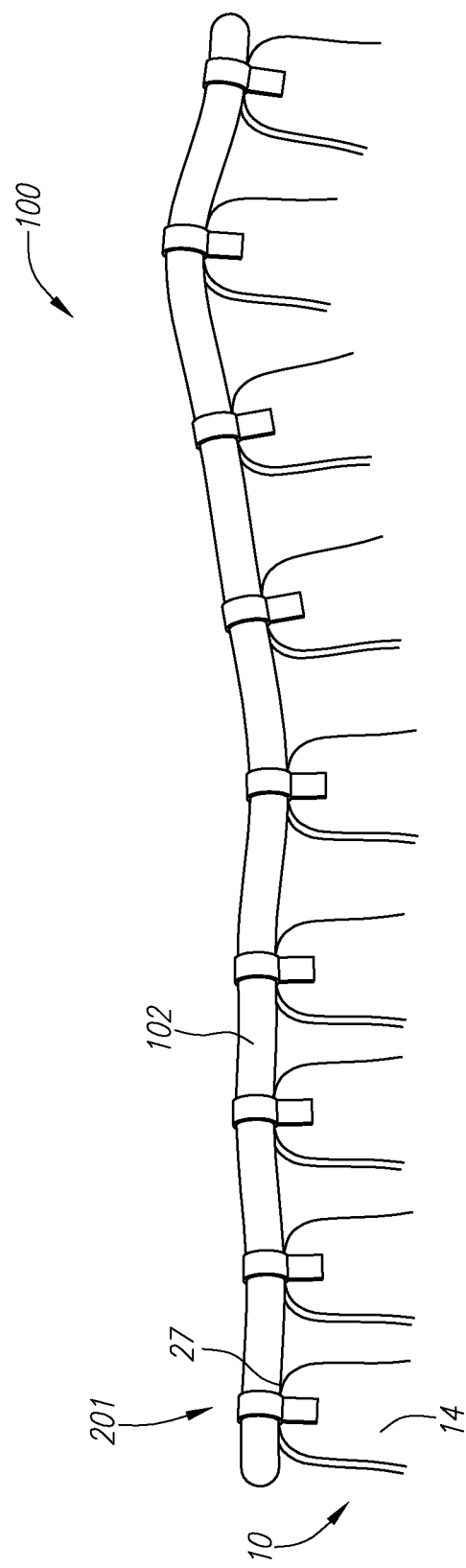
FIG. 17 is a lateral view depicting an example embodiment of a spinal correction device.

Of course, if desired, a single incision can be placed along the length of the spinal column where system 100 is to be implanted, to expose the entire implantation space. This can allow for other configurations of system 100 to be implanted. FIG. 17 is a lateral view depicting another example embodiment of spinal correction system 100. Here, system 100 is configured to be implanted along the edges of the posterior side 27 of one or more spinous processes 14. Multiple attachment devices 201 are coupled on each spinous process 14 to be treated, and include a tubular portion configured to hold a rod 102. This embodiment provides the benefit of restricting exposure of spinous processes 14 to only the most posterior portion (e.g., less than 50% of the length of each spinous process 14).

Any portion of system 100 can be coated with any material as desired. Some example coatings that can be used include coatings that are biodegradable, drug coatings (e.g., drugs can be released from hydrogels or polymer carriers where the polymer itself is a biodegradable material or elastomer, coatings that increase or decrease lubricity, bioactive coatings, coatings that inhibit thrombus formation, and coatings that speed the healing response.

These coatings can be applied over the entire system 100 or any portion thereof. Also, different portions of system 100 can be coated with different substances. Furthermore, the surface topography of the elements of system 100 can be varied or configured to accelerate biodegradation of those elements (if including biodegradable materials) and/or to promote tissue encapsulation thereof.

Figure 18:
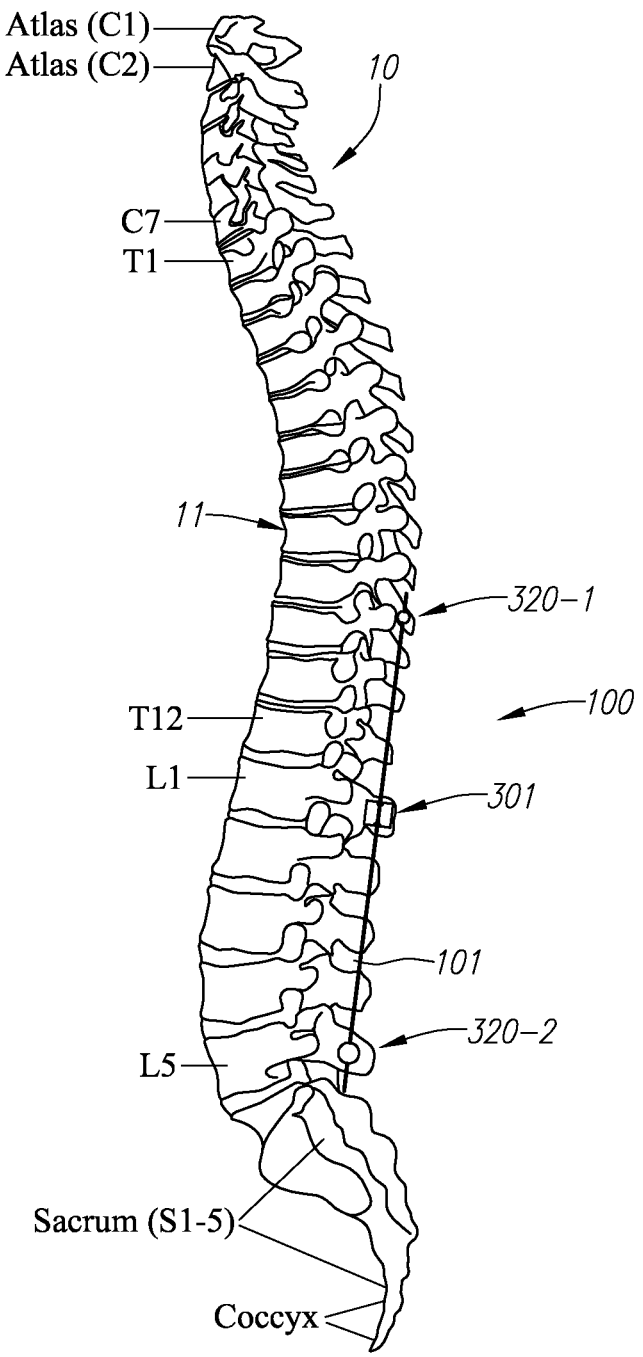
FIG. 18 is a lateral view of a spinal column having an example embodiment of a treatment system attached thereto.

FIG. 18 is a side view of a spinal column having another example embodiment of a corrective treatment system 100 attached thereto. This treatment system can be implanted with any of the methods of implantation described herein. In this embodiment, treatment system 100 includes rod 102 and three engagement devices (or connectors) 301, 320-1 and 320-2 that couple rod 102 to selected individual spinous processes 14 of the patient's spinal column 10. Alternatively, system 100 can be connected to the pedicles. Here, a connector 301 of a first type is coupled with spinous process 14 of the L1 vertebral body and connectors 320-1 and 320-2 of a second type are coupled with the superiorly located T9 vertebral body and the inferiorly located L5 vertebral body. These locations are merely examples and it should be understood that the number and placement of connectors 301 and 320 are dependent on the condition of the patient and desired treatment plan set forth by the administering medical professional.

Connector 301 is preferably secured to a spinous process 14 and configured to permit certain limited movement of rod 102 in relation to connector 301 (and the vertebral body to which it is connected). Preferably, connector 301 limits the degree to which rod 102 can translate (or slide) longitudinally along the patient's spinal column, i.e., in the inferior and superior directions, and substantially prevents rod 102 from rotating about its longitudinal axis. For this reason, connector 301 will be referred to herein as a "fixed" connector, although connector 301 does allow rod 102 to pivot (or tilt) in certain directions as will be explained in more detail herein.

Connectors 320 are also preferably configured to allow rod 102 to pivot and rotate in certain directions, but connectors 320 also preferably allow rod 102 to translate (or slide) longitudinally along the patient's spinal column. For this reason, connector 320 will be referred to herein as a "slidable" connector. Connectors 301 and 320 can also be referred to as housings, retainers, fixation points or couplings.

In a preferred embodiment, at least one fixed connector 301 is present to limit the translation of rod 102 with respect to the spinal column. However, if desired, more than one fixed connector 301 can be used at any point along the length of rod 102. In this embodiment, two slidable connectors 320 are located at each end of rod 102 to retain rod 102 in proper alignment with the spinal column, however, any desired number of one or more slidable connectors 320 can be placed at any vertebral body in the region to be treated. If one slidable connector 320 and one fixed connector 301 are used, preferably they are placed on opposite ends of rod 102.

Figure 19A:
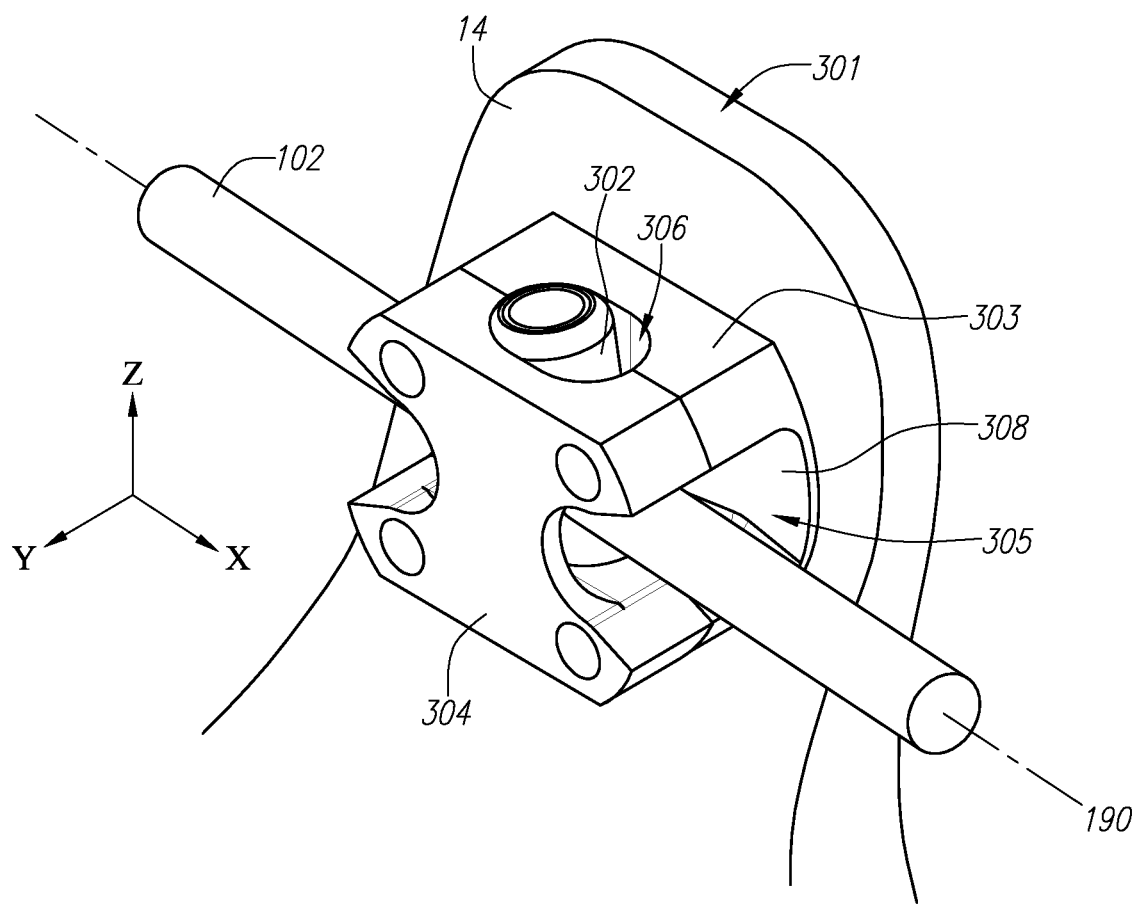
FIG. 19A is a perspective view of an example embodiment of a fixed connector coupled to a spinous process.

FIG. 19A is a perspective view depicting an example embodiment of fixed connector 301 with rod 102 coupled thereto. Here, rod 102 is fixed to an axle member 302 that extends on opposite sides of rod 102 and interfaces with the fixed connector 301. Axle member can be coupled with the rod in any manner that prevents rotation of rod 102 with respect to axle member 302 including, but not limited to, an interference fit, welding, soldering, adhesives, clamps and the like. Preferably, axle member 302 has a through-lumen to receive rod 102 and is coupled with rod 102 using a press fit, such as a cryo-fit. Alternatively, axle member 302 can be an integral part of the rod, e.g., the rod and axle member are of uni-body construction. One such method of manufacturing a uni-body construction can be grinding or otherwise removing excess material from a larger piece of material to form the desired diameter rod with one or more elongate projections that act as the axle member.

Fixed connector 301 includes an inner housing 303 and an outer housing 304, which together form two lumens 305 and 306 in which rod 102 and axle member 302 are housed, respectively. Lumens 305 and 306 are preferably oversized to allow specific types of movement by rod 102 and axle member 302. For example, fixed connector 301 is configured to allow rod 102 to pivot within lumen 305 in the coronal plane of the vertebral body (indicated as the X-Y plane) and to allow axle member 302 to pivot within lumen 306 in the sagittal plane (indicated as the X-Z plane). Fixed connector 301 is configured to allow a limited amount of longitudinal translation. In this embodiment, the translation is limited to the difference between the superior-to-inferior length of lumen 306 and the diameter of axle member 302. Fixed connector 301 is also configured to prevent rod 102 from substantial rotation about its longitudinal axis 190. A negligible degree of rotation is possible due to manufacturing tolerances and the like. By allowing pivoting of rod 102 in the coronal and sagittal planes, fixed connector 301 is configured to alleviate, or at least reduce, any moments created in those planes through movement of the patient. This can reduce lateral and rotational stresses placed on spinous process 14. Limiting the ability of rod 102 to rotate about its longitudinal axis helps maintain the predetermined corrective shape of rod 102 in the proper radial alignment to apply a properly directed corrective force (i.e., so as not to "correct" natural proper curvature of the spine).

Figure 19B:
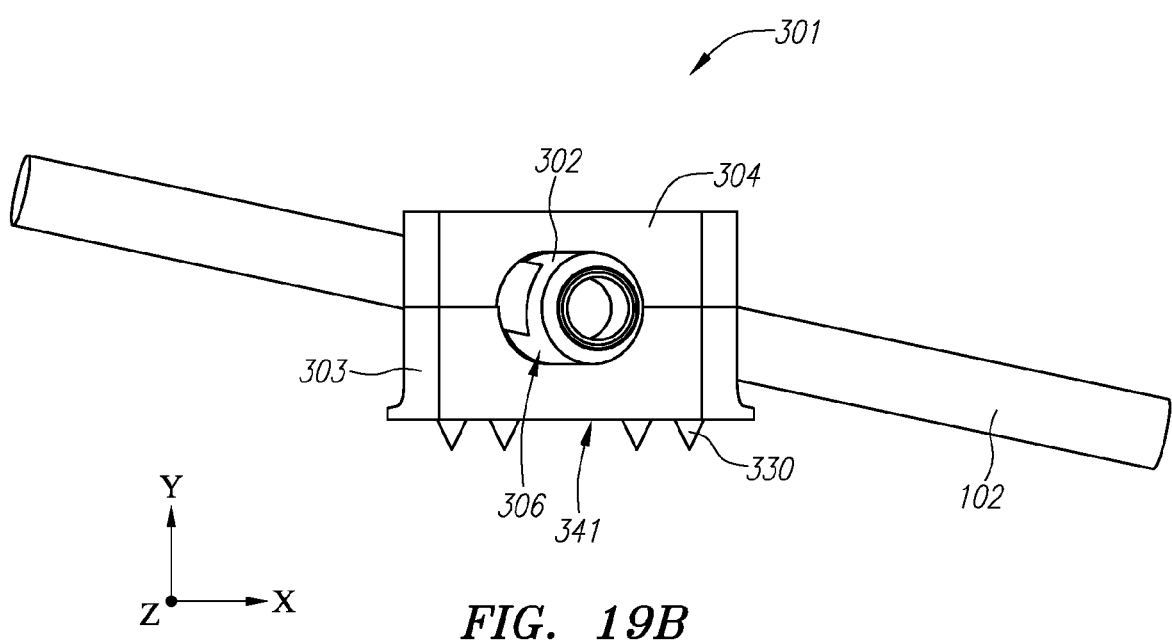
FIG. 19B is a side view of an example embodiment of a fixed connector.

FIG. 19B is a side view of fixed connector 301 showing rod 102 therein. Rod 102 has the freedom to pivot or pivot about axle member 302 in the coronal plane. Lumen 305 is preferably larger than the diameter of rod 102 and sized and shaped to permit and not obstruct the preferred range of motion for rod 102. Also shown are engagement features 330, which in this embodiment are configured as conical abutments or spikes that protrude from the base surface 341 of inner housing 303 and can be capable of acting as a bone anchor to facilitate the securement of connector 301 to the spinous process. These engagement features 330 will be discussed in more detail herein.

Figure 19C:
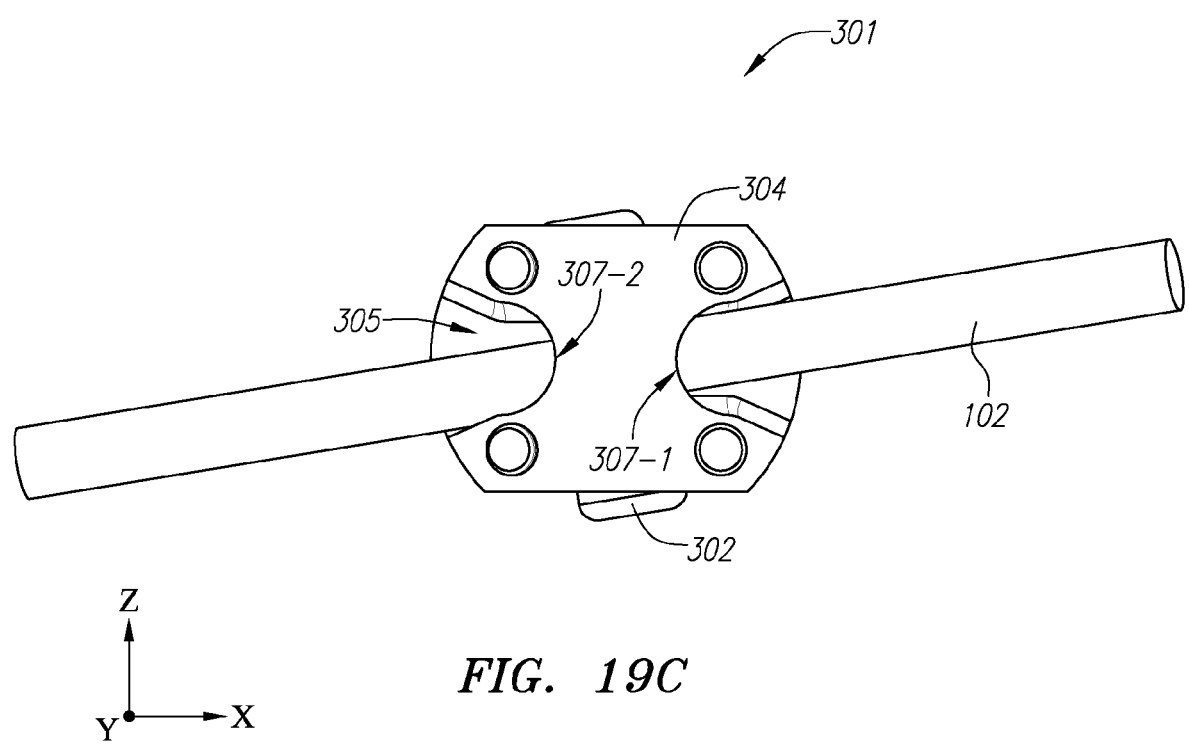
FIG. 19C is a top-down view of an example embodiment of a fixed connector.

FIG. 19C is a top-down view of fixed connector 301 with rod 102 housed therein and pivoted in the coronal and sagittal planes. This pivoting occurs about axes that intersect rod 102, and thus allow for efficient alleviation or reduction of moments on the underlying vertebral body. Here, pivoting in the coronal plane occurs about axis 377, which is the longitudinal axis of axle member 302 and intersects rod 102. Pivoting in the sagittal plane occurs about axis 378 (shown here as normal to FIG. 19C), which intersects rod 102 at axle member 302.

Outer housing 304 includes upper and lower U-shaped or concave recesses 307, which allow rod 102 to pivot as shown in FIG. 19B. The depth to which recesses 307 extend from the sides of connector 301 can, at least partially, determine the degree to which rod 102 can pivot in the coronal plane. Likewise, the width of recesses 307 can, at least partially, determine the degree to which rod 102 can pivot in the sagittal plane while simultaneously pivoting in the coronal plane. The degree of pivoting in the sagittal plane can also be determined by the shape of lumen 306 as described below.

Referring back to FIG. 19A, the inner base surface of inner housing 303 is tapered in region 308 to allow even greater freedom to pivot in the coronal plane. FIG. 19B shows lumen 306 with axle member 302 housed therein. Here, it can be seen that lumen 306 allows axle member 302 to rotate in the coronal plane. Lumen 306 is oversized along the X-axis but has a width similar to the diameter of axle 302 along the Z-axis. This allows limited pivoting of rod 102 in the sagittal plane while at the same time restricting the rotation of rod 102 about its longitudinal axis. This also allows rod 102 to slide by a limited amount along the X-axis.

As noted herein, system 100 can include a rod 102 or other corrective device positioned on one or both sides of the patient's spinous processes. The following figures describe an example embodiment of system 100 where two separate rods are used, each being positioned on a separate side of the patient's spinal column.

Figure 19D:
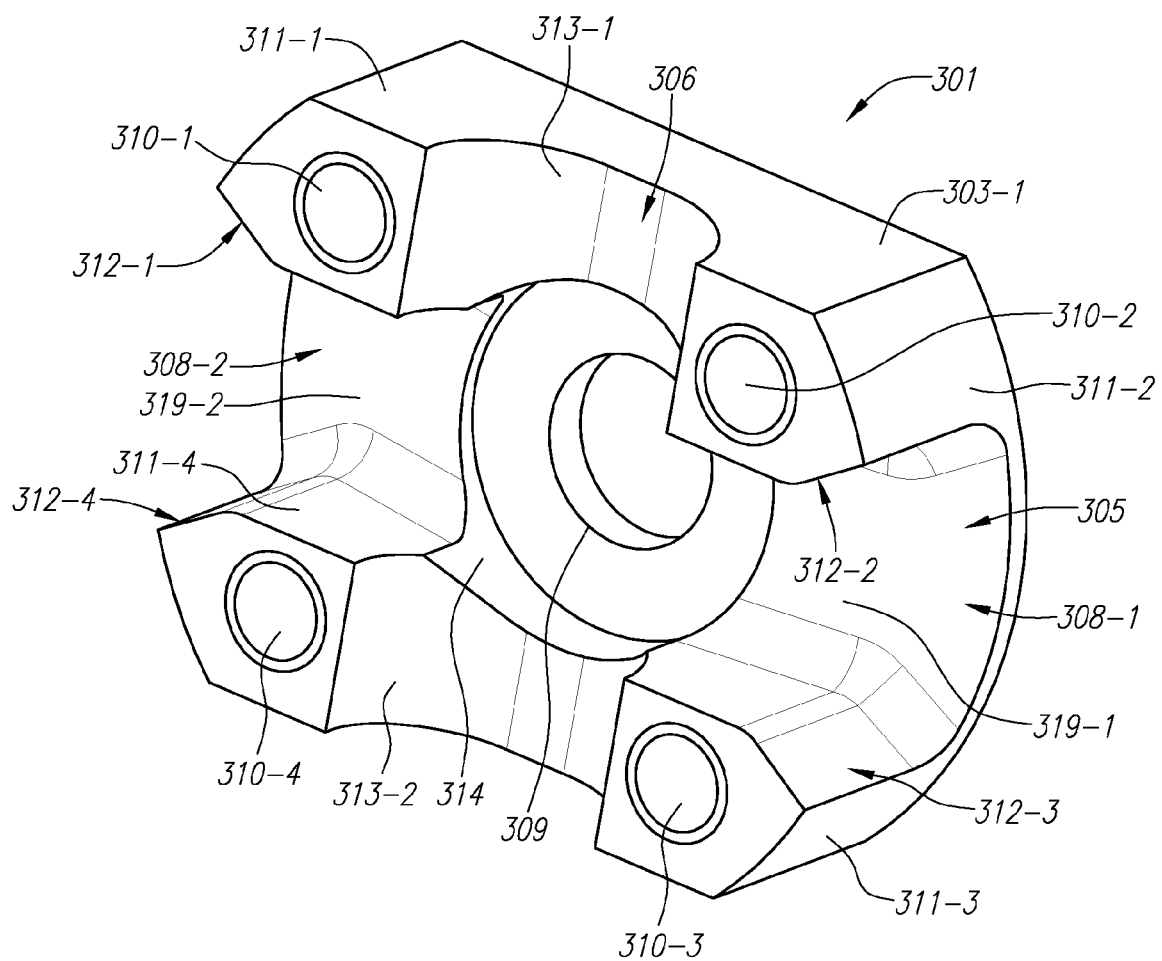
FIG. 19D is a perspective view of the upper side of an example embodiment of the inner housing of a fixed connector.
Figure 19E:
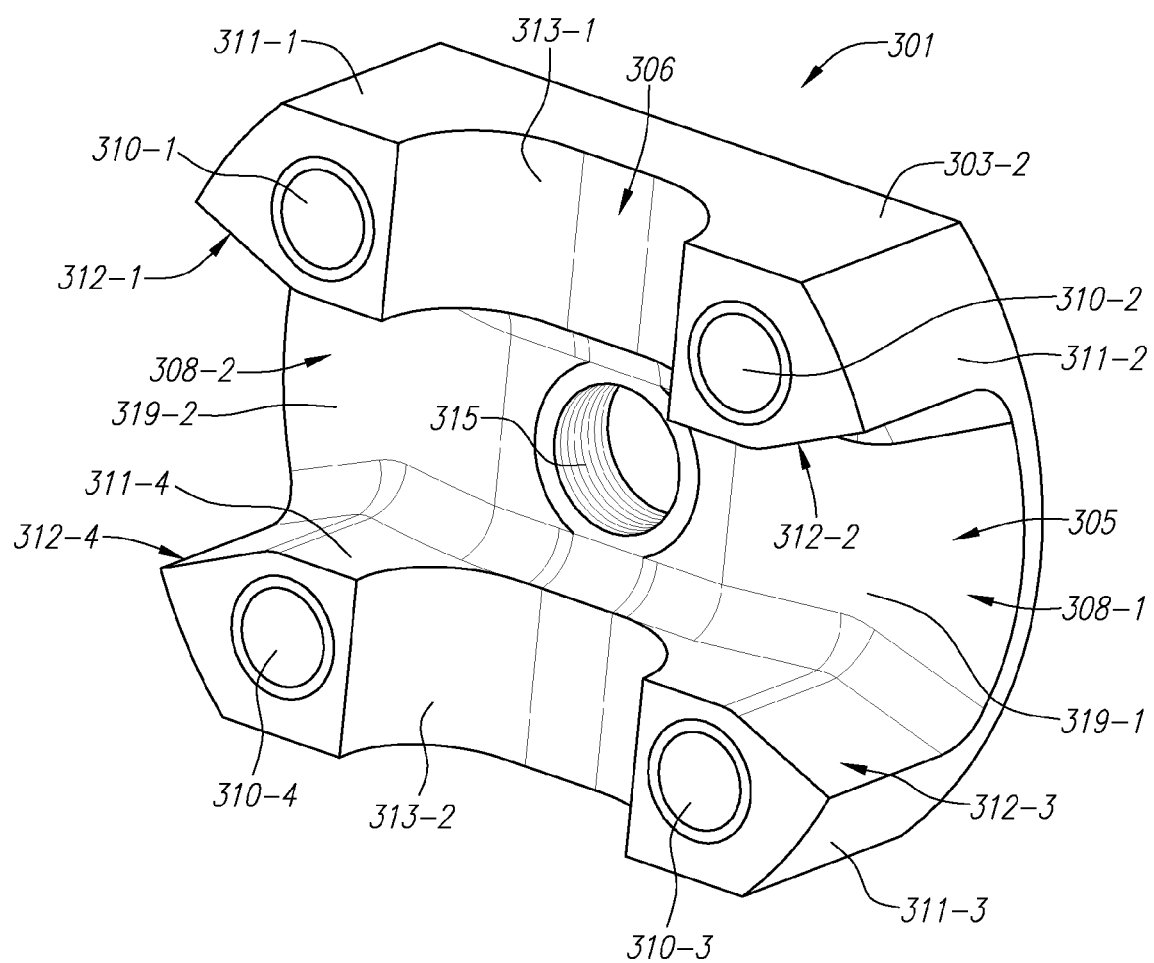

FIG. 19D is a perspective view depicting an example embodiment of inner housing 303-1, which is preferably configured for placement on a first side of the patient's spinous process. FIG. 19E is a perspective view depicting a second inner housing 303-2 configured for placement on the opposite side of the patient's spinous process. Inner housings 303-1 and 303-2 can each be coupled with the spinous process separately or, as depicted here, can be configured to couple together through one or more surgically created lumens in the patient's spinous process. Inner housing 303-1 includes a through-hole 309 through which a retaining element (not shown), such as a threaded bolt, can be placed. The threaded bolt is preferably inserted into through-hole 309 and then through the lumen in the patient's spinous process. The threaded end of the retaining element is preferably screwed into a threaded lumen 315 in the opposing inner housing 303-2 as shown in FIG. 19E. The retaining element preferably has a retaining head larger than through-hole 309 such as to reside in recess 314 and retain inner housing 303-1. One of skill in the art will readily recognize that multiple different types of retaining elements can be used including but not limited to clamps, screws and the like.

It should be noted that through-hole 309 and threaded lumen 315 are preferably centrally located on inner housings 303-1 and 303-2. If multiple retaining devices are used, then the corresponding apertures within inner housings 303 are preferably positioned symmetrically. Configuration in these manners allows the retaining force to be uniformly applied over the inner housing and reduces the risk that a non-uniformly applied retaining force will allow housing 303 to become dislodged in the region where the retaining force is weakest.

If only one rod is used in system 100, then inner housing 303-1 can be coupled only to the spinous process and not an opposing inner housing. Regardless of the number of housings, each can be coupled to the spinous process in any desired manner including, but not limited to, the manners of those other embodiments described with respect to FIGS. 4A-12D herein.

Inner housings 303-1 and 303-2 each have a generally platelike base from which four projections or projecting segments extend, generally at each of the four corners of the plate. Each inner housing 303 is preferably sized and configured according to the dimensions of the vertebral body to which it is intended to be attached. The underside of the planar base can be coated with a cushioning material or a material designed to conform to the surface texture of the spinous process. Each projection 311 includes a lumen 310, which is preferably used for coupling with outer housing 304 (not shown in FIGS. 19D-E). As shown here, a U-shaped, parabolic, or semicylindrical, recess 313 is positioned laterally on opposite sides of inner housing 303 and form the lower portion of lumen 306 through which axle member 302 is routed.

Spaced regions, or recesses, 319-1 and 319-2, which are shown on the superior and inferior sides of inner housing 303-1 and 303-2, together form the lower portion of rod lumen 305. Projections 311 each have a tapered surface 312 adjacent recess 319 that promotes pivoting of rod 102 (not shown) within lumen 305. These tapered surfaces 312 are positioned near the periphery of housing 303 and the degree to which surfaces 312 taper can, in part, be used to adjust the desired amount of pivoting of rod 102. Also shown here are tapered inner base surfaces 308-1 and 308-2 within recesses 319-1 and 319-2, respectively, which facilitate pivoting of rod 102 in the coronal plane as previously described.

Figure 19F:
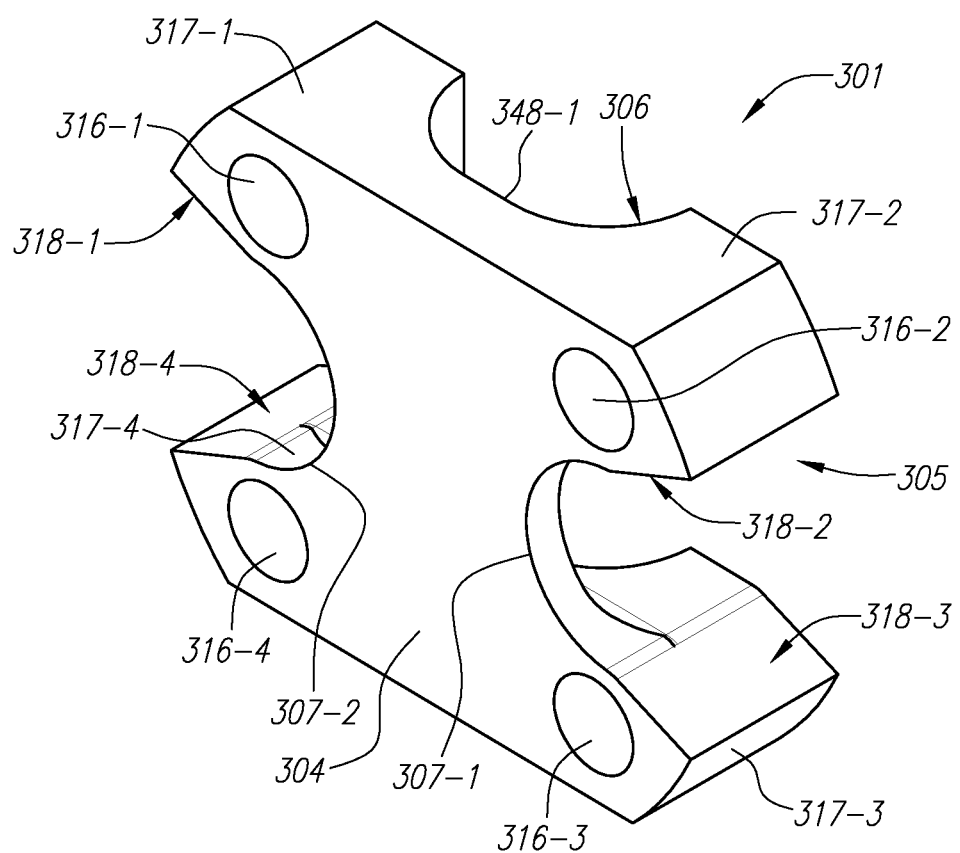
FIG. 19F is a perspective view of the upper side of an example embodiment of the outer housing of a fixed connector.
Figure 19G:
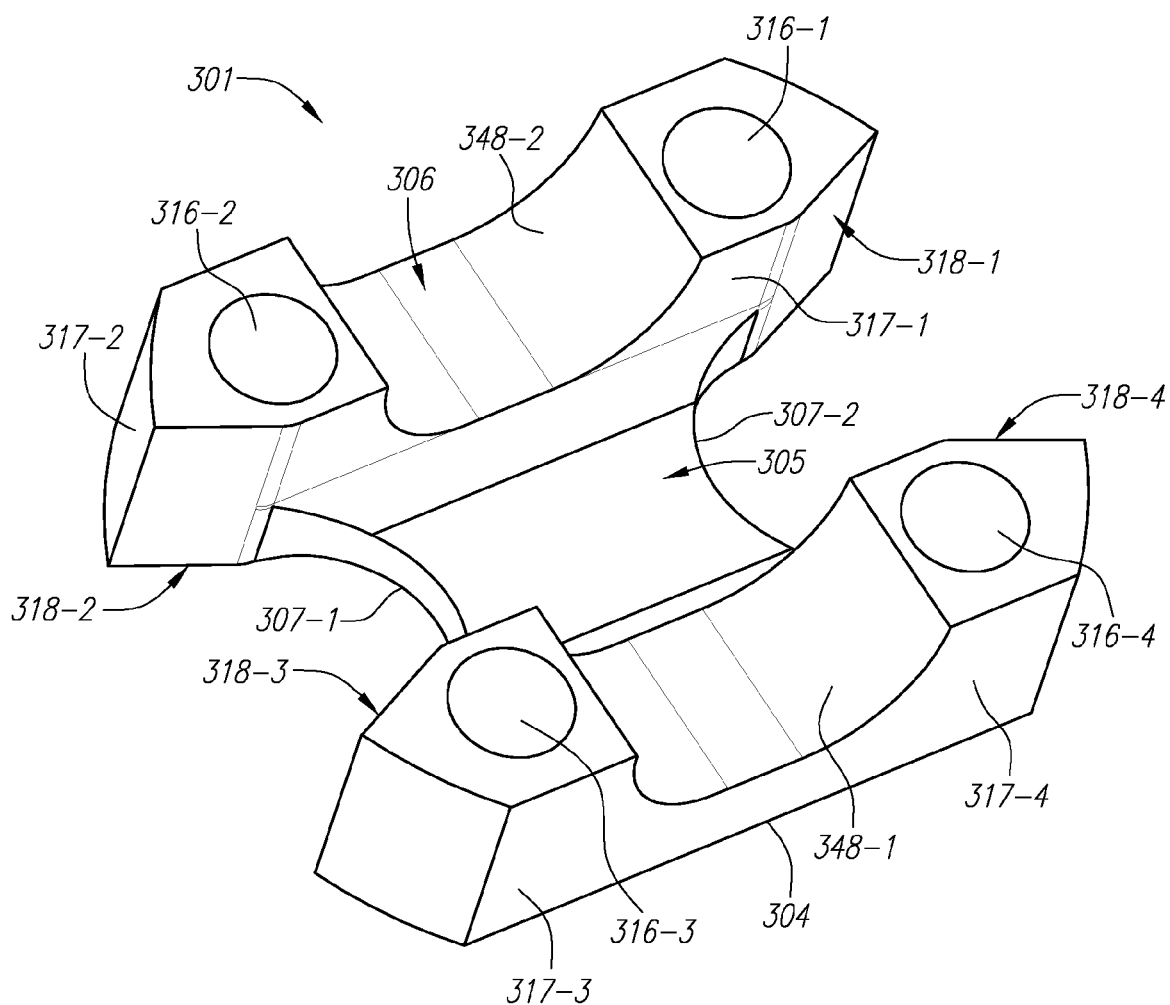
FIG. 19G is a perspective view of the lower side of an example embodiment of the outer housing of a fixed connector.

FIGS. 19F-G are perspective views of outer housing 304, which can be used with either embodiment of inner housing 303-1 and 303-2. Here, outer housing 304 includes a generally platelike base portion with four projections 317 extending generally from the four corners of the housing 304. The projections 317 and upper interior surface of housing 304 together define the upper portion of lumen 305. Each projection 317 includes a lumen 316, which can be used to receive a retaining device to couple outer housing 304 with either of inner housings 303-1 and 303-2. For instance, lumen 310 can be threaded and a screw-like or bolt-like retaining device can be inserted through lumen 316 and into the corresponding lumen 310 of inner housing 303 in order to screw the housings 303 and 304 together. One of skill in the art will readily recognize that many different manners of attachment can be used to couple housings 303 and 304 together including, but not limited to, clamps, snaps, clips, adhesives and the like. Similar to inner housing 303, outer housing 304 also includes an inner tapered surface 318, which can match the tapered surface 312 on inner housing 303. Outer housing 304 also includes U-shaped, parabolic or semicylindrical recesses 307-1 and 307-2. Also, outer housing 304 includes lateral U-shaped or semicylindrical recesses 348-1 and 348-2, which end beneath the upper surface of housing 304 and form the upper portion of axle lumen 306.

Figure 20A:
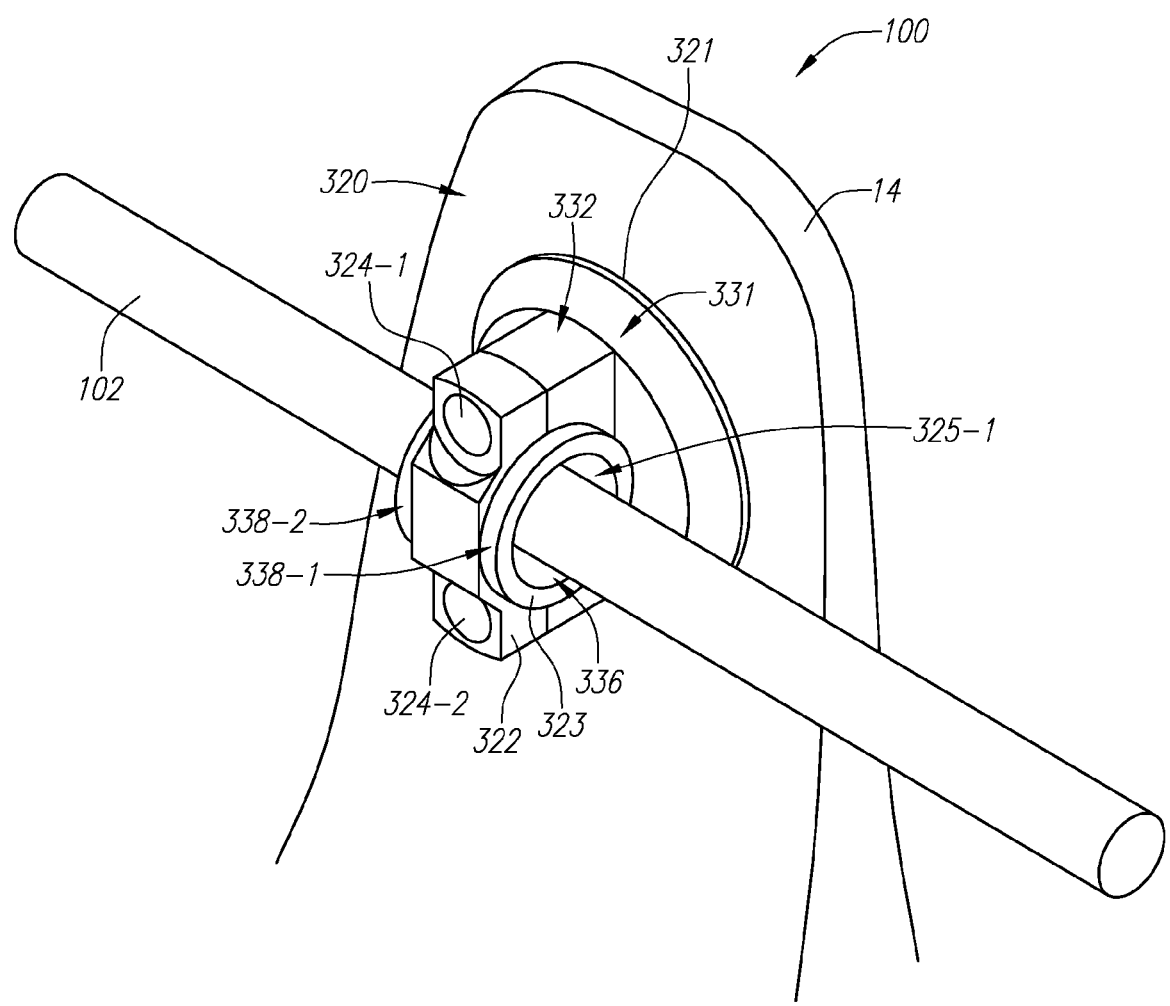
FIG. 20A is a perspective view of an example embodiment of a slidable connector coupled to a spinous process.

FIG. 20A is a perspective view depicting an example embodiment of slidable connector 320 coupled with a spinous process 14 and having rod 102 routed therethrough. Here, slidable connector 320 includes an inner housing 321 and an outer housing 322 with a tubular housing, or bushing 323, coupled between both housings. Inner housing 321 includes a base portion 331 and a bushing support portion 332. Inner housing 321 and outer housing 322 are connected together with retaining devices (not shown) routed through lumens 324-1 and 324-2 of outer housing 322 and corresponding lumens (not shown) in inner housing 321. As described above, the retaining device can be, for instance, configured as a screw that is received within a threaded lumen in inner housing 321. Bushing 323 includes an inner lumen 336 having sloped surfaces that permit rod 102 to pivot therein. Here, the sloped surface 325-1 present on the near side of bushing 323 is shown. Bushing 323 also includes enlarged diameter portions 338-1 and 338-2, which will be described in more detail herein.

Figure 20B:
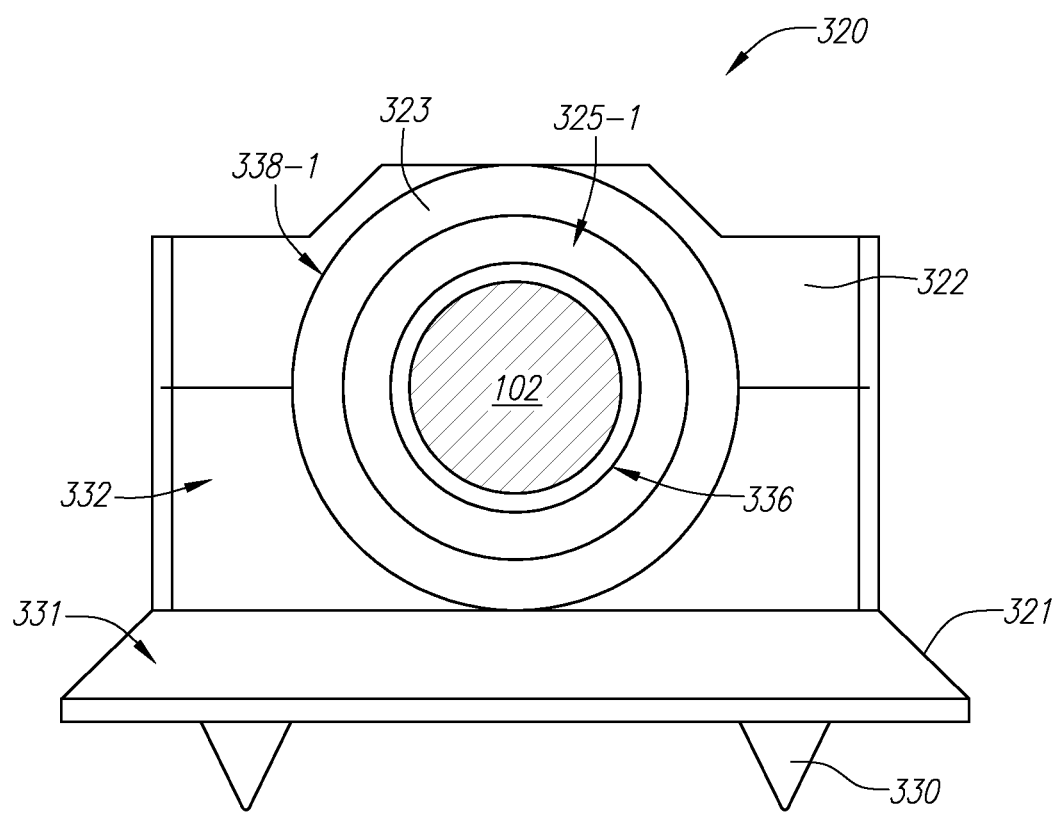
FIG. 20B is an end-on view of an example embodiment of a slidable connector.

FIG. 20B is a side view of slidable connector 320 with rod 102 routed through lumen 336. As can be seen here, the diameter of rod 102 is preferably undersized with respect to the inner diameter of lumen 336. This intervening free space, in combination with sloped surfaces 325, allows rod 102 to pivot in the coronal and sagittal planes. It allows rod 102 to rotate about its longitudinal axis, although this rotation is limited by fixed connector 301 (and/or limitations to the range of motion of the patient). This free space also allows rod 102 to move laterally, e.g., side-to-side translation, in the coronal plane, by a limited degree. In addition, this free space reduces the friction between rod 102 and the inner surface of bushing 323, facilitating the ease to which rod 102 can slide longitudinally through lumen 336. This can improve the patient's mobility and can also facilitate initial implantation of the rod and/or system itself. Additionally, this can provide the advantage of reducing the risk that the rod will become seized, caught or otherwise stuck in the slidable connector, which can result in the loading of undesired moments on the spinous process(es).

Figure 20C:
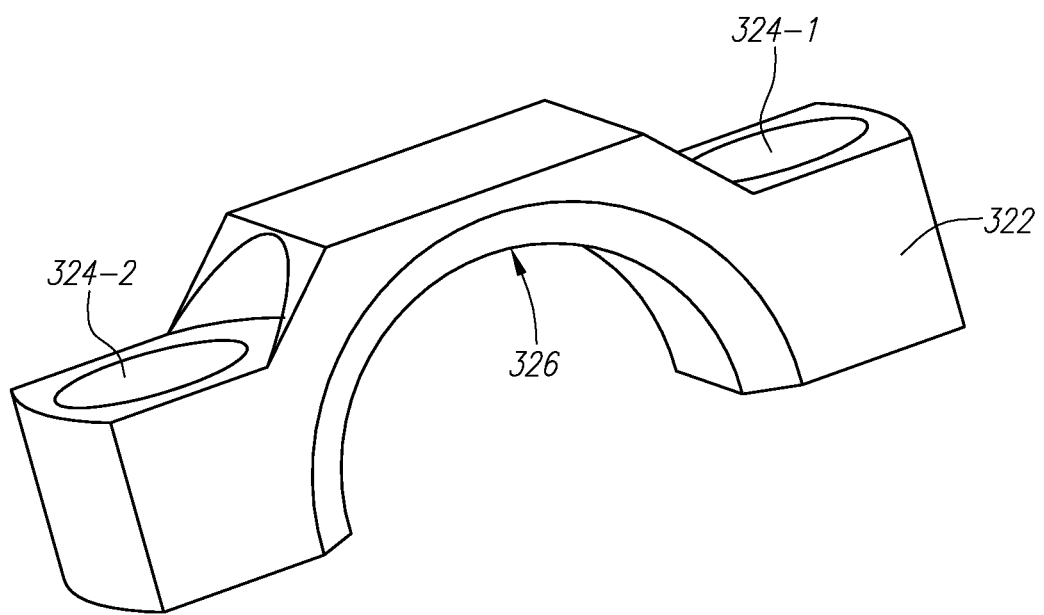
FIG. 20C is a perspective view of an example embodiment of the outer housing of a slidable connector.
Figure 20D:
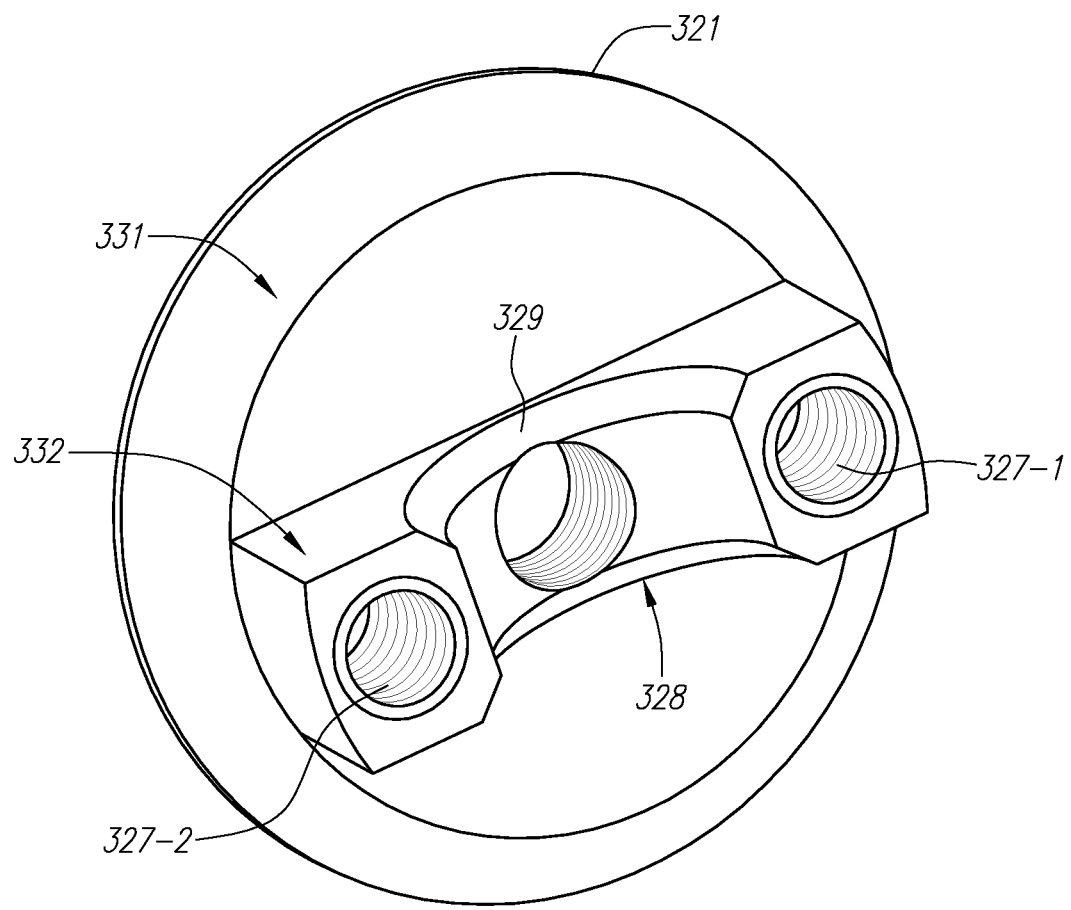
FIG. 20D is a perspective view of the upper side of an example embodiment of the inner housing of a slidable connector.
Figure 20E:
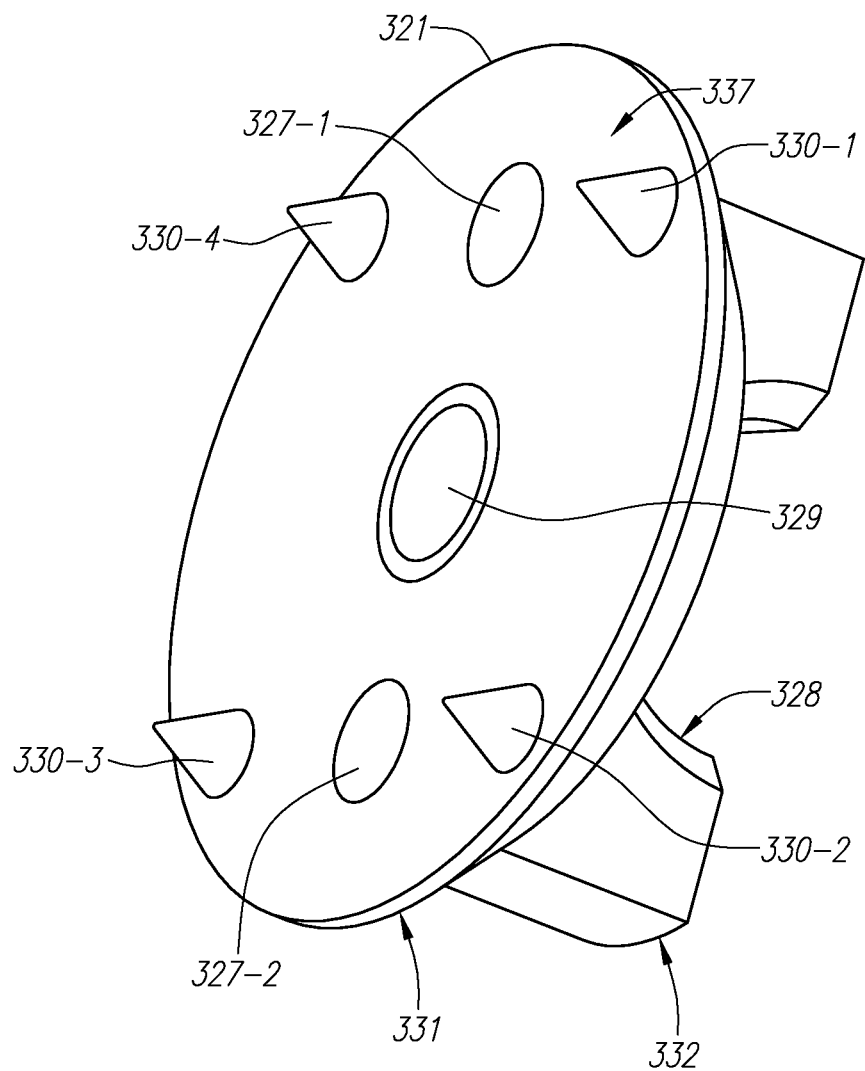
FIG. 20E is a perspective view of the lower side of an example embodiment of the inner housing of a slidable connector.
Figure 20F:
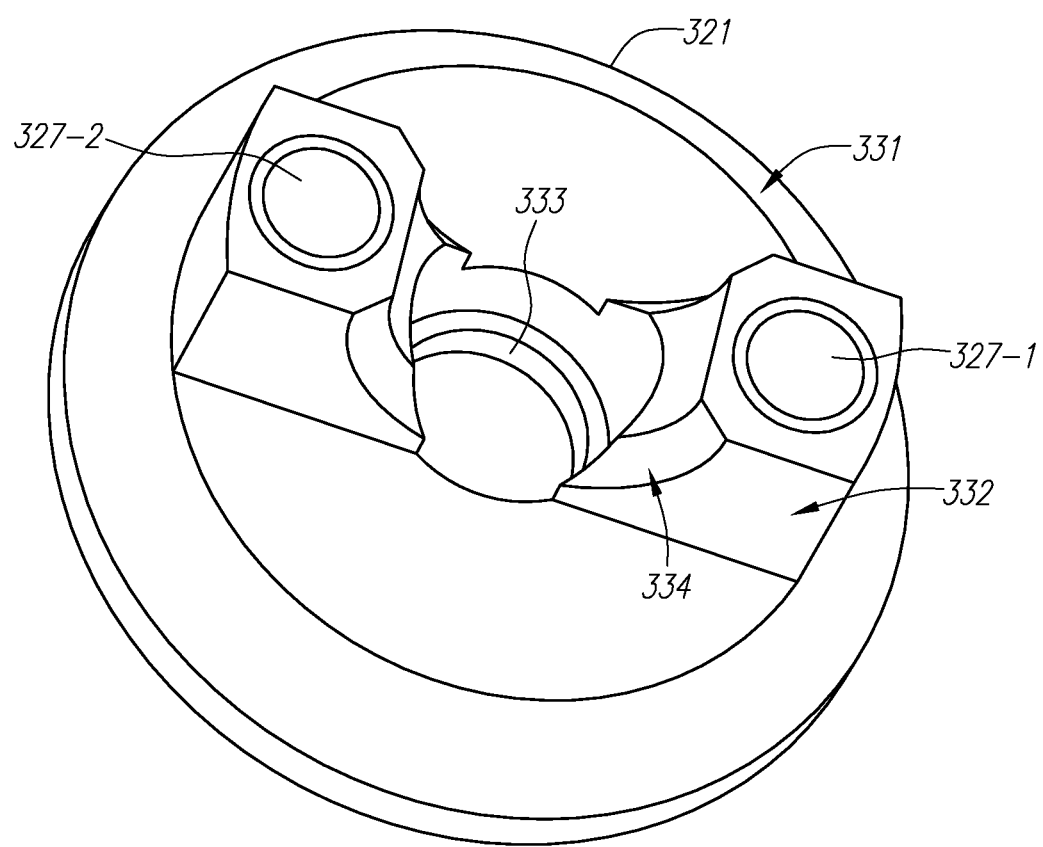
FIG. 20F is a perspective view of the upper side of another example embodiment of the inner housing of a slidable connector.
Figure 20G:
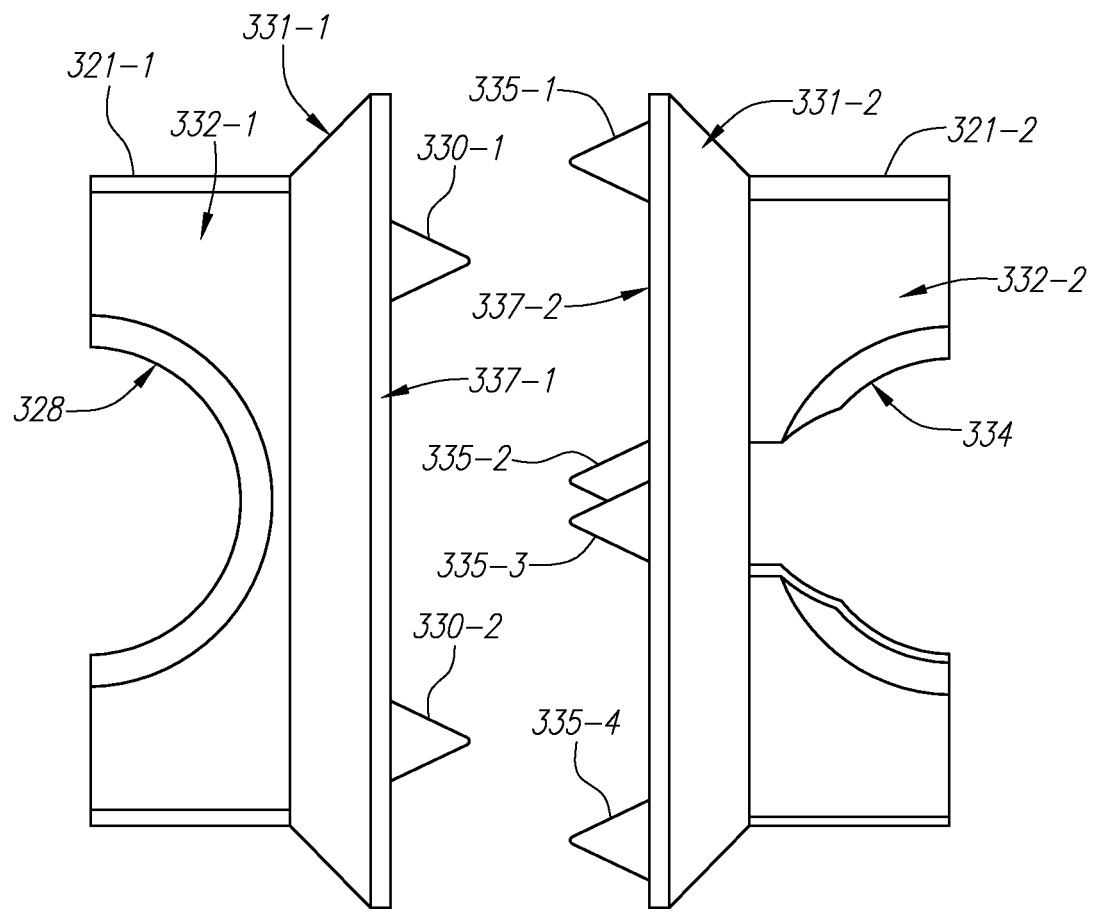
FIG. 20G is an end-on view of example embodiments of the inner housing of a slidable connector.
Figure 20H:
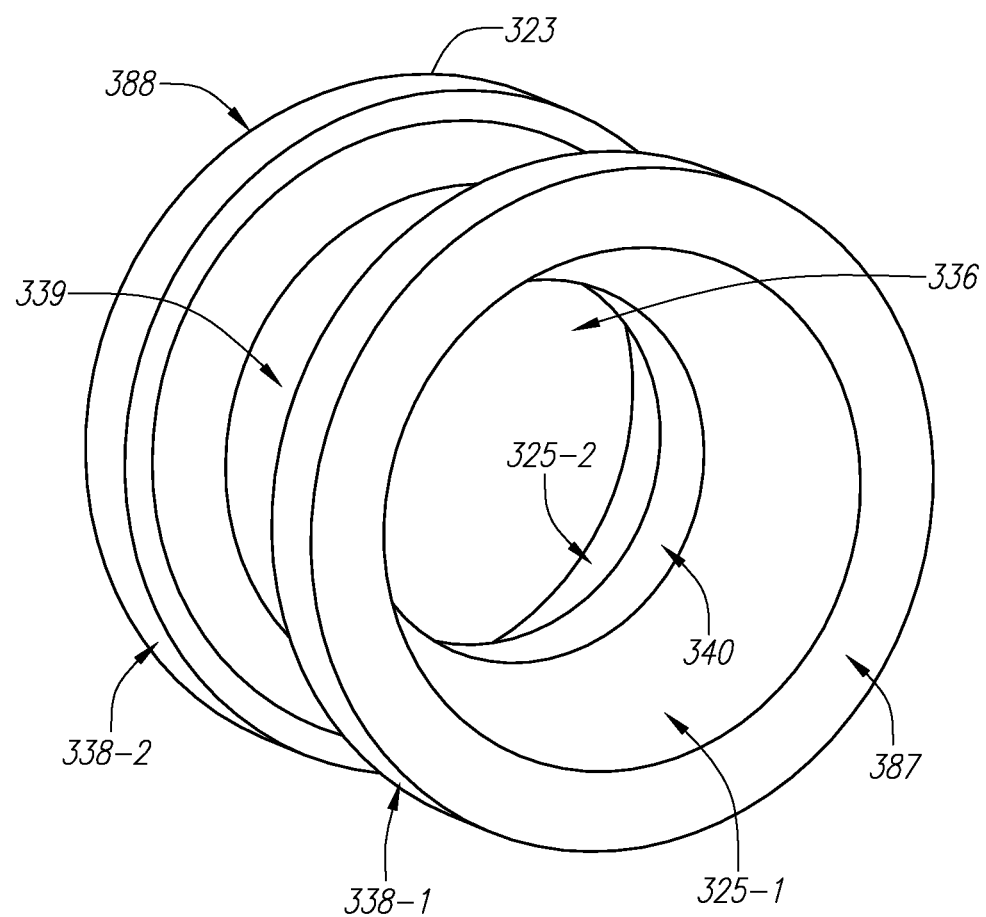
FIG. 20H is a perspective view of an example embodiment of a tubular housing of a slidable connector.
Figure 20I:
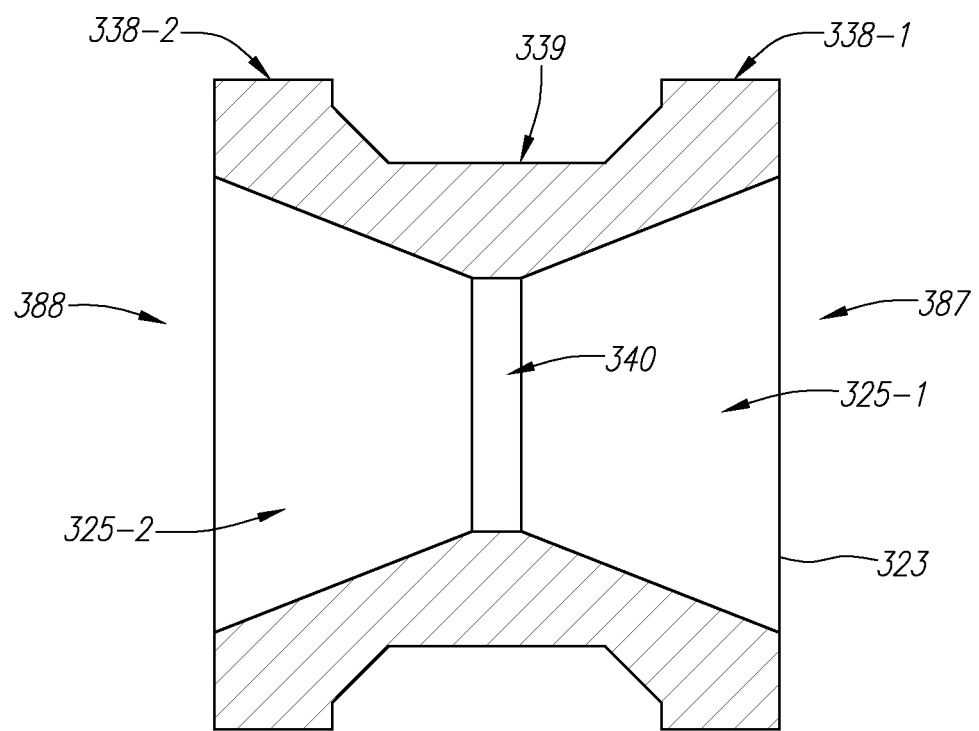
FIG. 20I is a longitudinal cross-sectional view of an example embodiment of a tubular housing of a slidable connector.

Sloped surfaces 325 are shown in greater detail in the perspective view of bushing 323 depicted in FIG. 20H and in the longitudinal cross section of FIG. 20I. Here, it can be seen that lumen 336 includes a first sloped surface 325-1 that extends from a first end 387 of bushing 323 toward the center of bushing 323, such that lumen 336 decreases in diameter. An intermediate surface 340 is present in the central region of lumen 336 and has a generally flat, unsloped surface. On the opposite side of bushing 323 is a second sloped surface 325-2 that slopes from end 388 toward intermediate surface 340 such that lumen 336 decreases in diameter. The degree to which surfaces 325 slope, as well as the extent to which the diameters of rod 102 and lumen 336 differ, determine the degree to which rod 102 can pivot within slidable connector 320.

Although rod 102 can preferably freely rotate within lumen 336, slidable connector 320 and/or rod 102 can be configured, if desired, to prevent or limit such rotation. For instance, rod 102 can have a fixed longitudinal feature that interfaces with a complementary feature in slidable connector 320 that prevents rod 102 from rotating. It should be considered that prevention of all rotation with respect to the slidable connector would load the spinous process with a moment, which can be undesirable.

Bushing 323 formed or coated with a lubricious polymeric material, such as PEEK and the like, or a polymer impregnated with lubricious material, such as tetrafluoroethylene (TFE) and the like. Bushing 323 can also be formed from ceramic materials. If coated, bushing 323 can be formed from any rigid material such as nitinol, stainless steel, titanium, elgiloy and the like. Other coatings can include diamond-based coatings, titanium nitride and the like. The surface of bushing 323 can also be treated to reduce friction, such as by electro-polishing. These coatings and surface treatments can likewise be applied to rod 102.

Bushing 323 is preferably held in a secure manner between inner and outer housings 321 and 322 by enlarged diameter portions 338-1 and 338-2. An intermediate portion 339 of bushing 323, having a smaller diameter than portions 338, is configured to be received within recesses of inner and outer housings 321 and 322. FIG. 20C is a perspective view depicting an example embodiment of outer housing 322. Shown here is semicircular recess 326, which is configured to receive the intermediate portion 339 of bushing 323. Recess 326 can have any shape suitable to retain bushing 323.

FIG. 20D is a perspective view of inner housing 321 with base 331 and bushing support portion 332. Base 331 can have flared edges to provide an atraumatic interface with the surrounding tissue Inner housing 321 includes a threaded lumen 329 configured to receive a retainer device in a manner similar to that described with respect to fixed connector 301. The retainer device can couple directly to the spinous process 14 or to another inner housing 321 located on the opposite side of the spinous process. Also shown here is semicircular recess 328, which is configured to align with semicircular recess 326 of outer housing 322 to form a channel in which intermediate portion 339 of bushing 323 can be retained. Also shown are lumens 327-1 and 327-2, which preferably align with the corresponding lumens 324 in outer housing 322. Lumens 327-1 and 327-2 are preferably threaded to accept a screw or other retainer inserted through lumen 324.

FIG. 20E is a perspective view of the underside of inner housing 321. Underside surface 337 includes multiple engagement features, configured here as bone anchors 330-1 through 330-4. Each bone anchor, in this embodiment, is configured as a conical abutment, or spike, and is configured to be inserted into the spinous process to facilitate the anchoring and securement of inner housing 321 thereto.

FIG. 20F is a perspective view of an example embodiment of a second inner housing 321 for slidable connector 320, for use in an embodiment where two slidable connectors 320 are coupled to opposite sides of a single spinous process. This embodiment is generally similar to that described with respect to FIGS. 20D-E, with the exception that a through-hole 333 is present instead of a threaded lumen. Through-hole 333 can receive, for example, the head of a retaining device such as a screw that is retained by the sloped surfaces of through-hole 333 such that the retainer can securely couple with this inner housing and extend through a surgically created opening in the spinous process to the opposite inner housing. Also shown here is semicircular recess 334, which includes an optional cutaway portion configured to accommodate the head of the retaining device.

FIG. 20G is a side view of the example embodiments of inner housing 321 described with respect to FIGS. 20D-F positioned opposite each other in a manner suitable for attachment to the spinous process. Here, inner housing 321-1 corresponds to that described with respect to FIGS. 20D-E, and inner housing 321-2 corresponds to that described with respect to FIG. 20F. It can be seen that bone anchors 330 on inner housing 321-1 and bone anchors 335 on inner housing 321-2 are offset from each other so as to evenly distribute the force applied by the anchors onto the spinous process. This can minimize the risk that the spinous process will fracture. Here, bone anchors 330-1 and 330-2 are two of the four bone anchors that are visible (see FIG. 20E). Each bone anchor 330 and 335 is preferably located equidistant from each other bone anchor on the same housing. Also, the bone anchors on one inner housing are preferably positioned to achieve the maximum offset from the points of contact of the bone anchors on the opposite inner housing.

For instance, bone anchors 330 on inner housing 321-1 are located near the outer edge of the underside surface and at 90-degree radial intervals (i.e., 45 degrees, 135 degrees, 225 degrees and 315 degrees about the periphery of inner housing 321-1). Bone anchors 335 are also preferably positioned near the outer edge of the underside surface and at 90-degree radial intervals, but offset by 45 degrees from the bone anchors 330 (i.e., bone anchors 335 are at 0 degrees, 90 degrees, 180 degrees and 270 degrees about the periphery of inner housing 321-2). Of course, the spacing and arrangement is dependent upon the number and size of the anchors. Other nonuniform or asymmetric configurations can also be used depending on the needs of the application and/or the structure of the bone anchor or equivalent feature. It should be noted that a textured surface can be used instead of discrete bone anchors 330 and 335. That textured surface can extend about the entirety of or any portion of the underside surface 337 of each inner housing.

The embodiments of the fixed and slidable connectors 301 and 320 described herein generally include an inner and outer housing where the outer housing is described as connecting to the inner housing from a lateral (e.g., left-to-right, right-to-left) direction. Lateral attachment requires the surgeon to have relatively more access to the lateral side of the spinous process, which requires relatively more invasive surgery. Alternatively, each of these embodiments can be configured such that the outer housing connects to the inner housing from a posterior-to-anterior direction. Attachment of housing 343 to housing 342 in the posterior-to-anterior direction allows the surgeon (or other medical professional) to create a smaller surgical cavity around the spinous process since the surgeon is not required to position and attach the housings together laterally.

Figure 21:
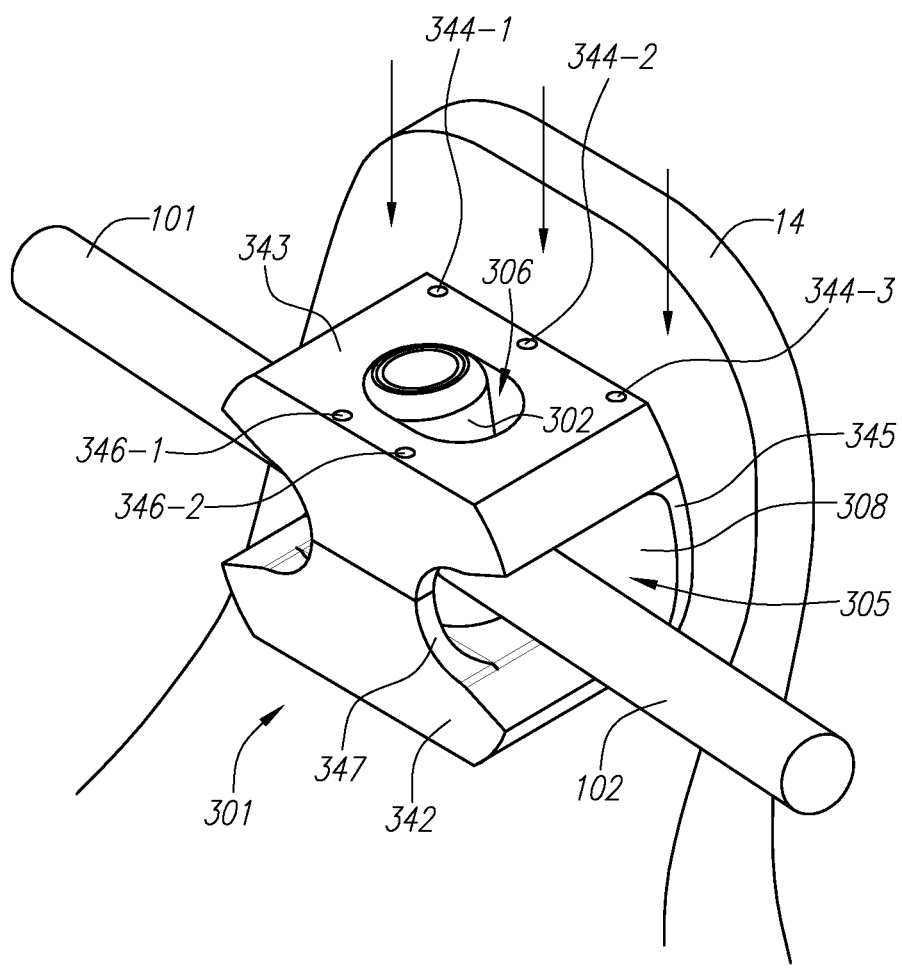
FIG. 21 is a perspective view of another example embodiment of a slidable connector coupled to a spinous process.

FIG. 21 is a perspective view of an example embodiment of fixed connector 301 coupled with spinous process 14. Here, fixed connector 301 includes an inner/lower housing 342 and an outer/upper housing 343 that is configured to be coupled with lower housing 342 in the posterior-to-anterior direction indicated here by the arrows. Multiple lumens 344-1 through 344-3 are present to accept a retaining device that couples with the inner edge plate 345 of lower housing 342. Similar lumens 346-1 and 346-2 are present on the opposite side of the device and are configured to allow a retaining device to couple with outer plate 347 of inner housing 342. Similar to the embodiments described previously, a suitable retaining device in this example can be a threaded screw or a bolt, although one of the skill in the art will readily recognize that other retaining devices can be used.

The embodiments described with respect to FIGS. 18-21 provide the advantage of allowing the rod (or other corrective device) to move with respect to the spinous processes to alleviate any moments that are created on the spinous processes as a result of the patient's movement, iterative correction caused by the device, or even during implantation. Because these embodiments guide the motion of the rod itself, and preferably do not rely on an intermediate moving device or mechanism to allow for motion, and move with the rod, the efficiency of the system is greatly enhanced. The elimination of any intermediate (or intervening) moving part increases the efficiency and reliability of the system and allows the system to achieve an overall lower profile, which can translate into less discomfort to the patient and can require less invasive surgery during implantation. Alternatively, the axle member can be integrated directly into the connector such that the axle member may be considered a moving part of the connector, with the rod coupled to the axle member. In such an instance, the axle member is shared between the rod and the connector. Nevertheless, some or all of the advantages of these embodiments persist (e.g., as compared to Rivard U.S. Pat. No. 6,554,831). The operation and configuration of the system can remain substantially the same, and the system can still achieve an overall lower profile with increased reliability.

These embodiments relieve moments centered (or focused) about the rod itself, as opposed to introducing a fixed intermediate connector to the rod and attempting to relieve moments around that intermediate connector (see, e.g., Rivard U.S. Pat. No. 6,554,831). For instance, the slidable connector can allow the rod to directly pivot a limited amount in the coronal plane as opposed to pivoting about the end of an intermediate connector. Also, the fixed connector can allow pivoting of the rod in both the coronal and sagittal planes around the rod itself, as opposed to the end of an intermediate connector.

Figure 22A:
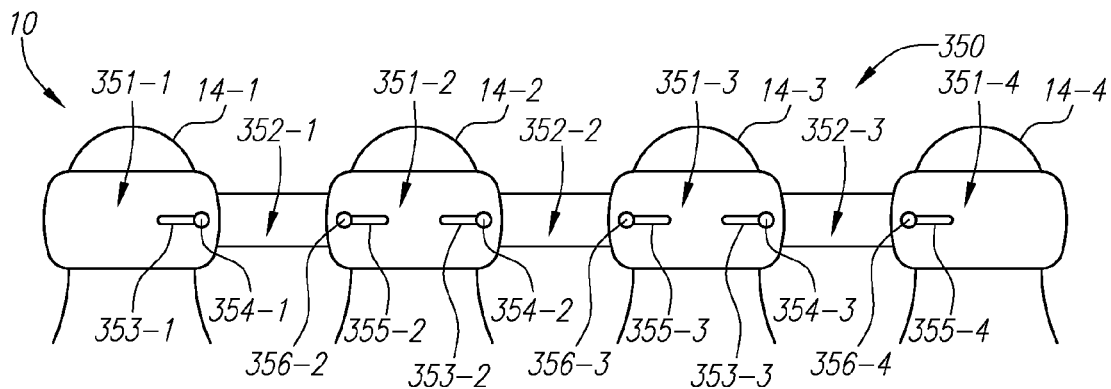
FIGS. 22A-C are side views of another example embodiment of a treatment system in various states.
Figure 22B:
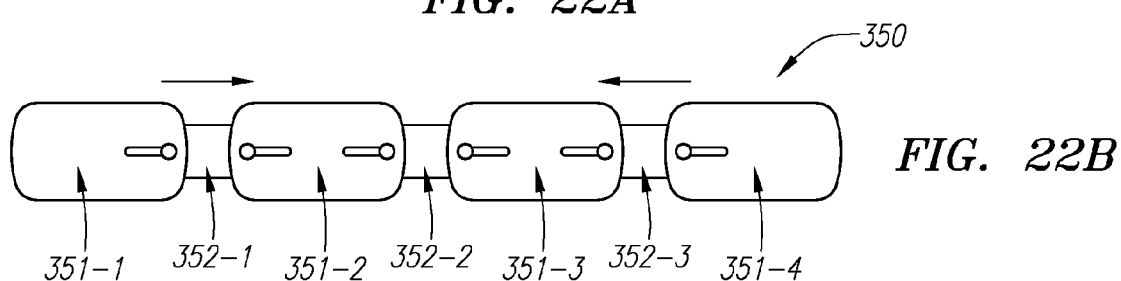
Figure 22C:
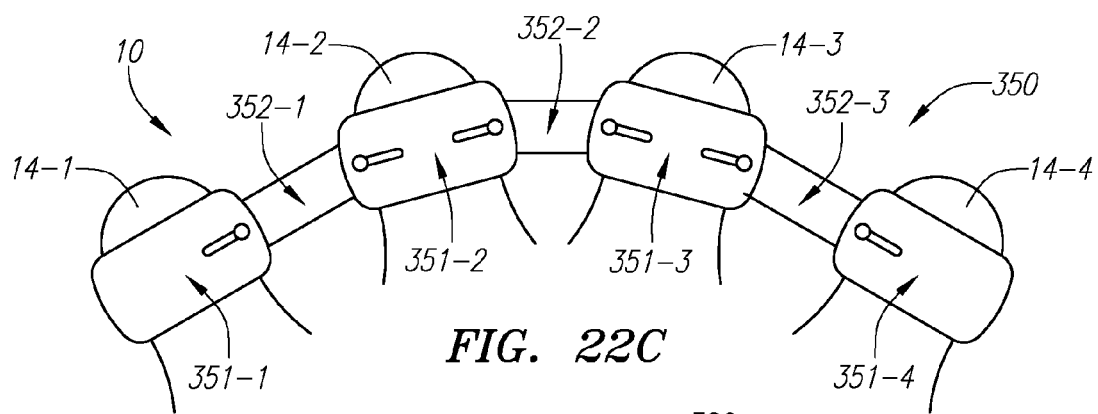

FIGS. 22A-K depict example embodiments of a link-based correction system 350. System 350 preferably includes a plurality of links that interface with one or more adjacent links to provide limited freedom of motion in the sagittal plane while at the same time restricting motion and applying corrective force in the coronal plane. FIGS. 22A-C are side views depicting a first example embodiment of system 350. Here, system 350 includes multiple outer links 351 (only one shown) each coupled to one or more inner links 352. Outer link 351 preferably includes a longitudinal slot 353 in which an elongate guide element (e.g., a pin) 354 can be placed. Guide element 354 is preferably routed through both outer link 351 and inner link 352-1, so as to couple the two links together and serve as an axle for limited pivoting motion and as a guide for translational motion through slot 353-1. Guide element 354 preferably has an enlarged head to retain element 354 with respect to links 351 and 352. A similar arrangement is present with slots 355 and guide elements 356, which are used to couple inner link 352-1 with a second adjacent outer link 351 (not shown).

Figure 22D:
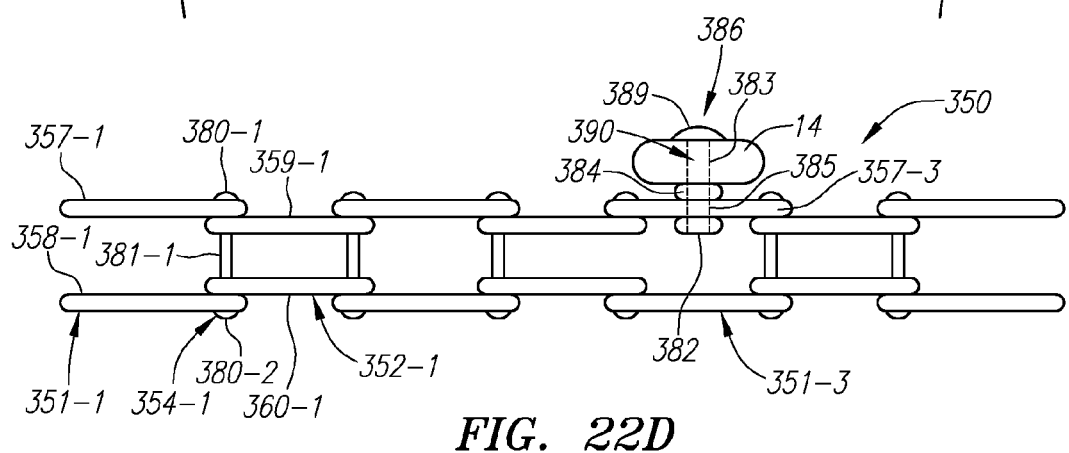
FIG. 22D is a top-down view of another example embodiment of a treatment system.

FIG. 22D is a top-down view of this chain-like system 350 showing outer links 351 coupled to inner links 352 by guide elements 354. Here, outer links 351 include two plates 357 and 358 and, likewise, inner links 352 include two plates 359 and 360. Each plate is preferably polygonal with rounded edges and, when viewed from the perspective of being coupled alongside a spinous process, generally has a length (measured superiorly inferiorly) that is greater than a width (measured posteriorly anteriorly), which, in turn, is greater than a thickness (measured laterally). The plates 202 and 204 can also be described as planar members, elongate members or strut-like members. In this and the other embodiments of link-based systems described herein, relatively short rods can be used instead of plates.

Guide element 354 preferably includes enlarged head portions 380-1 and 380-2 located on the exterior surfaces of plates 357-1 and 358-1, respectively. Guide element 354 also preferably includes an elongate shaft extending between head portions 380. Shaft 381 preferably has a relatively wider central section that retains the opposing plates of links 351 and 352 in spaced relation to each other. Alternatively, a central strut can be positioned between plates 357 and 358 (or 359 and 360) to maintain those plates in spaced relation to each other. Also, only one plate can be used provided that the plate is sufficiently rigid to exert the desired amount of corrective force in the coronal plane. The guide element 354 can also be routed through a similar longitudinal slot in inner link 352 if desired, or, inner link 352 can include a round aperture for holding the guide element 354 in a relatively fixed position with relation thereto.

Here, outer link 351-3 is shown coupled with an adjacent spinous process 14. Only one such coupling is shown here although it should be noted that any number of one or more outer links 351 can be coupled with the adjacent spinous processes 14. An aperture 383 is surgically created in spinous process 14 in which a retaining (or engagement) device 386 can be routed. Retaining device 386 is configured as a threaded bolt 390 with an enlarged head 389. The threaded bolt 390 is coupled with an opposing nut 382 after bolt 390 is routed through the aperture 383 in the spinous process 14, an optional annular spacer 384 and a through-hole 385 in plate 357-3. Alternatively, system 350 can be coupled directly to another system 350 located on the opposite side of spinous process 14.

Referring back to FIG. 22A, outer links 351 are each preferably connected to an individual spinous process 14 with inner links 352 extending therebetween. The patient can have separate systems 350 implanted on either side of the spinal column or only one system 350 can be used. Also, instead of implanting system 350 on a single side of the spinal column, system 350 can be coupled directly on top of the spinous processes of the patient's spinal column. For instance, although not shown here, outer link 351 can be enlarged to fit on top of a spinous process 14 with sufficient room to allow movement of inner link 352 in relation thereto. Outer link 351 can then be secured to the spinous process in much the same way as described with respect to FIG. 22D below, or with respect to other embodiments discussed herein.

System 350 is preferably configured to allow translational movement between each link such that system 350 can expand and contract longitudinally, e.g., superiorly-inferiorly. FIG. 22A depicts system 350 in a generally expanded state, and FIG. 22B depicts system 350 in a contracted state where the ends of system 350 have been retracted toward each other as indicated by the arrows. Each link 351 can rotate about guide element 354 with respect to each adjacent link 352, allowing system 350 to bend in sagittal plane as needed. System 350 can also be configured to allow some twisting (e.g., between adjacent links) to follow a twist in the spine. FIG. 22C depicts an exaggerated view of system 350 coupled to a patient's spinal column 10 while that spinal column 10 is in a state of flexion. As can be seen here, the ability of system 350 to bend and to expand and contract longitudinally allows significant freedom of movement for the patient during flexion, and likewise during extension. The rigidity of system 350 in the coronal plane and the flexibility of system 350 in the sagittal plane allows the patient greater mobility while continuing to apply the desired corrective force. Preferably, the links are made of a bendable elastic material (e.g., polymeric materials, stainless steel) or superelastic material (e.g., a NiTi alloy such as nitinol), such that any deformation of the links in the coronal plane enacts a return force that can be used to correct the deformity. Alternatively, the links can be made fully rigid, such that there is no flexibility in the coronal plane.

Figures 22E, 22F:
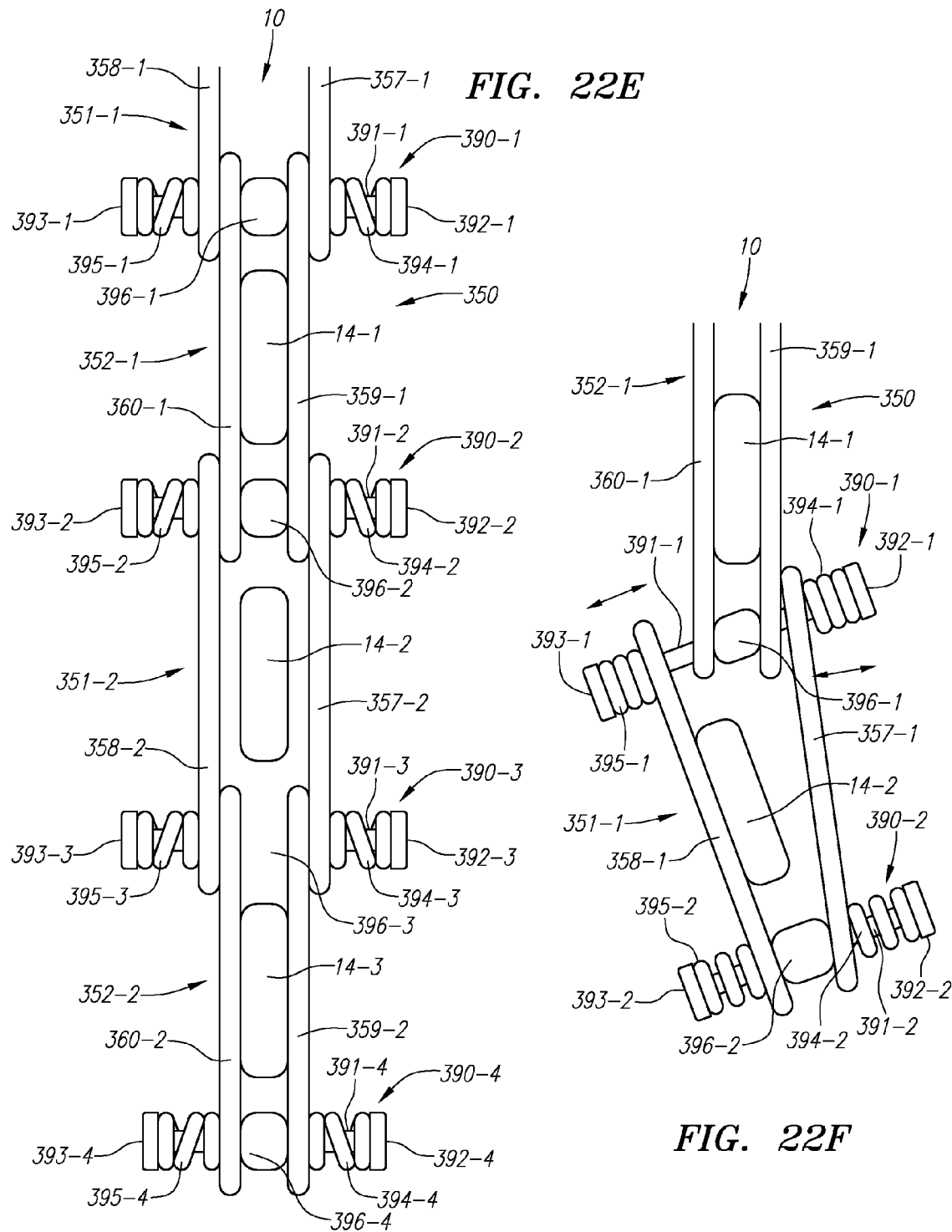
FIGS. 22E-F are posterior views depicting another example embodiment of a treatment system coupled with a corrected and deformed spinal column, respectively.
Figure 22G:
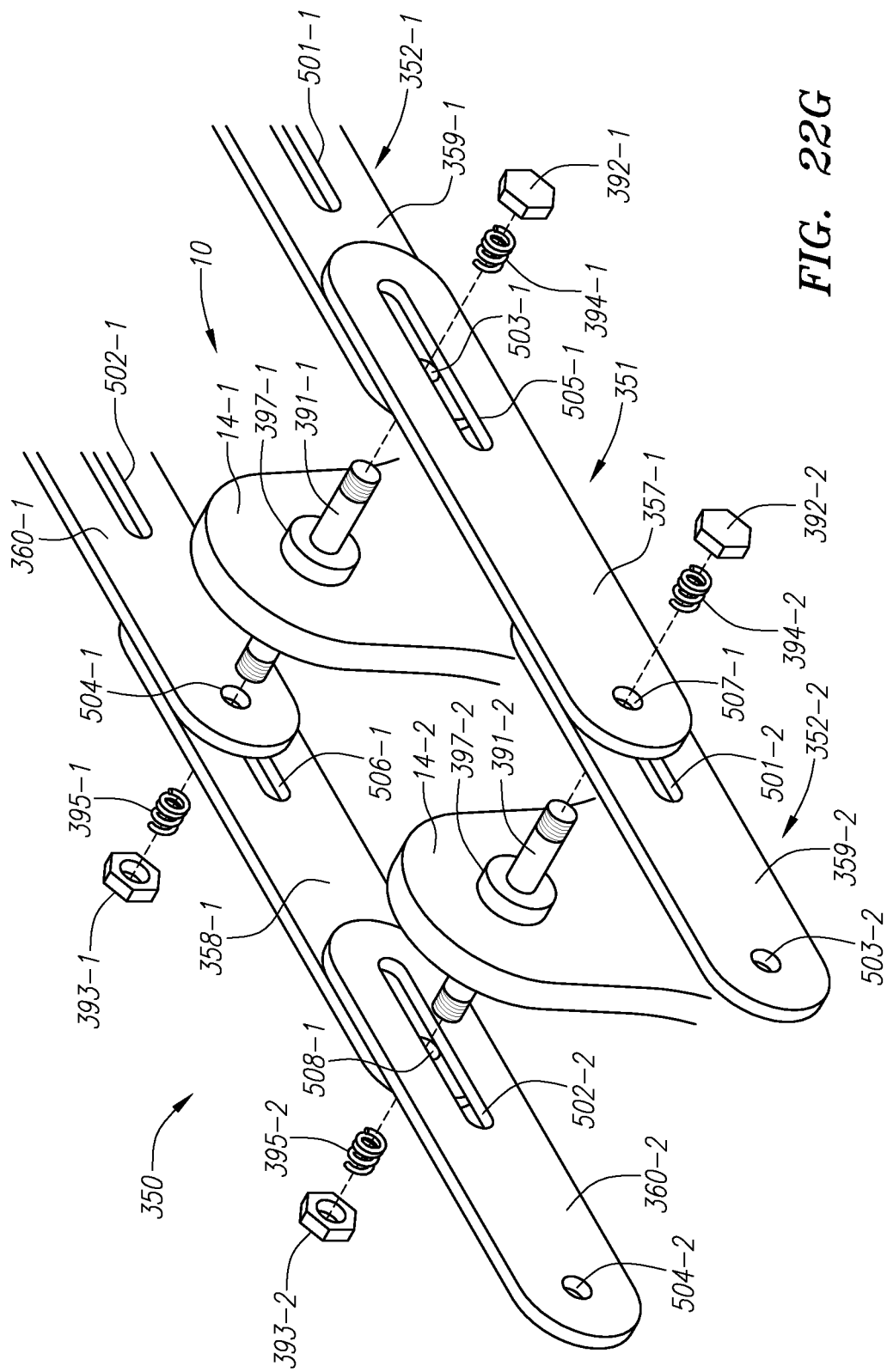
FIG. 22G is an exploded perspective view depicting another example embodiment of a treatment system coupled with a spinal column.

FIGS. 22E-G depict additional example embodiments of a link-based corrective system 350. In the embodiment of FIGS. 22E-F, system 350 is positioned over the spinous processes 14 such that each spinous process 14 lies between an opposing pair of linkage plates 357-358 or 359-360. Similar to the previous embodiment, system 350 includes outer links 351 and inner links 352. Each inner link 352 is coupled to one or more adjacent outer links 351 by an elongate guide element 391 that is configured here as an axle and is inserted through apertures and/or slots (such as those depicted in FIG. 22G) in both plates 357/358 of outer link 351 and plates 359/360 of inner link 352. Preferably, guide element 391 resides in at least one longitudinal slot present in both sides of the system (i.e., one slot in at least one of the outer plate and inner plate on both the left and right sides). The guide element can slide along the longitudinal slot allowing the links 351 and 352 to pivot laterally (in the coronal plane) and elongate to allow flexion and extension of the spine.

A spacer 396 is positioned over guide element 391 and located between the inner plates 359 and 360. Spacer 396 is preferably configured to match the width of the adjacent spinous processes 14 such that the plates are held in close proximity to, or in contact with, the respective spinous process. The spacer could be made from a metal alloy such as stainless steel or titanium alloy. It could also be made from a plastic such as PEEK or UHMWPE. Preferably, the spacer is substantially rigid to prevent the plates from applying excessive lateral force on the spinous processes. Spacer can be separate or integrated with guide element.

Guide element 391 preferably includes a retaining element 392/393 on each end. Between each retaining element 392/393 and the adjacent plate 357/358 is positioned a bias element 394/395, respectively. The bias element 394/395 is shown here to be in the form of a coil spring capable of exerting an expansive force between the retaining element 392/393 and the respective adjacent plate 357/358 (or 359/360). The coil spring is preferably conical to allow the spring to achieve a lower profile upon collapse. It should be noted that the type of bias element used can be varied depending on the needs of the application. For instance, elastic cylindrical members, multiple coils, expansive clips, leaf springs and the like, can all be used instead of a spring-like member. The bias element can also be integral to the guide element 391.

FIG. 22E depicts system 350 in position over a relatively healthy portion of spinal column 10, for instance after the spinal defect has been corrected. FIG. 22F depicts system 350 in position over a defective spinal column upon implantation or during treatment. Here, spinous process 14-2 is part of a vertebral body that is deflected with respect to the adjacent vertebral body, and this deflection is corrected by the use of system 350. Springs 394-1 and 395-1 create a compressive force against plates 357-1 and 358-1, respectively, and force those plates toward a more vertical alignment. Here, plate 358-1 is forced against the left side of spinous process 14-2, urging spinous process 14-2 to rotate and/or translate toward a corrected vertical alignment directly inferior to spinous process 14-1 (as depicted in FIG. 22E).

This configuration provides for a self-adjusting corrective force that can take into account slow movement of the vertebral bodies over the course of usage of system 350. For instance, as the vertebral body of spinous process 14-2 moves toward a proper alignment, the magnitude and direction of the corrective force applied by plates 357-1 and 358-1 will likewise adjust to compensate for this movement, yet continue to urge the vertebral body toward the proper alignment.

The relative corrective force applied by each bias element 394 and 395 can be varied so as to apply relatively more force from one side of the system if needed. Also, the force applied by the bias elements on the superior side of the link can be relatively greater or weaker than the force applied on the inferior side. For instance, in this embodiment, bias elements 394-1 and 395 are preferably stronger than bias elements 394-2 and 395-2, respectively, to bias outer link 351 toward a more vertical orientation, i.e., to force outer link 351-1 to rotate in a clockwise direction about the inferior base of inner link 352-1. The medical professional could choose to use more rigid springs (i.e., configured to apply a relatively greater bias) directly adjacent to vertebral bodies that have greater misalignment. The medical professional may also choose to use springs that are relatively weaker near the superior and inferior ends of the construct to taper off the applied forces.

In the embodiment described with respect to FIGS. 22E-F, insertion of system 350 over the spinous processes itself is sufficient to maintain system 350 in place on the spinal column. FIG. 22G is an exploded perspective view of another example embodiment, where system 350 is directly attached to each of the spinous processes in the region of the spine to be treated. It should be noted that the system 350 can be coupled to any number of spinous processes and it is not required to be connected to every spinous process in the region to be treated.

Here, plates 357-1 and 358-1 of outer link 351 include a superiorly located longitudinal slot 505-1 and 506-1, respectively. The inferior side of each plate includes a rounded aperture 507-1 and 508-1, respectively. Likewise, plates 359 and 360 of the inner links 352 each include superiorly located longitudinal slots 501 and 502 as well as inferiorly located rounded apertures 503 and 504, respectively. Preferably, a through-hole is created in each spinous process 14 through which guide element 391 can be inserted, though guide element 391 could be attached to the spinous process in any manner as described with respect to FIGS. 4A-12D. Here, guide element 391 also acts as an engagement device for coupling system 350 to the spinal column. Annular spacers 397 are preferably positioned about guide element 391 on both sides of spinous process 14 and are used to provide spacing between the bone and the corrective system as well as to provide cushioning and/or to more evenly apply corrective force across the surface of the spinous process 14.

Also shown here are bias members 394 and 395 for placement on the guide element 391 after guide element 391 has been inserted through the plates of the inner and outer links 351 and 352. Attachable retaining elements 392 and 393 are coupled with the ends of guide element 391 to retain bias element 394 and 395 on guide element 391. In this embodiment, the ends of guide elements 391 are threaded and retaining elements 392 and 393 are configured as nuts that can be screwed thereon. One of skill in the art will readily recognize that many different attachable configurations can be used for retaining element 392 and 393.

A guide element with a circular cross section allows for rotation of the plates about the guide element with relatively low friction. The rounded apertures fix the respective plates with respect to the guide element, while the slots allow for flexion and extension of the spine. Additional longitudinal slots can be used instead of the rounded apertures, if desired, so long as the plates are prevented from excessive movement.

Figure 22H:
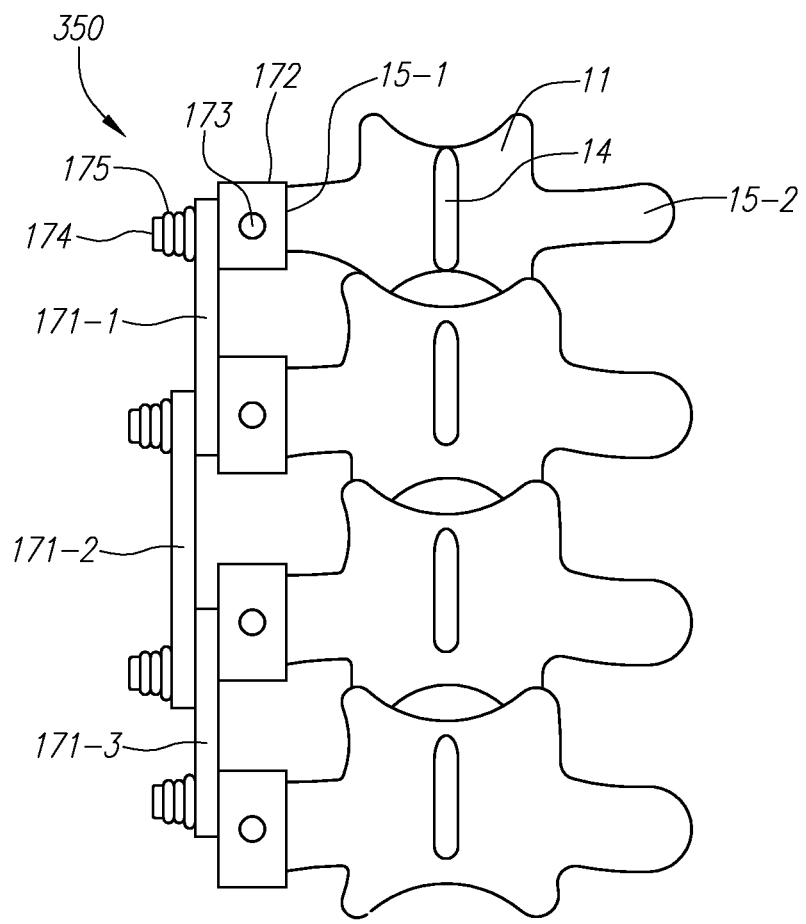
FIG. 22H is a posterior view depicting another example embodiment of a treatment system coupled with a corrected spinal column.
Figure 22I:
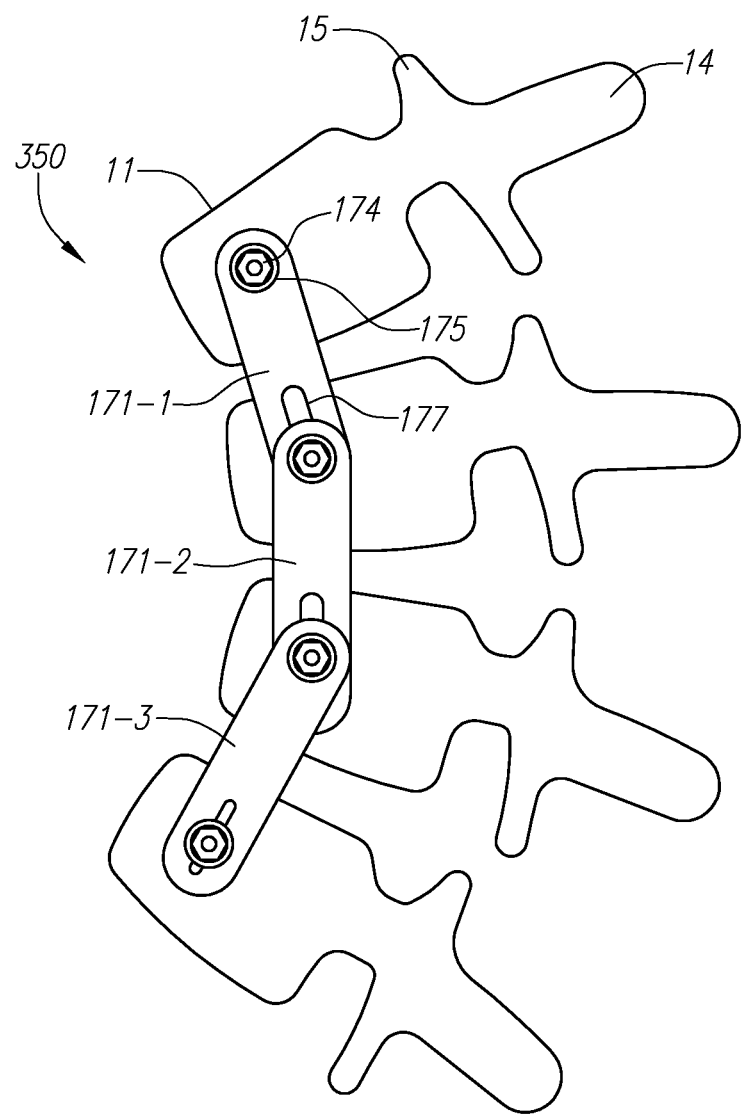
FIG. 22I is a side view depicting another example embodiment of a treatment system coupled with a spinal column in a state of extension.
Figure 22J:
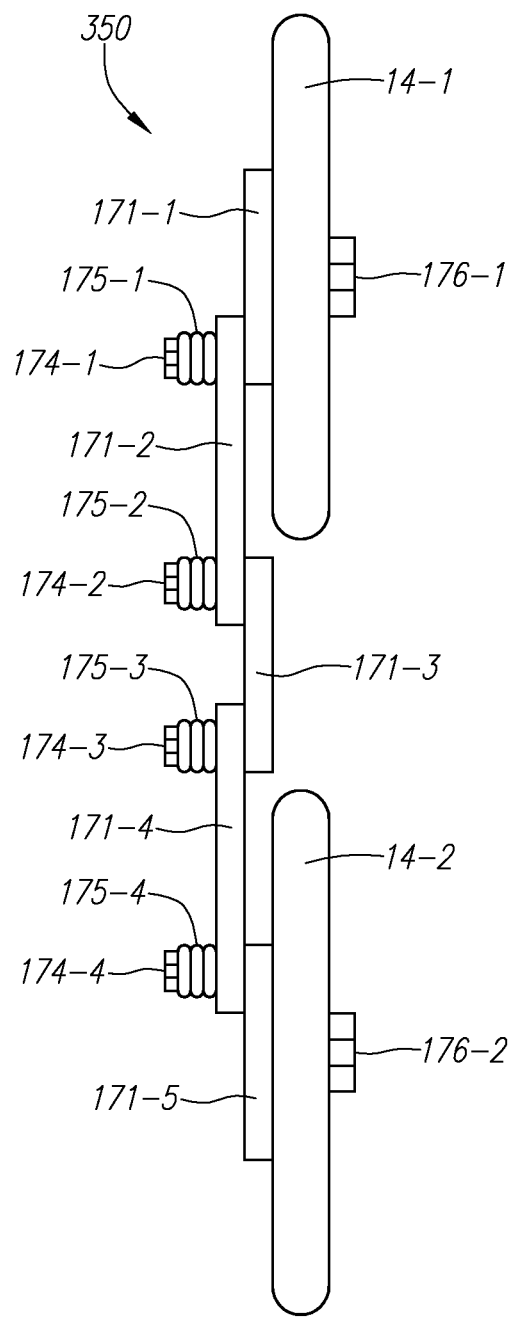
FIG. 22J is a posterior view depicting another example embodiment of a treatment system coupled with a corrected spinal column.

FIGS. 22H-J depict additional example embodiments of system 350. FIG. 22H is a posterior view of a patient's spinal column with an example embodiment of system 350 having only one link 171 spanning the region between each vertebral body 11. These links 171 are coupled with transverse processes 15-1 of each vertebral body as opposed to spinous process 14. As noted herein, there are certain drawbacks to this approach; namely, the method of implantation necessary to gain access to the transverse process is relatively more invasive and risks excessive blood loss. However, such a manner of attachment can be employed should it be desired.

Both ends of each link 171 are coupled to a transverse process 15. For instance, the upper end of the most superior link 171-1 shown here is coupled with a housing (or engagement device) 172 that attaches over transverse process 15-1. Link 171-1 is preferably attached to housing 172 using guide element 174, which is also routed through bias element 175 (similar to bias elements 394 and 395 described previously) and through a longitudinal slot (not shown) in link 171-1. Housing 172 is, in turn, coupled with transverse process 15-1 by a bone anchor 173. A similar configuration is used to couple the remaining links to the adjacent transverse processes with adjacent links connected in an overlapping manner. The presence of bias elements 175 and longitudinal slots allows deformation from the alignment shown here to be corrected while at the same time allowing the patient to move in the sagittal plane.

FIG. 22I depicts a similar embodiment to FIG. 22H coupled with the lateral side of the main body portion of each vertebral body 11 with guide element 174, which also serves as an engagement device. Attachment in this manner allows system 350 to be placed closer to the major axis of the patient's spinal column and directly to the vertebral bodies to be corrected, as opposed to the posteriorly positioned processes. Also shown here are longitudinal slots 177 positioned to allow guide elements 174 to slide therein.

FIG. 22J depicts another example embodiment of system 350 where multiple links 171 span the region between two adjacent spinous processes 14. This or a similar configuration can be used to couple with additional spinous processes of other vertebral bodies as well. Here, the most superior link 171-1 is coupled directly to spinous process 14-1 with an anchor element (or engagement device) 176-1. Link 171-1 is also coupled to an inferiorly located link 171-2 with a guide element 174-1 having a bias element 175-1 placed between an enlarged end of guide element 174 and the adjacent link plate. Although not shown, guide element 174 is preferably placed through a longitudinal slot (similar to slot 177 of FIG. 22I) in one of links 171-1 and 171-2. Similar attachments are present for links 171-3, 171-4 and 171-5, which are the most inferiorly located links. Link 171-5 is in turn coupled with the spinous process 14-2 with anchor element 176-2.

Figure 22K:
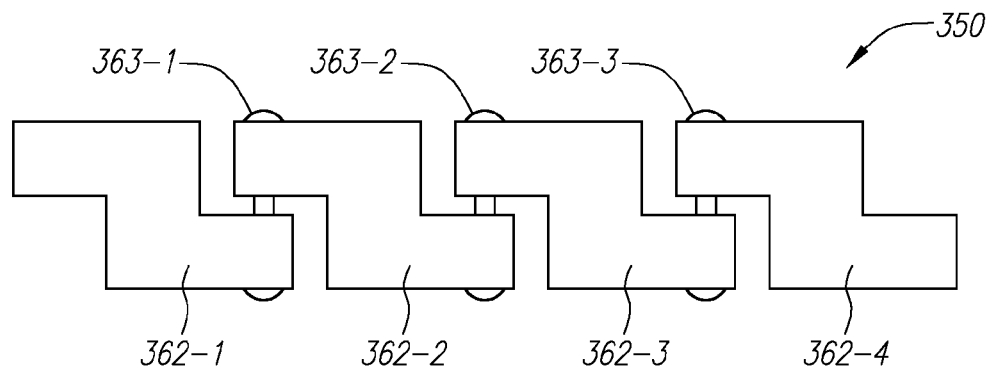
FIG. 22K is a side view of another example embodiment of a treatment system.

FIG. 22K is a top-down view of another example embodiment of system 350 where only one type of link 362 is used. Here, link 362 has a rigid uni-body construction with a multisided, stepped shape that is complementary to the shape on the opposite side. This configuration allows each link to interface with each adjacent link to provide a closer fit and to allow each link to be coupled together with a single guide element 363. Based on this disclosure, one of ordinary skill in the art will readily recognize that many similar shapes can be used instead of this multisided or stepped shape. Although not shown, each guide pin 363 is preferably contained within a longitudinal slot in one or both of each adjacent links 352 to allow the same pivoting movement and longitudinal translative movement as described with respect to FIGS. 22A-C. Each link 362 can be a solid element or can include multiple plates as described with respect to FIG. 22D.

The example embodiments of FIGS. 22A-H can each be used instead of a rigid rod, as described with respect to the earlier embodiments herein. For instance, one or more link-based systems 350 can be contained within tubular sleeves and used instead of the rigid rods of FIGS. 2A-B and the rod bundles of FIGS. 2C-D. Also, each link-based system 350 can be coupled directly to the adjacent spinous processes as shown and described with respect to FIG. 22D.

Figure 23A:
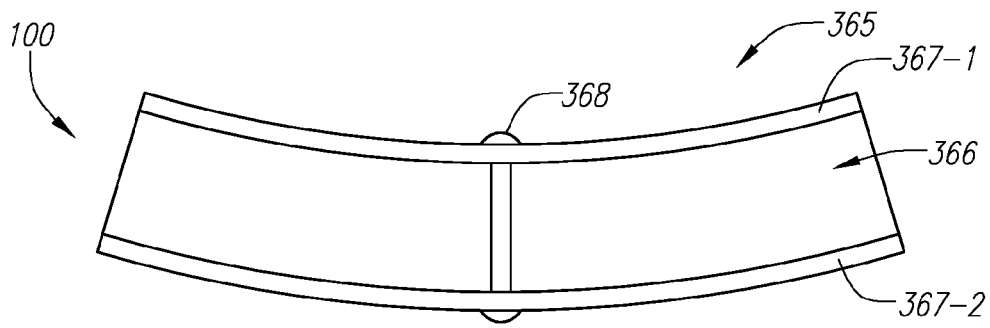
FIG. 23A is a bottom-up view of another example embodiment of a treatment system.
Figure 23B:
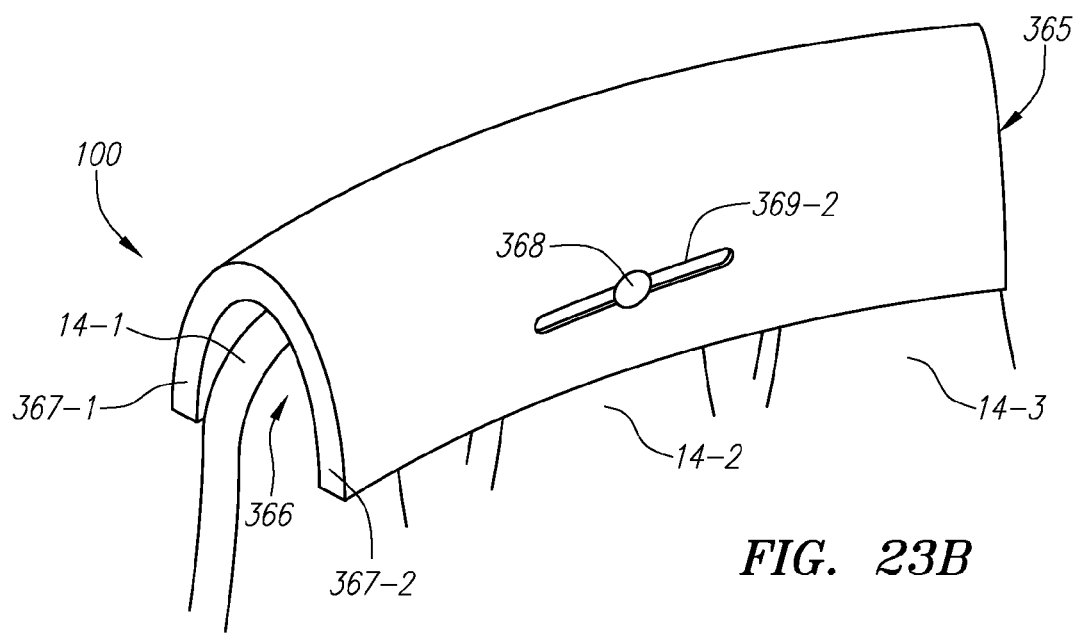

FIGS. 23A-B depict an example embodiment of system 100 including one or more corrective sections 365. Each section 365 preferably includes a U-shaped or parabolic channel 366 with opposing sidewalls 367-1 and 367-2. Section 365 is preferably curved along its longitudinal axis or otherwise shaped to apply the appropriate corrective force. FIG. 23A is a bottom-up view of section 365, and a perspective view is shown in FIG. 23B. In this example, section 365 is coupled over three adjacent spinal processes 14. The middlemost spinous process 14-2 has a guide element 368 routed through a man-made aperture therein. Guide element 368 is also contained within two longitudinal slots 369-1 and 369-2 present on opposite sides of section 365. This configuration allows section 365 to slide and pivot about element 368 as the patient's spinal column transitions through flexion and extension. Multiple adjacent sections 365 can be used to treat patients having deformities present over a larger span of the spinal column. Section 365 can be configured to cover any number of two or more spinous processes with the preferred configuration being three as shown in FIG. 23B. If desired, additional slots 369 and guide elements 368 can be included for one or more other spinous processes. In such an example, slots 369 can be offset above and below each other to allow sufficient space between them.

Figure 24:
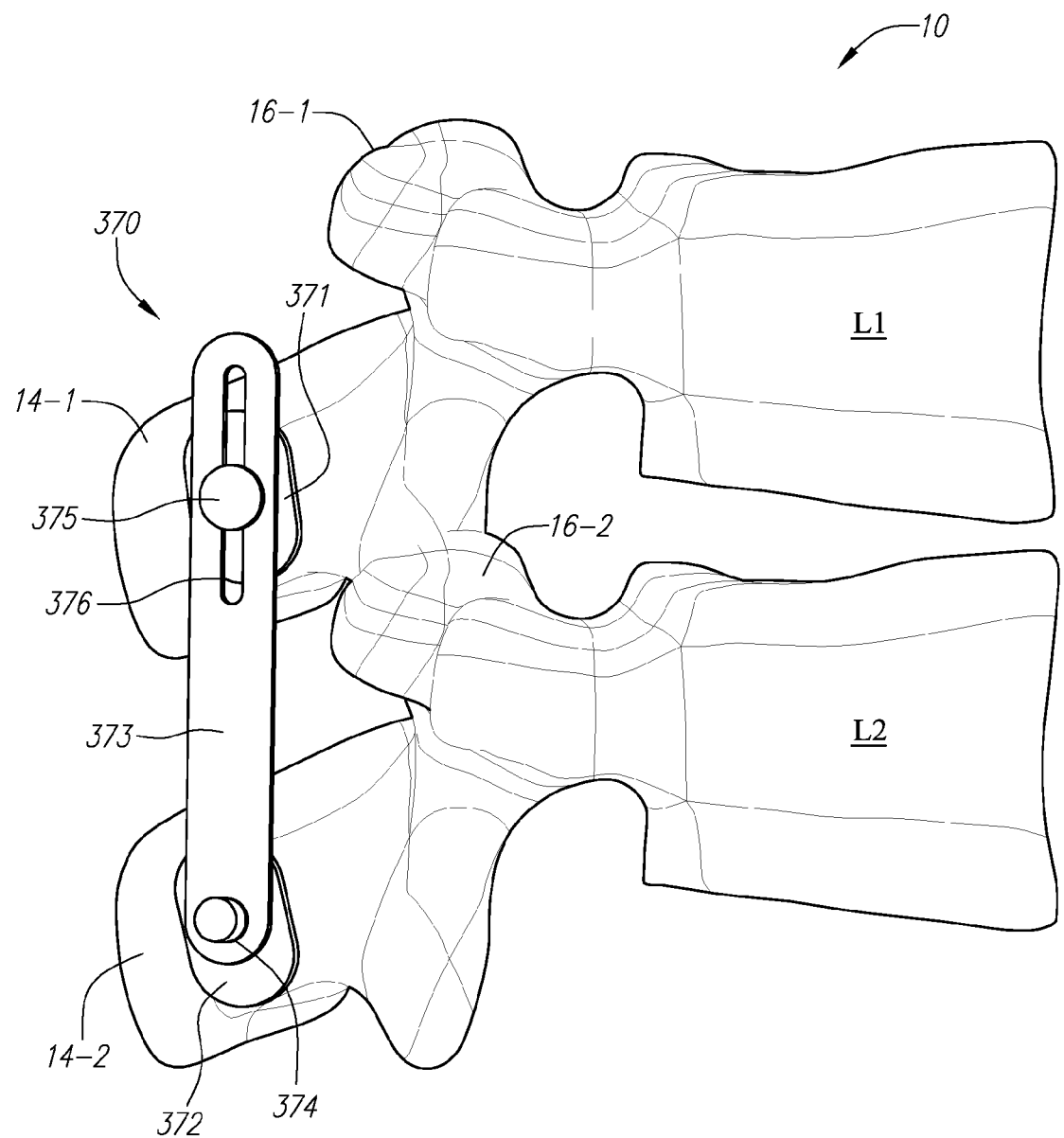

FIG. 24 is a side view of a patient's spinal column with another example embodiment of a corrective treatment system 370. Here, lumbar vertebrae L1 and L2 are shown having corrective system 370 attached thereto. System 370 includes two connectors (or engagement devices) 371 and 372 securely coupled to the spinous processes of vertebrae L1 and L2. Connectors 371 and 372 can each be coupled with the spinous process in any desired manner, including but not limited to the methods of attachment described in the many embodiments herein. Connector 371 includes a base plate to which a retaining guide element 375 is coupled. Similarly, connector 371 also includes a base plate with a guide element 374 (e.g., a pin and the like) coupled thereto.

An elongate rigid strut (or plate) 373 is connected to each of the opposing connectors 371 and 372. Strut 373 can be curved or otherwise shaped to apply a corrective force on the adjacent vertebral bodies. Strut 373 includes a longitudinal slot 376 in which guide element 375 is retained by an enlarged head portion of guide element 375. Strut 373 also includes an aperture (not shown) that receives guide element 374 on connector 372. Again, guide element 374 also preferably includes an enlarged head to retain strut 373. Strut 373 can pivot around guide element 374 and guide element 375. Strut 373 can also translate longitudinally with respect to guide pin 375 but is held in position relative to guide element 374 by the absence of a corresponding similar slot. This configuration can be used on two or more adjacent vertebrae, preferably with connectors 371 coupled to any additional vertebrae and corresponding slots 376 present on strut 373 to allow sliding translation with respect to each additional vertebral body. At least one such connector 372 is preferably included to maintain strut 373 in the proper position. This configuration allows the application of corrective force in the coronal plane while at the same time allowing the patient to enjoy significant freedom of movement during flexion and extension.

It should be noted that various embodiments are described herein with reference to one or more numerical values. These numerical value(s) are intended as examples only and in no way should be construed as limiting the subject matter recited in any claim, absent express recitation of a numerical value in that claim.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure.

What is claimed is:

1. A system for the treatment of scoliosis, comprising:
   an elongate, bendable rod having a longitudinal axis and configured to apply a corrective force to the spine of a patient;
   a first retainer securely connectable to a first vertebral body having a coronal plane and a sagittal plane, the first retainer being connectable to the rod such that the rod is permitted to pivot in the coronal and sagittal planes but is substantially not permitted to rotate around the longitudinal axis, the rod being permitted to pivot in the coronal plane around an axis that intersects the rod;
   a second retainer securely connectable to a second vertebral body, the second retainer being connectable to the rod such that the rod is permitted to move longitudinally with respect to the retainer, rotate with respect to the retainer, and pivot in the sagittal and coronal planes,
   wherein the first and second retainers are configured as housings, and
   wherein the rod has an axle member and the first retainer is configured to receive the axle member in a first lumen.

2. The system of claim 1, wherein rod is pivotable around a longitudinal axis of the axle member in the coronal plane.

3. The system of claim 2, wherein the first retainer comprises a second lumen configured to receive the rod.

4. The system of claim 3, wherein the first retainer comprises a first and a second housing securely connectable with each other.

5. The system of claim 4, wherein the first housing is connectable to a spinous process of the first vertebral body and the second housing is connectable to the first housing in a posterior-to-anterior direction when the first housing is connected to the spinous process.

6. The system of claim 4, wherein the first housing comprises a plurality of engagement features configured to engage with the spinous process.

7. The system of claim 1, wherein the second retainer is configured as a tubular housing having a lumen configured to receive the rod.

8. The system of claim 7, wherein the lumen has a diameter greater than the rod diameter along the length of the lumen, such that the rod can be placed in spaced relation to the inner walls of the tubular housing.

9. The system of claim 8, wherein the tubular housing has a first and a second end and a first diameter of the lumen between the first and second ends, the first diameter being greater than the diameter at each of the first and second ends.

10. The system of claim 8, wherein the second retainer comprises a first and a second housing securely connectable with each other.

11. The system of claim 10, wherein the first housing is connectable to a spinous process of the second vertebral body and the second housing is connectable to the first housing in a posterior-to-anterior direction when the first housing is connected to the spinous process.

12. The system of claim 1, wherein the first retainer is connectable to the first spinous process and the rod without any intervening moving parts.

13. The system of claim 1, wherein the second retainer is connectable to the second spinous process and the rod without any intervening moving parts.

14. The system of claim 1, wherein the rod is permitted to pivot in the sagittal plane about an axis that intersects the rod.

15. A system for the treatment of scoliosis, comprising:
    an elongate, bendable rod having a longitudinal axis and configured to apply a corrective force to the spine of a patient;
    a first retainer securely connectable to a first vertebral body having a coronal plane and a sagittal plane, the first retainer being connectable to the rod such that the rod is permitted to pivot in the coronal and sagittal planes but is substantially not permitted to rotate around the longitudinal axis, the rod being permitted to pivot in the coronal plane around an axis that intersects the rod;
    a second retainer securely connectable to a second vertebral body, the second retainer being connectable to the rod such that the rod is permitted to move longitudinally with respect to the retainer, rotate with respect to the retainer, and pivot in the sagittal and coronal planes,
    wherein the second retainer comprises a first housing, a second housing and a tubular member having a lumen configured to receive the rod, the first and second housings each having a recess configured to receive the tubular member and hold the member in fixed relation to the first and second housings.

16. A medical system configured to treat scoliosis, comprising:
    a first strut-like member having a first longitudinal slot;
    a second strut-like member coupled with the first strut-like member such that the first and second strut-like members can slide with respect to each other and pivot with respect to each other;

a guide element configured to couple the second strut-like member to the first strut-like member through the longitudinal slot such that the guide element is slidable within the longitudinal slot and the first and second strut-like members can pivot with respect to each other about the guide element; and a bias element positioned between a first end of the guide element and the first and second strut-like members, the bias element being configured to bias the first and second strut-like members away from the first end of the guide element;

wherein the first and second strut-like members are each positionable adjacent a first and second vertebral body, respectively, and at least one of the first and second strut-like members is configured to apply a corrective force in the coronal plane to at least one of the vertebral bodies when implanted within a patient.

17. The medical system of claim 16, wherein the first and second strut-like members comprise a material that exhibits a corrective return force upon bending.

18. The medical system of claim 17, wherein the first and second strut-like members comprise nitinol.

19. The medical system of claim 16, further comprising a third strut-like member having a second longitudinal slot and a fourth strut-like member, wherein the guide element is further configured to couple the third strut-like member to the fourth strut-like member through the second longitudinal slot such that the guide element is slidable within the second longitudinal slot of the third strut-like member and the third and fourth strut-like members can pivot with respect to each other around the guide element.

20. The medical system of claim 19, further comprising a spacer positioned on the guide element such that the first and second strut-like members reside on one side of the spacer and the third and fourth strut-like members reside on the second side of the spacer.

21. The medical system of claim 20, wherein the spacer has a width configured to match substantially the width of a spinous process.

22. The medical system of claim 20, wherein the bias element is a first bias element, the system further comprising:
a second bias element positioned between a second end of the guide element and the third and fourth strut-like members, the second bias element being configured to bias the third and fourth strut-like members away from the second end of the guide element.

23. The medical system of claim 20, wherein the guide element is configured to be mounted to a spinous process.

24. The medical system of claim 16, wherein the first and second strut-like members are pivotally coupled together by way of at least one intervening strut-like member.

25. The medical system of claim 16, further comprising:
a first engagement device configured to couple the first strut-like member to the first vertebral body; and
a second engagement device configured to couple the second strut-like member to the second vertebral body.

26. The medical system of claim 25, wherein the first and second engagement devices are configured to couple with the spinous processes of the first and second vertebral bodies, respectively.

27. The medical system of claim 16, wherein the first and second strut-like members are configured to be pivotable in the sagittal plane when implanted within a patient.

28. The medical system of claim 16, wherein the system is configured such that no corrective force is applied in the sagittal plane when implanted within the patient.

29. The medical system of claim 16, wherein the first and second strut-like members are plates.

30. A medical system configured to treat scoliosis, comprising:
a first strut-like member having a first longitudinal slot;
a second strut-like member coupled with the first strut-like member such that the first and second strut-like members can slide with respect to each other and pivot with respect to each other;
a third strut-like member having a second longitudinal slot;
a fourth strut-like member;
a guide element configured to couple the second strut-like member to the first strut-like member through the longitudinal slot such that the guide element is slidable within the longitudinal slot and the first and second strut-like members can pivot with respect to each other about the guide element; and
a spacer positioned on the guide element such that the first and second strut-like members reside on a first side of the spacer and the third and fourth strut-like members reside on a second side of the spacer;
wherein the guide element is further configured to couple the third strut-like member to the fourth strut-like member through the second longitudinal slot such that the guide element is slidable within the second longitudinal slot and the third and fourth strut-like members can pivot with respect to each other around the guide element,
wherein the spacer has a width configured to substantially match the width of a spinous process, and
wherein the first and second strut-like members are each positionable adjacent a first and second vertebral body, respectively, and at least one of the first and second strut-like members is configured to apply a corrective force in the coronal plane to at least one of the vertebral bodies when implanted within a patient.

31. A medical system configured to treat scoliosis, comprising:
a first strut-like member having a first longitudinal slot;
a second strut-like member coupled with the first strut-like member such that the first and second strut-like members can slide with respect to each other and pivot with respect to each other;
a third strut-like member having a second longitudinal slot;
a fourth strut-like member;
a guide element configured to couple the second strut-like member to the first strut-like member through the longitudinal slot such that the guide element is slidable within the longitudinal slot and the first and second strut-like members can pivot with respect to each other about the guide element;
a spacer positioned on the guide element such that the first and second strut-like members reside on a first side of the spacer and the third and fourth strut-like members reside on a second side of the spacer;
a first bias element positioned between a first end of the guide element and the first and second strut-like members, the first bias element being configured to bias the first and second strut-like members away from the first end of the guide element; and
a second bias element positioned between a second end of the guide element and the third and fourth strut-like members, the second bias element being configured to bias the third and fourth strut-like members away from the second end of the guide element,
wherein the guide element is further configured to couple the third strut-like member to the fourth strut-like member through the second longitudinal slot such that the guide element is slidable within the second longitudinal slot and the third and fourth strut-like members can pivot with respect to each other around the guide element, and wherein the first and second strut-like members are each positionable adjacent a first and second vertebral body, respectively, and at least one of the first and second strut-like members is configured to apply a corrective force in the coronal plane to at least one of the vertebral bodies when implanted within a patient.

32. A medical system configured to treat scoliosis, comprising:

a first strut-like member having a first longitudinal slot;

a second strut-like member coupled with the first strut-like member such that the first and second strut-like members can slide with respect to each other and pivot with respect to each other;

a third strut-like member having a second longitudinal slot;

a fourth strut-like member;

a guide element configured to couple the second strut-like member to the first strut-like member through the longitudinal slot such that the guide element is slidable within the longitudinal slot and the first and second strut-like members can pivot with respect to each other about the guide element; and a spacer positioned on the guide element such that the first and second strut-like members reside on a first side of the spacer and the third and fourth strut-like members reside on a second side of the spacer;

wherein the guide element is further configured to be mounted to a spinous process and to couple the third strut-like member to the fourth strut-like member through the second longitudinal slot such that the guide element is slidable within the second longitudinal slot and the third and fourth strut-like members can pivot with respect to each other around the guide element, wherein the first and second strut-like members are each positionable adjacent a first and second vertebral body, respectively, and at least one of the first and second strut-like members is configured to apply a corrective force in the coronal plane to at least one of the vertebral bodies when implanted within a patient.

\* \* \* \* \*